US012778826B2

(12) United States Patent
Rigoni et al.

(10) Patent No.: US 12,778,826 B2
(45) Date of Patent: Nov. 3, 2026

(54) APPARATUS AND SYSTEM FOR BOOSTING, TRANSFERRING, TURNING AND POSITIONING A PATIENT

(71) Applicant: Sage Products, LLC, Cary, IL (US)

(72) Inventors: Michael J. Rigoni, Cary, IL (US); Garret W. Sweetwood, Lake in the Hills, IL (US); Paul M. Fowler, Rockford, IL (US); Gregory T. Davis, Woodstock, IL (US); Jeffrey A. Kennedy, Algonquin, IL (US); Paul H. Hanifl, Barrington Hills, IL (US); Craig S. Golden, Arlington Heights, IL (US); Mark D. Olson, Crystal Lake, IL (US)

(73) Assignee: SAGE PRODUCTS, LLC, Cary, IL (US)

( * ) Notice: Subject to any disclaimer, the term of this patent is extended or adjusted under 35 U.S.C. 154(b) by 47 days.

(21) Appl. No.: 18/737,306

(22) Filed: Jun. 7, 2024

(65) Prior Publication Data

US 2024/0325225 A1 Oct. 3, 2024

Related U.S. Application Data

(63) Continuation of application No. 17/012,725, filed on Sep. 4, 2020, now Pat. No. 12,295,897, which is a (Continued)

(51) Int. Cl.

*A61G 7/057* (2006.01)
*A47C 27/08* (2006.01)

(Continued)

(52) U.S. Cl.

CPC .......... *A61G 7/05769* (2013.01); *A61G 1/01* (2013.01); *A61G 7/001* (2013.01);

(Continued)

(58) Field of Classification Search

CPC ............... A61G 7/05769; A61G 7/001; A61G 7/05715; A61G 7/1021; A61G 7/1026;

(Continued)

(56) References Cited

U.S. PATENT DOCUMENTS

| | | | |
|---|---|---|---|
| 542,720 | A | 7/1895 | Weiss |
| 674,451 | A | 5/1901 | Bunker |

(Continued)

FOREIGN PATENT DOCUMENTS

| | | | |
|---|---|---|---|
| AU | 2008256995 | A1 | 12/2008 |
| CA | D188671 | | 11/2020 |

(Continued)

OTHER PUBLICATIONS

Blaine Miller, Provisional Draft Declaration, U.S. Pat. No. 8,511,314, Reexamination Control No. U.S. Appl. No. 90/013,087, published Dec. 18, 2018, 11 pages.

(Continued)

*Primary Examiner* — Justin C Mikowski

(74) *Attorney, Agent, or Firm* — Foley & Lardner LLP

(57) ABSTRACT

A system for use with an inflatable device includes an air output and a nozzle at a distal end of the air output. The nozzle includes a lip extending radially from the nozzle and configured to retain the nozzle in a port of the inflatable device. The lip has a non-circular shape around the nozzle.

19 Claims, 30 Drawing Sheets

Related U.S. Application Data continuation of application No. 15/494,262, filed on Apr. 21, 2017, now Pat. No. 10,765,576, which is a continuation-in-part of application No. 14/942,604, filed on Nov. 16, 2015, now Pat. No. 9,861,544, which is a continuation of application No. 14/829,361, filed on Aug. 18, 2015, now Pat. No. 9,849,053.

(60) Provisional application No. 62/326,548, filed on Apr. 22, 2016.

(51) Int. Cl.

| | |
|---|---|
| ***A47C 27/10*** | (2006.01) |
| ***A61F 13/15*** | (2006.01) |
| ***A61G 1/01*** | (2006.01) |
| ***A61G 7/00*** | (2006.01) |
| ***A61G 7/10*** | (2006.01) |

(52) U.S. Cl.
CPC ....... *A61G 7/05715* (2013.01); *A61G 7/1021* (2013.01); *A61G 7/1026* (2013.01); *A47C 27/08* (2013.01); *A47C 27/081* (2013.01); *A47C 27/10* (2013.01); *A61F 2013/15154* (2013.01)

(58) Field of Classification Search
CPC . A61G 1/01; A61G 5/12; A61G 5/121; A61G 5/122; A61G 5/124; A61G 5/125; A61G 5/127; A61G 5/128; A61G 5/14; A47C 20/027; A47C 20/025; A47C 20/021; A47C 20/022; A47C 20/023; A47C 20/026; A47C 20/02; A47C 20/00; A47C 27/08; A47C 27/081; A47C 27/10; A47G 9/10; A47G 9/1027; A47G 9/1054; A47G 9/1072; A47G 2009/1018; A61F 2013/15154
See application file for complete search history.

(56) References Cited

U.S. PATENT DOCUMENTS

| | | | | | |
|---|---|---|---|---|---|
| 1,334,901 | A | | 3/1920 | Higdon | |
| 1,726,939 | A | | 9/1929 | Anderson | |
| 2,068,134 | A | | 1/1937 | Houghton | |
| 2,573,375 | A | | 10/1951 | Winstead | |
| 2,582,439 | A | | 1/1952 | Kavanagh | |
| 2,750,606 | A | | 6/1956 | Freedlander et al. | |
| 2,804,911 | A | | 9/1957 | Howarth | |
| D195,020 | S | | 4/1963 | Emery | |
| 3,112,956 | A | | 12/1963 | Shick et al. | |
| 3,155,991 | A | | 11/1964 | Dunham | |
| 3,166,799 | A | | 1/1965 | Milton | |
| 3,178,732 | A | | 4/1965 | Stibitz | |
| 3,205,010 | A | | 9/1965 | Schick | |
| 3,325,832 | A | | 6/1967 | Malicki | |
| 3,333,286 | A | * | 8/1967 | Biolik .................... | A47C 27/15 5/639 |
| 3,452,372 | A | | 7/1969 | Emery | |
| 3,474,781 | A | | 10/1969 | Gaylord, Jr. | |
| 3,477,071 | A | | 11/1969 | Emerson | |
| 3,503,649 | A | | 3/1970 | Johnson | |
| 3,523,563 | A | | 8/1970 | Louis | |
| 3,536,117 | A | | 10/1970 | Huber | |
| 3,653,083 | A | | 4/1972 | Lapidus | |
| 3,778,851 | A | | 12/1973 | Howorth | |
| 3,785,395 | A | | 1/1974 | Andreasson | |
| 3,811,140 | A | | 5/1974 | Burpo | |
| 3,829,914 | A | | 8/1974 | Treat | |
| 3,933,154 | A | | 1/1976 | Cabansag | |
| 3,965,503 | A | | 6/1976 | Gridel | |
| 4,030,719 | A | | 6/1977 | Gabriele et al. | |
| 4,048,681 | A | | 9/1977 | Baulch et al. | |
| 4,066,072 | A | | 1/1978 | Cummins | |
| 4,073,021 | A | | 2/1978 | Carlisle | |
| 4,108,170 | A | | 8/1978 | Spann | |
| 4,132,228 | A | | 1/1979 | Green | |
| 4,214,326 | A | * | 7/1980 | Spann .................. | A47C 20/027 5/632 |
| 4,233,700 | A | * | 11/1980 | Spann .................. | A47C 20/027 5/632 |
| 4,247,963 | A | | 2/1981 | Reddi | |
| 4,272,856 | A | | 6/1981 | Wegener et al. | |
| 4,370,769 | A | | 2/1983 | Herzig et al. | |
| 4,389,742 | A | | 6/1983 | Dewitt | |
| 4,391,010 | A | | 7/1983 | Kronman | |
| 4,417,710 | A | | 11/1983 | Adair | |
| 4,425,676 | A | | 1/1984 | Crane | |
| 4,509,214 | A | | 4/1985 | Shea | |
| 4,517,690 | A | | 5/1985 | Wegener | |
| 4,528,704 | A | | 7/1985 | Wegener et al. | |
| 4,554,693 | A | | 11/1985 | Calloway | |
| 4,627,426 | A | | 12/1986 | Wegener et al. | |
| 4,627,796 | A | | 12/1986 | Moore | |
| 4,662,016 | A | | 5/1987 | Seeman | |
| 4,662,366 | A | | 5/1987 | Tari | |
| 4,675,925 | A | | 6/1987 | Littleton | |
| 4,686,719 | A | | 8/1987 | Johnson et al. | |
| 4,694,515 | A | | 9/1987 | Rogers, Jr. | |
| 4,802,249 | A | * | 2/1989 | Bills .................... | A47C 20/027 5/632 |
| 4,809,484 | A | | 3/1989 | Lovik | |
| 4,823,417 | A | | 4/1989 | Fukuichi | |
| 4,858,625 | A | | 8/1989 | Cramer | |
| 4,867,230 | A | | 9/1989 | Voss | |
| D305,458 | S | | 1/1990 | Wang | |
| 4,905,712 | A | | 3/1990 | Bowlin et al. | |
| 4,908,895 | A | | 3/1990 | Walker | |
| 4,912,861 | A | | 4/1990 | Huang | |
| 4,944,053 | A | | 7/1990 | Smith | |
| 4,977,629 | A | | 12/1990 | Jones | |
| 5,012,821 | A | | 5/1991 | Tarver | |
| 5,016,650 | A | | 5/1991 | Marlar | |
| 5,022,110 | A | | 6/1991 | Stroh | |
| 5,056,533 | A | | 10/1991 | Solano | |
| 5,060,324 | A | | 10/1991 | Marinberg et al. | |
| 5,067,189 | A | | 11/1991 | Weedling et al. | |
| 5,070,559 | A | | 12/1991 | Pettifer | |
| 5,086,543 | A | | 2/1992 | Mitchell | |
| 5,088,747 | A | | 2/1992 | Morrison et al. | |
| 5,103,518 | A | | 4/1992 | Gilroy et al. | |
| 5,111,838 | A | | 5/1992 | Langston | |
| 5,123,699 | A | | 6/1992 | Warburton | |
| 5,138,731 | A | | 8/1992 | Harcrow, Jr. | |
| 5,142,720 | A | | 9/1992 | Kelso et al. | |
| 5,144,708 | A | | 9/1992 | Pekar | |
| 5,148,563 | A | | 9/1992 | Klearman et al. | |
| D331,270 | S | | 11/1992 | Johnson et al. | |
| 5,168,589 | A | | 12/1992 | Stroh et al. | |
| 5,182,828 | A | | 2/1993 | Alivizatos | |
| 5,193,238 | A | * | 3/1993 | Clute ................... | A47D 15/008 5/655 |
| 5,199,121 | A | | 4/1993 | Payne | |
| 5,226,186 | A | | 7/1993 | Boyd | |
| 5,274,862 | A | | 1/1994 | Palmer et al. | |
| 5,280,657 | A | | 1/1994 | Stagg | |
| 5,329,655 | A | | 7/1994 | Garner | |
| 5,331,698 | A | | 7/1994 | Newkirk et al. | |
| 5,362,302 | A | | 11/1994 | Jensen et al. | |
| 5,369,829 | A | | 12/1994 | Jay | |
| 5,373,595 | A | | 12/1994 | Johnson et al. | |
| 5,390,384 | A | | 2/1995 | Dinsmoor et al. | |
| D356,156 | S | | 3/1995 | Boland | |
| 5,395,162 | A | | 3/1995 | Jay et al. | |
| 5,398,678 | A | | 3/1995 | Gamow | |
| 5,426,801 | A | | 6/1995 | Klearman et al. | |
| 5,438,721 | A | | 8/1995 | Pahno et al. | |
| 5,447,235 | A | | 9/1995 | Pharo | |
| 5,448,790 | A | * | 9/1995 | Saro ..................... | A47C 17/045 5/632 |
| 5,451,179 | A | | 9/1995 | Laroi, Jr. et al. | |
| 5,452,487 | A | | 9/1995 | Leggett | |

(56) References Cited

U.S. PATENT DOCUMENTS

| | | | | |
|---|---|---|---|---|
| 5,476,105 | A | 12/1995 | Toth | |
| D369,054 | S | 4/1996 | Straub et al. | |
| D369,934 | S | 5/1996 | Straub et al. | |
| 5,524,307 | A | 6/1996 | Griffin | |
| RE35,299 | E | 7/1996 | Weedling et al. | |
| 5,549,121 | A | 8/1996 | Vinci | |
| 5,561,873 | A | 10/1996 | Weedling | |
| 5,603,591 | A | 2/1997 | Mclellan | |
| RE35,468 | E | 3/1997 | Newman | |
| 5,632,769 | A | 5/1997 | Kappel et al. | |
| 5,634,224 | A | 6/1997 | Stephen | |
| 5,671,977 | A | 9/1997 | Jay et al. | |
| D385,143 | S | 10/1997 | Straub et al. | |
| 5,702,153 | A | 12/1997 | Pliska | |
| 5,742,958 | A | 4/1998 | Solazzo | |
| 5,787,523 | A | 8/1998 | Lindberg | |
| 5,797,155 | A | 8/1998 | Maier et al. | |
| 5,806,928 | A | 9/1998 | Gattuso et al. | |
| 5,830,780 | A | 11/1998 | Dennison et al. | |
| 5,836,027 | A | 11/1998 | Leventhal et al. | |
| 5,836,654 | A | 11/1998 | Debellis et al. | |
| 5,957,491 | A | 9/1999 | Cech et al. | |
| 5,997,491 | A * | 12/1999 | Harris | A47C 20/021 128/882 |
| 6,009,873 | A * | 1/2000 | Neviaser | A47C 20/027 128/DIG. 20 |
| 6,012,183 | A | 1/2000 | Brooke et al. | |
| 6,073,291 | A | 6/2000 | Davis | |
| 6,082,824 | A | 7/2000 | Chow | |
| 6,102,936 | A | 8/2000 | Augustine et al. | |
| 6,108,861 | A | 8/2000 | Vystrcil et al. | |
| 6,145,143 | A | 11/2000 | Hicks et al. | |
| 6,154,900 | A * | 12/2000 | Shaw | A61G 7/001 5/81.1 R |
| 6,159,172 | A | 12/2000 | Gray et al. | |
| 6,223,368 | B1 | 5/2001 | Anslin | |
| 6,223,369 | B1 | 5/2001 | Maier et al. | |
| 6,240,584 | B1 | 6/2001 | Perez et al. | |
| 6,241,320 | B1 | 6/2001 | Chew et al. | |
| 6,241,755 | B1 | 6/2001 | Arnold et al. | |
| 6,273,810 | B1 | 8/2001 | Rhodes et al. | |
| 6,317,909 | B1 | 11/2001 | Blum | |
| 6,327,724 | B1 | 12/2001 | Sharrock et al. | |
| 6,347,642 | B1 | 2/2002 | Schulte | |
| 6,357,084 | B1 | 3/2002 | Haidon | |
| 6,367,106 | B1 | 4/2002 | Gronsman | |
| 6,374,435 | B1 | 4/2002 | Leininger et al. | |
| 6,413,194 | B1 | 7/2002 | Gant | |
| 6,415,466 | B1 | 7/2002 | Laiso | |
| 6,427,268 | B1 | 8/2002 | Davis | |
| 6,467,106 | B1 | 10/2002 | Heimbrock | |
| 6,484,334 | B1 | 11/2002 | Borders et al. | |
| 6,510,574 | B2 | 1/2003 | Sharrock et al. | |
| 6,541,094 | B1 | 4/2003 | Landvik et al. | |
| 6,543,068 | B1 | 4/2003 | Penninger | |
| 6,560,793 | B2 | 5/2003 | Walker | |
| 6,653,363 | B1 | 11/2003 | Tursi et al. | |
| 6,658,676 | B1 | 12/2003 | Persson et al. | |
| 6,666,426 | B1 | 12/2003 | Taylor | |
| 6,698,041 | B2 | 3/2004 | Vansteenburg et al. | |
| 6,701,544 | B2 | 3/2004 | Heimbrock | |
| 6,701,558 | B2 | 3/2004 | Vansteenburg | |
| 6,701,559 | B2 | 3/2004 | Boso et al. | |
| 6,804,845 | B2 * | 10/2004 | Stewart, III | A61G 7/07 5/652 |
| 6,820,292 | B2 | 11/2004 | Heimbrock | |
| 6,874,176 | B2 | 4/2005 | Berge | |
| 6,898,809 | B2 | 5/2005 | Davis | |
| D508,182 | S | 8/2005 | Colonello | |
| D509,270 | S | 9/2005 | Jason | |
| 6,964,073 | B1 | 11/2005 | Curry | |
| 6,966,275 | B2 | 11/2005 | Whitehill | |
| 7,007,330 | B2 | 3/2006 | Kuiper et al. | |
| 7,028,350 | B1 | 4/2006 | Davis | |
| 7,032,261 | B2 | 4/2006 | Heimbrock | |
| 7,040,706 | B2 | 5/2006 | Koffler | |
| 7,074,166 | B2 | 7/2006 | Weitzman | |
| 7,107,641 | B2 | 9/2006 | Davis | |
| 7,114,204 | B2 | 10/2006 | Patrick | |
| 7,131,154 | B2 | 11/2006 | Davis et al. | |
| 7,168,115 | B2 | 1/2007 | Davis | |
| 7,210,176 | B2 | 5/2007 | Weedling et al. | |
| 7,225,486 | B2 | 6/2007 | Jackson | |
| 7,240,384 | B2 | 7/2007 | Dudonis | |
| 7,243,382 | B2 | 7/2007 | Weedling et al. | |
| 7,266,852 | B2 | 9/2007 | Davis | |
| D555,248 | S | 11/2007 | Rugfelt et al. | |
| 7,337,485 | B2 | 3/2008 | Metzger | |
| 7,340,785 | B2 | 3/2008 | Weedling et al. | |
| 7,373,680 | B2 | 5/2008 | Davis | |
| 7,376,995 | B2 | 5/2008 | Davis | |
| 7,406,723 | B2 | 8/2008 | Davis | |
| 7,415,738 | B2 | 8/2008 | Weedling et al. | |
| 7,467,431 | B2 | 12/2008 | Weedling et al. | |
| 7,506,387 | B1 | 3/2009 | Scordato et al. | |
| 7,565,709 | B2 | 7/2009 | Davis | |
| 7,571,498 | B2 | 8/2009 | Jewell et al. | |
| 7,574,761 | B2 | 8/2009 | Davis | |
| 7,591,029 | B2 | 9/2009 | Weedling et al. | |
| 7,627,910 | B2 | 12/2009 | Davis | |
| 7,650,654 | B2 | 1/2010 | Lambarth et al. | |
| D610,852 | S | 3/2010 | Rothschild et al. | |
| 7,676,862 | B2 | 3/2010 | Poulos et al. | |
| 7,681,262 | B2 | 3/2010 | Weedling et al. | |
| D613,105 | S | 4/2010 | Chuang | |
| 7,712,170 | B2 | 5/2010 | Davis | |
| 7,731,282 | B2 | 6/2010 | Leeds | |
| 7,731,283 | B2 | 6/2010 | Leeds | |
| 7,735,164 | B1 | 6/2010 | Patrick | |
| 7,739,758 | B2 | 6/2010 | Weedling et al. | |
| 7,757,318 | B2 | 7/2010 | Poulos et al. | |
| 7,784,132 | B2 | 8/2010 | Gonzalez et al. | |
| 7,810,193 | B1 | 10/2010 | Ennis et al. | |
| 7,900,299 | B2 | 3/2011 | Weedling et al. | |
| 7,914,081 | B1 | 3/2011 | Smith | |
| 7,914,611 | B2 | 3/2011 | Vrzalik et al. | |
| 7,954,187 | B1 | 6/2011 | Earnest | |
| 7,971,292 | B1 | 7/2011 | Sithian | |
| 8,001,635 | B2 | 8/2011 | Humbles | |
| 8,118,920 | B2 | 2/2012 | Vrzalik | |
| 8,127,382 | B1 | 3/2012 | Plascencia et al. | |
| 8,128,065 | B2 | 3/2012 | King et al. | |
| 8,161,583 | B1 | 4/2012 | Palen | |
| D663,428 | S | 7/2012 | GÃ-Ransson et al. | |
| 8,214,951 | B1 | 7/2012 | Batta | |
| 8,234,727 | B2 | 8/2012 | Schreiber et al. | |
| 8,276,222 | B1 | 10/2012 | Patrick | |
| 8,302,222 | B2 | 11/2012 | Jasani | |
| 8,353,069 | B1 | 1/2013 | Miller | |
| 8,372,182 | B2 | 2/2013 | Vrzalik et al. | |
| 8,387,177 | B2 | 3/2013 | Davis | |
| 8,413,277 | B2 | 4/2013 | Davis et al. | |
| 8,464,376 | B1 | 6/2013 | Waite | |
| 8,464,720 | B1 | 6/2013 | Pigazzi et al. | |
| 8,511,314 | B2 | 8/2013 | Pigazzi et al. | |
| 8,539,621 | B2 | 9/2013 | West | |
| 8,539,622 | B2 | 9/2013 | West | |
| 8,539,623 | B2 | 9/2013 | West | |
| 8,566,977 | B2 | 10/2013 | Davis | |
| 8,590,574 | B2 | 11/2013 | Jian et al. | |
| 8,601,623 | B1 | 12/2013 | West | |
| 8,602,032 | B2 | 12/2013 | Goldsmith | |
| 8,661,580 | B2 | 3/2014 | Giap | |
| 8,678,418 | B1 | 3/2014 | Quarles | |
| 8,782,830 | B2 | 7/2014 | Brykalski et al. | |
| 8,789,533 | B2 | 7/2014 | Steffens et al. | |
| D712,555 | S | 9/2014 | Berg | |
| 8,850,634 | B2 | 10/2014 | Ponsi et al. | |
| 8,918,930 | B2 | 12/2014 | Stroh et al. | |
| 8,978,184 | B1 | 3/2015 | Garrett | |
| 9,132,052 | B2 | 9/2015 | Fowler et al. | |
| 9,161,876 | B2 | 10/2015 | Pigazzi et al. | |
| 9,254,231 | B2 | 2/2016 | Vrzalik et al. | |
| 9,271,588 | B1 | 3/2016 | Phillips et al. | |

(56) References Cited

U.S. PATENT DOCUMENTS

| | | | |
|---|---|---|---|
| 9,308,122 | B2 | 4/2016 | Dunlop |
| 9,321,392 | B1 | 4/2016 | Lebrun |
| 9,326,903 | B2 | 5/2016 | Locke |
| 9,332,850 | B2 | 5/2016 | Krishtul |
| 9,375,343 | B2 | 6/2016 | Marshall et al. |
| D767,148 | S | 9/2016 | Perreault |
| 9,522,078 | B2 | 12/2016 | Pizzini |
| 9,538,853 | B2 | 1/2017 | Vrzalik et al. |
| 9,554,956 | B2 | 1/2017 | Reiners et al. |
| D781,615 | S | 3/2017 | Parman |
| 9,675,509 | B2 | 6/2017 | Tilk et al. |
| 9,693,919 | B2 | 7/2017 | Berman |
| 9,693,920 | B2 | 7/2017 | Fowler et al. |
| 9,750,656 | B1 | 9/2017 | Pigazzi et al. |
| 9,782,287 | B2 | 10/2017 | Pigazzi et al. |
| 9,782,312 | B2 | 10/2017 | Brubaker et al. |
| 9,782,313 | B2 | 10/2017 | Hindson |
| 9,795,529 | B2 | 10/2017 | Lehtio |
| D802,223 | S | 11/2017 | Quantz |
| 9,835,344 | B2 | 12/2017 | Vrzalik et al. |
| 9,849,053 | B2 | 12/2017 | Rigoni et al. |
| D808,686 | S | 1/2018 | May et al. |
| 9,907,408 | B2 | 3/2018 | Vrzalik et al. |
| 9,931,262 | B2 | 4/2018 | Pigazzi et al. |
| 9,949,883 | B1 | 4/2018 | Pigazzi et al. |
| 9,962,122 | B2 | 5/2018 | Augustine et al. |
| 9,968,500 | B1 | 5/2018 | Amini et al. |
| 10,016,066 | B2 | 7/2018 | Howard |
| 10,034,808 | B2 | 7/2018 | Vrzalik et al. |
| 10,039,680 | B2 | 8/2018 | Galbraith |
| 10,045,902 | B1 | 8/2018 | Pigazzi et al. |
| 10,064,770 | B2 | 9/2018 | Reiners et al. |
| 10,092,470 | B2 | 10/2018 | Lewis |
| 10,098,800 | B2 | 10/2018 | Pigazzi et al. |
| 10,112,513 | B2 | 10/2018 | Patrick et al. |
| 10,159,533 | B2 | 12/2018 | Moll et al. |
| 10,172,470 | B1 | 1/2019 | Vrzalik et al. |
| 10,206,830 | B2 | 2/2019 | Fowler et al. |
| 10,285,888 | B2 | 5/2019 | Liu |
| 10,285,890 | B1 | 5/2019 | Pigazzi et al. |
| 10,314,417 | B2 | 6/2019 | Duck |
| 10,322,050 | B1 | 6/2019 | Pigazzi et al. |
| 10,363,185 | B2 | 7/2019 | Purdy et al. |
| 10,363,188 | B2 | 7/2019 | Young |
| 10,376,430 | B2 | 8/2019 | Liu |
| 10,398,614 | B2 | 9/2019 | Rigoni et al. |
| 10,500,115 | B2 | 12/2019 | Weedling |
| 10,512,578 | B2 | 12/2019 | Visco |
| 10,561,522 | B2 | 2/2020 | Giap |
| 10,568,435 | B2 | 2/2020 | Luckemeyer et al. |
| 10,576,004 | B1 | 3/2020 | Frances |
| 10,588,800 | B2 | 3/2020 | Fletcher et al. |
| D880,901 | S | 4/2020 | Raad et al. |
| 10,709,626 | B1 | 7/2020 | Gomez |
| 10,716,724 | B2 | 7/2020 | Vrzalik et al. |
| D897,132 | S | 9/2020 | Mckinney |
| 10,765,576 | B2 | 9/2020 | Rigoni et al. |
| 10,765,580 | B1 | 9/2020 | Augustine |
| 10,772,778 | B2 | 9/2020 | Hahn et al. |
| 10,828,216 | B2 | 11/2020 | Phalen et al. |
| D907,777 | S | 1/2021 | Hahn et al. |
| 10,912,699 | B2 | 2/2021 | Pigazzi et al. |
| D911,748 | S | 3/2021 | Luo |
| 10,993,866 | B2 | 5/2021 | Augustine |
| 11,020,301 | B2 | 6/2021 | Messerschmidt |
| D934,591 | S | 11/2021 | Cuadra |
| 11,224,548 | B2 | 1/2022 | Depauw |
| 11,224,550 | B1 | 1/2022 | Gomez |
| 11,266,525 | B2 | 3/2022 | Kaforey et al. |
| 11,298,282 | B2 | 4/2022 | Davis et al. |
| 11,324,650 | B2 | 5/2022 | Zhou et al. |
| 11,364,166 | B2 | 6/2022 | Grindstaff et al. |
| 11,439,551 | B2 | 9/2022 | Davis et al. |
| 11,471,317 | B1 | 10/2022 | Spears |
| D970,257 | S | 11/2022 | Klerer |
| 11,484,431 | B2 | 11/2022 | Allen |
| 11,484,456 | B2 | 11/2022 | Pigazzi et al. |
| 11,510,836 | B2 | 11/2022 | Cole et al. |
| 11,607,358 | B2 | 3/2023 | Spahn et al. |
| 11,638,670 | B1 | 5/2023 | Volz et al. |
| 11,642,267 | B2 | 5/2023 | Kea et al. |
| 11,654,068 | B2 | 5/2023 | Giap |
| 11,661,129 | B2 | 5/2023 | Chambers et al. |
| 11,701,281 | B2 | 7/2023 | Meah |
| D997,364 | S | 8/2023 | Hahn et al. |
| 11,737,939 | B2 | 8/2023 | Davis et al. |
| D1,004,016 | S | 11/2023 | Howard |
| D1,005,738 | S | 11/2023 | Fan |
| 11,833,091 | B2 | 12/2023 | Vrzalik et al. |
| 11,890,240 | B2 | 2/2024 | Ponsi et al. |
| D1,033,986 | S | 7/2024 | Pinter |
| D1,035,318 | S | 7/2024 | De Grasse et al. |
| 12,208,044 | B2 | 1/2025 | Kurt et al. |
| 12,390,383 | B2 | 8/2025 | Fowler |
| D1,092,098 | S | 9/2025 | Mo |
| D1,103,649 | S | 12/2025 | Chen |
| 12,508,182 | B2 | 12/2025 | Wolters et al. |
| 12,533,276 | B2 | 1/2026 | Fox et al. |
| D1,122,450 | S | 4/2026 | Fowler |
| 2001/0013146 | A1 | 8/2001 | Wempe |
| 2001/0040402 | A1 | 11/2001 | Odderson |
| 2002/0029417 | A1 | 3/2002 | Walker |
| 2002/0108179 | A1 | 8/2002 | Kiser |
| 2002/0109381 | A1 | 8/2002 | Duncan |
| 2002/0112286 | A1 | 8/2002 | Upton et al. |
| 2002/0133877 | A1 | 9/2002 | Kuiper et al. |
| 2002/0148045 | A1 | 10/2002 | Giori et al. |
| 2002/0148474 | A1 | 10/2002 | Larson |
| 2003/0009952 | A1 | 1/2003 | Gallant et al. |
| 2003/0014821 | A1 | 1/2003 | Boyd |
| 2003/0030319 | A1 | 2/2003 | Clapper |
| 2003/0041379 | A1 | 3/2003 | Habboub et al. |
| 2003/0061663 | A1 | 4/2003 | Lampel |
| 2003/0066134 | A1 | 4/2003 | Chapman |
| 2003/0159212 | A1 | 8/2003 | Patrick et al. |
| 2003/0205920 | A1 | 11/2003 | Sprouse et al. |
| 2004/0083550 | A1 | 5/2004 | Graebe, Jr. |
| 2004/0123382 | A1 | 7/2004 | Berge |
| 2004/0237203 | A1 | 12/2004 | Romano et al. |
| 2005/0005358 | A1* | 1/2005 | DuDonis ................ A61G 7/065 5/652 |
| 2005/0028273 | A1 | 2/2005 | Weedling et al. |
| 2005/0034242 | A1 | 2/2005 | Davis |
| 2005/0055768 | A1 | 3/2005 | Assink |
| 2005/0076437 | A1 | 4/2005 | Johnson |
| 2005/0091749 | A1 | 5/2005 | Humbles |
| 2005/0102750 | A1 | 5/2005 | Berge |
| 2005/0151410 | A1 | 7/2005 | Sprouse |
| 2005/0210595 | A1 | 9/2005 | Di Stasio et al. |
| 2005/0229314 | A1* | 10/2005 | Chisari ................ A47C 20/026 5/632 |
| 2005/0235423 | A1 | 10/2005 | Hetzel et al. |
| 2006/0000016 | A1 | 1/2006 | Weedling et al. |
| 2006/0037142 | A1* | 2/2006 | Binder ..................... A47G 9/10 5/644 |
| 2006/0072347 | A1 | 4/2006 | Ferraro |
| 2006/0075562 | A1 | 4/2006 | Digirolamo |
| 2006/0162086 | A1 | 7/2006 | Davis |
| 2006/0213010 | A1 | 9/2006 | Davis |
| 2007/0006388 | A1 | 1/2007 | Townsend |
| 2007/0072690 | A1 | 3/2007 | Berenson et al. |
| 2007/0074760 | A1 | 4/2007 | Wu |
| 2007/0118993 | A1 | 5/2007 | Bates |
| 2007/0266494 | A1 | 11/2007 | Deluca et al. |
| 2007/0283498 | A1 | 12/2007 | Shelby |
| 2008/0022461 | A1 | 1/2008 | Bartlett et al. |
| 2008/0028516 | A1 | 2/2008 | Morishima |
| 2008/0029940 | A1 | 2/2008 | Kammer et al. |
| 2008/0078033 | A1 | 4/2008 | Wyatt et al. |
| 2008/0209630 | A1 | 9/2008 | Kazala et al. |
| 2008/0216231 | A1 | 9/2008 | Lambarth et al. |
| 2008/0289102 | A1 | 11/2008 | Davis |
| 2009/0000037 | A1 | 1/2009 | Graebe, Jr. |
| 2009/0211168 | A1 | 8/2009 | Bogar |

(56) References Cited

U.S. PATENT DOCUMENTS

2009/0265857 A1 10/2009 Habegger
2009/0295203 A1 12/2009 Lewis et al.
2010/0257703 A1 10/2010 Vass
2010/0263127 A1* 10/2010 Jamshidi .............. A47C 20/025 29/428
2010/0290931 A1 11/2010 Sanders et al.
2011/0035880 A1 2/2011 Cole et al.
2011/0056017 A1 3/2011 Schreiber et al.
2011/0068939 A1 3/2011 Lachenbruch
2011/0072579 A1 3/2011 Receveur et al.
2011/0219546 A1 9/2011 West
2011/0247725 A1 10/2011 Frayne et al.
2011/0271444 A1 11/2011 Davis
2011/0277234 A1 11/2011 Jasani
2011/0296609 A1 12/2011 Giap
2011/0304186 A1 12/2011 Andrews
2012/0009844 A1 1/2012 Waters et al.
2012/0073053 A1 3/2012 Turner et al.
2012/0073056 A1 3/2012 Freund et al.
2012/0085430 A1 4/2012 Johansson et al.
2012/0124752 A1 5/2012 Patrick
2012/0131746 A1 5/2012 Griffin et al.
2012/0144594 A1 6/2012 Nash
2012/0186012 A1* 7/2012 Ponsi .................. A61G 7/1026 5/81.1 R
2012/0186013 A1* 7/2012 Ponsi ..................... A61G 7/001 5/81.1 R
2012/0186587 A1* 7/2012 Steffens ................. A61G 7/001 128/845
2012/0210511 A1 8/2012 Davis
2012/0245500 A1 9/2012 Polliack et al.
2012/0255124 A1 10/2012 West
2012/0292958 A1 11/2012 Sprouse, II
2012/0304384 A1 12/2012 Scholz et al.
2012/0311783 A1 12/2012 Chiang et al.
2013/0019882 A1 1/2013 Durham et al.
2013/0042409 A1 2/2013 Gil Gomez et al.
2013/0042414 A1 2/2013 Schreiber et al.
2013/0104907 A1 5/2013 Giap
2013/0145549 A1 6/2013 Piegdon et al.
2013/0152950 A1 6/2013 Giap
2013/0205495 A1* 8/2013 Ponsi ................... A61G 7/0507 5/81.1 HS
2013/0232693 A1* 9/2013 Myers .................... A47C 7/383 5/636
2013/0263377 A1 10/2013 Wootten
2013/0269111 A1 10/2013 Berg
2013/0270881 A1 10/2013 Fowler et al.
2013/0318723 A1 12/2013 Li
2013/0320746 A1 12/2013 Amirault et al.
2013/0340772 A1 12/2013 Carlson et al.
2014/0007351 A1 1/2014 Cohen
2014/0082836 A1 3/2014 Patrick et al.
2014/0250601 A1 9/2014 Gomez
2014/0277307 A1 9/2014 Gammons et al.
2014/0283305 A1 9/2014 Zysman
2014/0304918 A1 10/2014 Steffens et al.
2014/0338121 A1 11/2014 Giap
2014/0352072 A1 12/2014 Holladay
2014/0366271 A1 12/2014 Marshall et al.
2015/0040326 A1 2/2015 Fairburn et al.
2015/0101126 A1 4/2015 Reiners et al.
2015/0113735 A1 4/2015 Anderson et al.
2015/0122266 A1 5/2015 Saunders et al.
2015/0128341 A1 5/2015 Kuiper et al.
2015/0143628 A1* 5/2015 Fowler ................. A61G 7/1026 5/652
2015/0189996 A1 7/2015 Scarlett et al.
2015/0224217 A1 8/2015 Rogers
2015/0225097 A1 8/2015 Anastasia
2015/0238378 A1 8/2015 Bhat et al.
2015/0289817 A1 10/2015 Augustine et al.
2015/0290027 A1 10/2015 Augustine et al.
2015/0290062 A1 10/2015 Augustine et al.
2015/0335165 A1 11/2015 Creekmuir et al.
2015/0369384 A1 12/2015 Frayne
2016/0095777 A1 4/2016 Berman
2016/0213179 A1* 7/2016 Beckman ................ A47G 9/10
2016/0228281 A1 8/2016 Marshall et al.
2016/0245439 A1 8/2016 Fry
2016/0279007 A1 9/2016 Flatt
2017/0049646 A1 2/2017 Rigoni et al.
2017/0049647 A1 2/2017 Rigoni et al.
2017/0065473 A1 3/2017 Scott
2017/0112655 A1 4/2017 Giap
2017/0119608 A1 5/2017 Rigoni et al.
2017/0216117 A1 8/2017 Rigoni et al.
2017/0231410 A1 8/2017 Chon et al.
2017/0239118 A1 8/2017 Cole et al.
2017/0326011 A1 11/2017 Alvarez et al.
2018/0017177 A1 1/2018 Marson et al.
2018/0104125 A1* 4/2018 Vahala ................... A61G 7/075
2018/0140457 A1 5/2018 Sarma
2018/0192960 A1 7/2018 Augustine et al.
2018/0200130 A1 7/2018 Liu
2018/0221229 A1 8/2018 Kaiser et al.
2018/0221242 A1 8/2018 Lee et al.
2018/0289174 A1 10/2018 Ye et al.
2018/0303690 A1 10/2018 Hahn et al.
2018/0311097 A1 11/2018 Rodzewicz et al.
2018/0353360 A1 12/2018 Kea et al.
2018/0369050 A1 12/2018 Davis et al.
2019/0046382 A1 2/2019 Fiset et al.
2019/0049027 A1 2/2019 Bais
2019/0059603 A1 2/2019 Griffith et al.
2019/0083341 A1 3/2019 Ulreich et al.
2019/0091084 A1 3/2019 Messerschmidt
2019/0104996 A1 4/2019 Augustine et al.
2019/0151177 A1 5/2019 Giap
2019/0159843 A1 5/2019 Demri et al.
2019/0358102 A1 11/2019 Ueda
2019/0365586 A1 12/2019 Latiff et al.
2020/0008976 A1 1/2020 Molloy et al.
2020/0060912 A1 2/2020 Hollabaugh et al.
2020/0100606 A1 4/2020 Ganji
2020/0360216 A1 11/2020 Larkin et al.
2021/0077327 A1 3/2021 Kurt et al.
2021/0093498 A1 4/2021 Lafleche et al.
2021/0275371 A1 9/2021 Fowler et al.
2021/0401076 A1 12/2021 Jenkins et al.
2022/0000692 A1 1/2022 Gomez
2022/0023121 A1 1/2022 Davis
2022/0096304 A1 3/2022 Kaiser et al.
2022/0323283 A1 10/2022 Boulos et al.
2022/0339045 A1 10/2022 Cook et al.
2023/0011458 A1 1/2023 Parikh et al.
2023/0064553 A1 3/2023 Fogel et al.
2024/0156661 A1 5/2024 Kaforey
2024/0156662 A1 5/2024 Kaforey et al.
2024/0216201 A1 7/2024 Fox et al.

FOREIGN PATENT DOCUMENTS

CN 108741913 A 11/2018
CN 208259823 U 12/2018
CN 211326149 U 8/2020
CN 306633192 6/2021
DE 10 2010 007 457 8/2011
EP 3 162 347 A1 5/2017
EP 3 705 100 A1 9/2020
EP 3 861 972 A1 8/2021
EP 3 890 560 A1 10/2021
EP 3 705 100 B1 1/2022
FR 2923367 A1 5/2009
GB 2 300 845 A 11/1996
GB 2 402 075 A 12/2004
GB 2 415 912 1/2006
GB 6 302 170 8/2023
JP 10-117907 A 5/1998
SE 527345 C2 2/2006
WO WO-88/10082 A1 12/1988
WO WO-96/27357 A1 9/1996
WO WO-02/065877 A1 8/2002

(56) References Cited

FOREIGN PATENT DOCUMENTS

| | | | |
|---|---|---|---|
| WO | WO-2004/050002 | A1 | 6/2004 |
| WO | WO-2005/007673 | | 1/2005 |
| WO | WO-2005/086664 | A2 | 9/2005 |
| WO | WO-2005/107673 | A1 | 11/2005 |
| WO | WO-2012/001423 | | 1/2012 |
| WO | WO-2012/170934 | A2 | 12/2012 |
| WO | WO-2015/081233 | A1 | 6/2015 |
| WO | WO-2015/081271 | A2 | 6/2015 |
| WO | WO-2017/185039 | A2 | 10/2017 |
| WO | WO-2017/197326 | A1 | 11/2017 |
| WO | WO-2019/060424 | A1 | 3/2019 |
| WO | WO-2019/152624 | A1 | 8/2019 |
| WO | WO-2020/041493 | A1 | 2/2020 |
| WO | WO-2020/136796 | A1 | 7/2020 |
| WO | WO-2022/226309 | A1 | 10/2022 |

OTHER PUBLICATIONS

Craig Kaforey, Declaration, U.S. Pat. No. 8,511,314, Reexamination Control No. U.S. Appl. No. 90/013,087, published Sep. 10, 2014, 13 pages.
Craig Kaforey, Declaration, U.S. Pat. Nos. 8,511,314 and 8,464,720, Reexamination Control Nos. U.S. Appl. No. 90/013,088 and U.S. Appl. No. 90/013,088, published Apr. 18, 2014, 3 pages.
Craig Kaforey, Declaration, U.S. Pat. Nos. 8,511,314 and 8,464,720, Reexamination Control Nos. U.S. Appl. No. 90/013,088 and U.S. Appl. No. 90/013,088, published Sep. 10, 2014, 6 pages.
Dr. Alessio Pigazzi, Declaration, U.S. Pat. Nos. 8,511,314 and 8,464,720, Reexamination Control Nos. U.S. Appl. No. 90/013,088 and U.S. Appl. No. 90/013,088, published Sep. 10, 2014, 30 pages.
Dr. Gustavo Plasencia, Declaration, U.S. Pat. Nos. 8,511,314 and 8,464,720, Reexamination Control Nos. U.S. Appl. No. 90/013,088 and U.S. Appl. No. 90/013,088, published Sep. 10, 2014, 28 pages.
Dr. Maheswari Senthil, Declaration, U.S. Pat. No. 8,511,314, Reexamination Control No. U.S. Appl. No. 90/013,087, published Apr. 18, 2014, 18 pages.
Dr. Thomas Ljungman, Declaration, U.S. Pat. Nos. 8,511,314 and 8,464,720, Reexamination Control Nos. U.S. Appl. No. 90/013,088 and U.S. Appl. No. 90/013,088, published Sep. 10, 2014, 9 pages.
Examination Report No. 1 for AU App. No. 2019325331, issued Jul. 11, 2024, 3 pages.
Examination Report No. 1 for AU Application No. 2018285855, mailed Mar. 16, 2023, 3 pages.
Glenn E. Beltz, Affidavit, U.S. Pat. Nos. 8,511,314 and 8,464,720, Reexamination Control Nos. U.S. Appl. No. 90/013,088 and U.S. Appl. No. 90/013,088, published Sep. 10, 2014, 19 pages.
Gustavo Plasencia, Declaration, U.S. Pat. No. 8,511,314, Reexamination Control No. U.S. Appl. No. 90/013,087, published Apr. 18, 2014, 29 pages.
International Preliminary Report on Patentability for International Application No. PCT/US2022/018215, mailed Oct. 19, 2023, 10 pages.
International Search Report and Written Opinion for International Application No. PCT/US2018/037372, mailed Sep. 13, 2018, 13 pages.
International Search Report and Written Opinion for International Application No. PCT/US2022/018215, mailed Aug. 9, 2022, 18 pages.
Jennifer Klauschie et al., "Use of Anti-Skid Material and Patient-Positioning to Prevent Patient Shifting during Robotic-Assisted Gynecologic Procedures," J. Minim Invasive Gynecol., 2010; 17(4):504-507.
Michael Madigan, Affidavit, U.S. Pat. Nos. 8,511,314 and 8,464,720, Reexamination Control Nos. U.S. Appl. No. 90/013,088 and U.S. Appl. No. 90/013,088, published Sep. 10, 2014, 32 pages.
Paul Lloyd, Declaration, U.S. Pat. Nos. 8,511,314 and 8,464,720, Reexamination Control Nos. U.S. Appl. No. 90/013,088 and U.S. Appl. No. 90/013,088, published Sep. 10, 2014, 4 pages.
Record of Oral Hearing held Dec. 14, 2015, Appeal No. 2015-007832, Reexamination Control No. U.S. Appl. No. 90/013,088, mailed Jan. 4, 2016.
Soule Medical, Patient Positioning Systems Product Catalog, published Jan. 1, 2015, 63 pages.
Fanwer Positioner, Online, Published date Aug. 3, 2024, Retrieved on Aug. 14, 2025 from URL: https://www.amazon.com/Positioning-Wedge-Pillow-Connection-Positioners/dp/BODFXRKLCN (Year: 2024).
HoverMatt Positioner, Online, Published date Nov. 9, 2023, Retrieved on Aug. 14, 2025 from URL: https://WWW.youtube.com/watch?v=M LWnNkOowtA (Year: 2023).
"Boost" Definition in the Cambridge English Dictionary, Non-Final Office Action mailed on May 11, 2021, for U.S. Appl. No. 16/547,343.
"How to Set Up Kool Kat", Aug. 11, 2013, SKY High Amusements, Minutes 1:55-2:30, http://www.youtube.com/watch?v=a966cR6v6sc (Year: 2013).
Dec. 4, 2012—(WO) International Search Report and Written Opinion—App PCT/US2012/041729, 15 pages.
Dec. 10, 2013—International Preliminary Report on Patentability—App PCT/US2012/041729, 8 pages.
Dec. 31, 2013—(US) Final Office Action—U.S. Appl. No. 13/014,497.
Jul. 12, 2013—(WO) International Search Report and Written Opinion—App PCT/US2013/036448, 9 pages.
Jul. 2, 2013—(US) Non-Final Office Action—U.S. Appl. No. 13/014,497.
Mar. 20, 2013—(US) Non-Final Office Action—U.S. Appl. No. 13/014,500.
Mar. 28, 2014—(US) Non-Final Office Action—U.S. Appl. No. 13/156,103.
May 15, 2014—(WO) International Search Report and Written Opinion—App PCT/US12/22572, 25 pages.
Nov. 28, 2014—(EP) Search Report—App 14159820.1.
Jun. 25, 2015—(EP) Extended Search Report—App 12739957.4.
May 15, 2015—(WO) International Search Report and Written Opinion—App PCT/US2014/067672.
Sep. 14, 2015—(US) Non-Final Office Action—U.S. Appl. No. 13/838,952.
Mar. 14, 2016—(EP) Office Action—App 12739957.4.
Church et al., "Burn Wound Infections", Clinical Microbiology Reviews, 2006, vol. 19, No. 2, pp. 403-343.
Coleman Quick Pump Fitting Replacement Nozzle Main Adapter and Pinch Valve Tip, Sep. 6, 2014, Amazon.com, https://www.amazon.com/Coleman-Fitting-Replacement-Nozzle-Adapter/dp/B00JHRJ03A/ref=cm_cr_arp_d_product_top?ie=UTF8.
Communication pursuant to Article 94(3) EPC for EP Application No. 12728152.5 date Apr. 22, 2015, 5 pages.
Extended European Search Report for EP Application No. 19151698.8, dated Apr. 17, 2019, 6 pages.
Immedia OneWayGlide Rehab Assist, Jun. 15, 2004 http://www.rehabassist.com.au/immedia.htm.
International Search Report and Written Opinion for International Application No. PCT/US2017/028954, mailed Nov. 24, 2017, 16 pages.
International Search Report and Written Opinion for International Application No. PCT/US2019/047540, mailed Nov. 14, 2019, 13 pages.
OneWayGlide Instruction for Use, Immedia, Version 6, 2016, p. 7.
Photos of Stryker Glide holding strap, date unknown, two pages.
Prism Medical Company, 5300 Ergoglide Instructions, 2009, 2 pp. Maryland Heights, MO.
Romedic OneWaySlide, Handicare, Dec. 6, 2010.
Stryker Operations/Maintenance Manual for Stryker Glide Lateral Air Transfer System, Model 3062, date unknown, 33 pages.
Textbook of Palliative Nursing, Nov. 10, 2005, Oxford University Press, XP002740850, 1 page.
Waverley Glen, One-Way Glide—The Grimstead Range of Transfer and Repositioning Aids, Ontario Canada, downloaded Jun. 11, 2012, 3 pages.
Author Unknown, "Clinical Health Services, Inc. Therapist's Choice Triangle Massage Bolster Extra Large, 19" x 12" x 20" x 15.5", (Burgundy)," Clinical Health Services, Published Apr. 20, 2011,

(56) References Cited

OTHER PUBLICATIONS

Accessed on May 29, 2025 from URL: https://www.amazon.com/Therapists-Choice%C2%AE-Triangle-Massage-Burgundy/dp/B004XJ5112?th= 1v, 4 pages.
Author Unknown, "Positioning Wedge Pillow Side Sleeping Belt Connection, Limit Width Adjustable Bed Wedges Body Positioners for Back Pain Relief, Back Positioning Wedge for After Surgery, Anti Snoring, Back Support," Connection Positioner, Published Nov. 25, 2024, Accessed on May 29, 2026 from URL https://www.amazon.com/Positioning-Wedge-Pillow-Connection-Positioners/dp/BODFXRKLCN (9 pages).

* cited by examiner

APPARATUS AND SYSTEM FOR BOOSTING, TRANSFERRING, TURNING AND POSITIONING A PATIENT

CROSS-REFERENCE TO RELATED PATENT APPLICATIONS

This application is a continuation of U.S. patent application Ser. No. 17/012,725, filed Sep. 4, 2020, which is a continuation of U.S. patent application Ser. No. 15/494,262, filed Apr. 21, 2017, which claims the benefit of and priority to U.S. Provisional Patent Application No. 62/326,548, filed Apr. 22, 2016. U.S. patent application Ser. No. 15/494,262 is also a continuation-in-part of U.S. patent application Ser. No. 14/942,604, filed Nov. 16, 2015, which is a continuation of U.S. patent application Ser. No. 14/829,361, filed Aug. 18, 2015. The above-mentioned applications are herein incorporated by reference in their entireties.

BACKGROUND

The present invention generally relates to an apparatus, system, and method for boosting, transferring, turning, and positioning a person on a bed or the like, and, more particularly, to an inflatable patient support device having a gripping surface, an absorbent pad, and/or a wedge for use in turning and positioning a person, utilizing airflow, high and low friction surfaces to transfer or boost, and selective glide assemblies to allow, assist, or resist movement of the components of the system in certain directions, as well as systems and methods including one or more of such apparatuses.

Nurses and other caregivers at hospitals, assisted living facilities, and other locations often care for patients with limited or no mobility, many of whom are critically ill or injured and/or are bedridden. These patients are dependent upon nurses/caregivers to move, and are at risk of forming pressure ulcers (bed sores) due to their inability to move. Pressure ulcers develop due to pressure on a patient's skin for prolonged periods of time, particularly over areas where bone or cartilage protrudes close to the surface of the skin because such pressure reduces blood flow to the area eventually resulting in tissue death. The risk of forming a pressure ulcer is exacerbated by skin surface damage caused by frictional forces and shearing forces resulting from the patient's skin rubbing or pulling against a surface and excessive heat and moisture, which causes the skin to be more fragile and therefore more susceptible to damage.

One area in which pressure ulcers frequently form in an immobile patient lying on his/her back is over the sacral bone (the "sacrum"), because the sacrum and supporting mattress surface exert constant and opposing pressure on the skin, resulting in the aforementioned reduction in blood flow. Furthermore, skin in the sacral region is often more susceptible to damage due to shear and friction resulting from the patient being pushed or pulled over the surface of the mattress to reposition him/her, or from sliding down over the surface of the bed when positioned with his/her upper body in an inclined position for pulmonary reasons.

Existing devices and methods often do not adequately protect against pressure ulcers in bedridden patients, particularly pressure ulcers in the sacral region. One effective way to combat sacral pressure ulcers is frequent turning of the patient, so that the patient is alternately resting on one side or the other thus avoiding prolonged pressure in the sacral region. A protocol is often used for scheduled turning of a bedridden patient and dictates that a patient should be turned Q2, or every two hours, either from resting at a 30° angle on one side to a 30° angle on the other side, or from 30° on one side to 0°/supine (lying on his/her back) to 30° on the other side. However, there are several barriers to compliance with this type of protocol, resulting in patients not being turned as often as necessary, or positioning properly at a side-lying angle, to prevent pressure ulcers. First, turning patients is difficult and time consuming, typically requiring two or more caregivers. Second, pillows are often stuffed partially under the patient to support the patient's body in resting on his or her left or right side; however, pillows are non-uniform and can pose difficulties in achieving consistent turning angles, as well as occasionally slipping out from underneath the patient. Third, patients who are positioned in an inclined position on the bed often slide downward toward the foot of the bed over time, which can cause them to slip off of any structures that may be supporting them. Additionally, this requires the nurse/caregiver to frequently "boost" the patient back up to the head of the bed, which, like turning, can be difficult and time-consuming, and once again may result in shearing/friction of the patient's skin. Further, many patient positioning devices cannot be left under a patient for long periods of time, because they do not have sufficient breathability and/or compatibility with certain bed functions such as low-air loss (LAL) technology and can be easily stained when soiled.

Moreover, caregivers often need to move patients to or from a bed surface for transport, treatment, or examination of the patient. Patients who are unconscious, disabled, or otherwise unable to move under their own power often require the assistance of multiple caregivers to accomplish this transfer. The patient transfer process has traditionally relied upon one or more of several methods, including the use of folded bedsheets ("drawsheets") or rigid transfer boards in concert with the exertion of strong pushing or pulling forces by the caregivers to accomplish the move. The process may be complicated by the size of the patient, the patient's level of disability, and/or the patient's state of consciousness.

In addition to being difficult and time-consuming, turning, positioning, transferring and/or boosting patients, types of "patient handling" activities, can result in injury to healthcare workers who push, pull, or lift the patient's body weight. For healthcare workers, the most prevalent cause of injuries resulting in days away from work is overexertion or bodily reaction, which includes motions such as lifting, bending, or reaching and is often related to patient handling. These injuries can be sudden and traumatic, but are more often cumulative in nature, resulting in gradually increasing symptoms and disability in the healthcare worker.

In recognition of the risk and frequency of healthcare worker injuries associated with patient handling, safe patient handling procedures and/or protocols are often implemented in the healthcare setting. These protocols stress that methods for moving patients should incorporate a form of assistive device to reduce the effort required to handle the patient, thus minimizing the potential for injury to healthcare workers. Such assistance may be accomplished, for example, with the use of low-friction sheets or air assisted patient transfer devices that utilize forced air to reduce the physical exertion needed from healthcare workers to accomplish the task of moving a patient.

The present disclosure seeks to overcome certain of these limitations and other drawbacks of existing devices, systems, and methods, and to provide new features not heretofore available.

SUMMARY

The following presents a general summary of aspects of the invention in order to provide a basic understanding of the invention. This summary is not an extensive overview of the invention. It is not intended to identify key or critical elements of the invention or to delineate the scope of the invention. The following summary merely presents some concepts of the invention in a general form as a prelude to the more detailed description provided below.

Aspects of the present disclosure relate to a system for use with a bed having a frame and a supporting surface supported by the frame, which includes an inflatable patient support device. The device includes a top sheet and a bottom sheet, where the top sheet is connected to the bottom sheet to define a cavity configured to be inflated, such that the top sheet forms a top wall of the cavity in use, and the bottom sheet forms a bottom wall of the cavity in use. The device further has a plurality of passages extending from the cavity to an exterior of the device, through the bottom sheet, and a plurality of gussets connected to the top sheet and the bottom sheet and extending across the cavity. The passages are configured to permit air to pass from the cavity to the exterior of the device and to flow between a bottom surface of the device and a supporting surface upon which the device is configured to rest. This airflow reduces friction between the device and the surface on which the device rests. The gussets may serve to limit inflation of the device and at least partially define the shape and contour of the device when inflated.

According to one aspect, the device further includes a port in communication with the cavity and with the exterior of the device, configured for connection to an air output (e.g., an air pump) for inflation of the cavity. The port may include an opening configured to receive a portion of the air output and a retaining mechanism configured to retain the portion of the air output within the opening.

According to another aspect, the device further includes a piece of a directional stitching material connected to the bottom surface of the device and positioned to cover at least one of the passages. The directional stitching material is air-permeable to allow air passing through the passage to escape to the exterior of the device. In one configuration, the directional stitching material is oriented to resist sliding of the device with respect to the supporting surface toward a head edge or a foot edge of the device.

According to a further aspect, the device further includes a piece of air-permeable material connected to the bottom surface of the device and positioned to cover at least one of the passages, and wherein the piece of air-permeable material is configured to allow air passing through the passage(s) to escape to the exterior of the device. In one configuration, the piece of air-permeable material may have directional friction properties, e.g., being configured to provide greater resistance to sliding of the device with respect to the supporting surface in at least one direction as compared to at least one other direction.

According to yet another aspect, the top sheet forms the top wall of the cavity and a top surface of the device, and the bottom sheet forms the bottom wall of the cavity and the bottom surface of the device. The top sheet and the bottom sheet may be formed of a single piece that folded over at one edge, or formed as separate pieces which are joined together around their edges, among other configurations.

According to a still further aspect, the top sheet has a high friction material on a top surface thereof, wherein the high friction material has a greater resistance to sliding than a material of the bottom sheet.

According to an additional aspect, the system includes the device and further includes a wedge comprising a wedge body having a base wall, a ramp surface, and a back wall, with the ramp surface and the base wall forming an apex at a front end of the wedge. The wedge is configured to be positioned under the device such that the base wall confronts the supporting surface and the ramp surface confronts the bottom surface of the device. The system may include multiple such wedges, and in one embodiment, two wedges are included.

Additional aspects of the disclosure relate to a system as described above, with an inflatable device that includes a top sheet and a bottom sheet, where the top sheet is connected to the bottom sheet to define a cavity configured to be inflated, such that the top sheet forms a top wall of the cavity in use, and the bottom sheet forms a bottom wall of the cavity in use. The device also includes a plurality of passages extending from the cavity to an exterior of the device, through the bottom sheet, and a piece of air-permeable material connected to the bottom surface of the device and positioned to cover at least one of the passages. The passages are configured to permit air to pass from the cavity to the exterior of the device and to flow between a bottom surface of the device and a supporting surface upon which the device is configured to rest. The piece of air-permeable material is configured to allow air passing through the passage(s) to escape to the exterior of the device. The device/system may also include any of the additional components and/or configurations described above.

According to one aspect, the device further includes a port in communication with the cavity and with the exterior of the device, configured for connection to an air output for inflation of the cavity.

According to another aspect, the air-permeable material is a directional stitching material configured to have a greater resistance to sliding in at least one direction as compared to at least one other direction. In one configuration, the directional stitching material may be oriented to resist sliding of the device with respect to the supporting surface toward a head edge or a foot edge of the device.

According to a further aspect, the device includes a plurality of pieces of air-permeable material, each connected to the bottom surface of the device and positioned to cover at least one of the passages. Each piece of air-permeable material is configured to allow air passing through the passage(s) to escape to the exterior of the device. In one configuration, each piece of the air-permeable material is a directional stitching material as described above.

According to yet another aspect, the top sheet has a high friction material on a top surface thereof, where the high friction material has a greater resistance to sliding than a material of the bottom sheet.

Further aspects of the disclosure relate to a system as described above, with an inflatable device that includes a top sheet and a bottom sheet, where the top sheet is connected to the bottom sheet to define a cavity configured to be inflated, such that the top sheet forms a top wall of the cavity in use, and the bottom sheet forms a bottom wall of the cavity in use. The device also includes a plurality of passages extending from the cavity to an exterior of the device, through the bottom sheet, where the passages are configured to permit air to pass from the cavity to the exterior of the device and to flow between a bottom surface of the device and a supporting surface upon which the device is configured to rest. The device further includes a port in communication with the cavity and with the exterior of the device, configured for connection to an air output for inflation of the cavity, and a valve located within the cavity, between the top and bottom sheets, wherein the valve is in communication with the port and the cavity. The valve includes a pocket located between the top and bottom sheets, the pocket having an entrance opening in communication with the port to receive air from the port and an exit opening in communication with the cavity. The exit opening is spaced from the entrance opening, such that airflow through the port is configured to pass through the valve by flowing from the port into the entrance opening, through the pocket, and out through the exit opening, to enter the cavity. The device/system may also include any of the additional components and/or configurations described above.

According to one aspect, the port further includes an opening configured to receive a portion of the air output and a retaining mechanism configured to retain the portion of the air output within the opening. In some aspects, the retaining mechanism is an elastic member that is adjustable to adjust the port opening.

According to another aspect, the device further includes a piece of a directional stitching material connected to the bottom surface of the device and positioned to cover at least one of the passages, where the directional stitching material is air-permeable to allow air passing through the passage(s) to escape to the exterior of the device.

According to a further aspect, the top sheet has a high friction material on a top surface thereof, wherein the high friction material has a greater resistance to sliding than a material of the bottom sheet.

According to a further aspect, a port sock includes a first open end and a second open end configured to connect to an air output (e.g., an air pump) at the second open end. The first end has a first opening configured to be couple with the inflatable body and in fluid communication with the cavity of the device, and the second end has a second opening including the port configured to connect to the air output. In one aspect, the second opening has retaining mechanism configured to hold the shape of the second opening such as an elastic member. The port sock also includes side pockets configured to receive an oblong lip of a nozzle connected to the air output. The oblong lip may be a C-shaped clip configured to attach to an existing lip of a nozzle. The oblong lip may have a shape where one axis is longer than the other. The oblong lip may be substantially symmetrical. The port sock further includes side handles configured to stretch the retaining mechanism of the second opening such that the size of the second opening is adjustable. In some aspects, the C-shaped clip is removable. In still other aspects, the C-shaped clip is manufactured as a single, unitary component with the nozzle forming the oblong lip.

Still further aspects of the disclosure relate to a system as described above, with an inflatable device that includes a top sheet and a bottom sheet, where the top sheet is connected to the bottom sheet to define a cavity configured to be inflated, such that the top sheet forms a top wall of the cavity in use, and the bottom sheet forms a bottom wall of the cavity in use, as well as a port in communication with the cavity and with the exterior of the device, configured for connection to an air output for inflation of the cavity. The device also includes a plurality of passages extending from the cavity to an exterior of the device, through the bottom sheet, where the passages are configured to permit air to pass from the cavity to the exterior of the device and to flow between a bottom surface of the device and a supporting surface upon which the device is configured to rest. The device further includes a piece of air-permeable material connected to the bottom surface of the device and positioned to cover at least one of the passages, where the piece of air-permeable material is configured to allow air passing through the passage(s) to escape to the exterior of the device. The system also includes a wedge including a wedge body having a base wall, a ramp surface, and a back wall, with the ramp surface and the base wall forming an apex at the front end of the wedge. The wedge is configured to be positioned under the device such that the base wall confronts the supporting surface and the ramp surface confronts the bottom surface of the device. The system may further include multiple such wedges, and in one embodiment, two wedges are included. The device/system may also include any of the additional components and/or configurations described above.

According to one aspect, the air-permeable material is a directional stitching material configured to have a greater resistance to sliding in at least one direction as compared to at least one other direction. In one configuration, the ramp surface of the wedge has a ramp engagement member, and the wedge is configured to be positioned under the device such that the ramp engagement member engages the piece of air-permeable material to create a directional gliding assembly configured to have a greater resistance to sliding between the ramp engagement member and the piece of air-permeable material that is greater in a first direction extending parallel to the front end of the wedge and smaller in a second direction extending from the front end toward the back wall of the wedge. The directional gliding assembly may further be configured to have a greater resistance to sliding between the ramp engagement member and the piece of air-permeable material that is greater in a third direction extending from the back wall toward the front end of the wedge and smaller in the second direction. It is understood that the ramp engagement member may include multiple different engagement members with resistances to sliding in different directions in one embodiment.

According to another aspect, the device further includes a plurality of gussets connected to the top sheet and the bottom sheet and extending across the cavity.

According to a further aspect, the system further includes an absorbent body pad configured to be placed in contact with the top surface of the device, such that the body pad rests beneath a patient lying on the device.

According to yet another aspect, the system further includes an air pump having an air output configured for connection to the port for inflation of the device. The pump may have an attachment mechanism configured for attaching the pump to a structure. For example, the attachment mechanism may be a T-shaped bar that is connected to the pump by a hinge and has two arms with hooks at the ends thereof for hanging the pump from a structure such as a bed rail.

Other aspects of the disclosure relate to a method for use with a system as described herein and/or individual components of such systems, such as the inflatable device, wedges, etc. For example, the method may include placing an inflatable device as described herein above a supporting surface of a bed and beneath a patient positioned on the bed, and inflating the device, such as by using an air pump as described above. According to one aspect, the method may also include using the device to move the patient on the bed, or from the bed to another surface. An absorbent body pad may also be placed between the patient and the device.

According to another aspect, the method may include inserting a wedge or wedges as described herein beneath the device and beneath the patient by moving the wedge away from a side edge of the bed and toward and under the patient. After insertion, the ramp surface of the wedge supports the patient in an angled position. The ramp surface of the wedge may have an engagement member that engages the bottom surface of the device (e.g., another engagement member on the device) to form a selective gliding assembly that resists movement of the device in a first direction away from the side edge of the bed and/or from the back wall toward the front end of the wedge, and permits movement of the device in a second direction toward the side edge of the bed and/or from the front end toward the back wall, such that a first pull force necessary to create sliding movement of the wedge in the first direction is greater compared to a second pull force necessary to create sliding movement of the wedge in the second direction. This permits the wedge to be inserted underneath the device, but resists the device sliding down the ramp surface of the wedge. Additionally or alternately, the base wall of the wedge may have an engagement member that engages a surface of the bed to form a selective gliding assembly that resists movement of the wedge with respect to the surface of the bed in a first direction away from the patient and toward the side edge of the bed, and permits movement of the wedge with respect to the surface of the bed in a second direction from the side edge of the bed toward the patient to ease insertion of the wedge beneath the device, such that a first pull force necessary to create sliding movement of the wedge in the first direction is greater compared to a second pull force necessary to create sliding movement of the wedge in the second direction. The device (along with the patient) may be pulled slightly toward the side edge of the bed to properly position the patient after insertion of the wedge.

Another method for use with a system as described herein and/or individual components of such systems, such as the inflatable device, wedges, etc. may include placing above a supporting surface an inflatable device comprising an inflatable body formed by a top sheet and a bottom sheet disposed in connection with the top sheet to form a cavity having the top sheet as a top wall and the bottom sheet as a bottom wall, and at least one port having a port opening in fluid communication with the cavity and configured to provide an air input for air for inflating the cavity, wherein the at least one port comprises an elastic member for adjusting a size of the port opening. The method may further include placing a patient above the inflatable device, adjusting the port opening to receive a nozzle of an air pump, and inflating the device using the air pump. The method may further include using the device to change a position of the patient on the support surface.

Other features and advantages of the invention will be apparent from the following description taken in conjunction with the attached drawings.

BRIEF DESCRIPTION OF THE DRAWINGS

To understand the present invention, it will now be described by way of example, with reference to the accompanying drawings in which.

DETAILED DESCRIPTION

Figure 1:
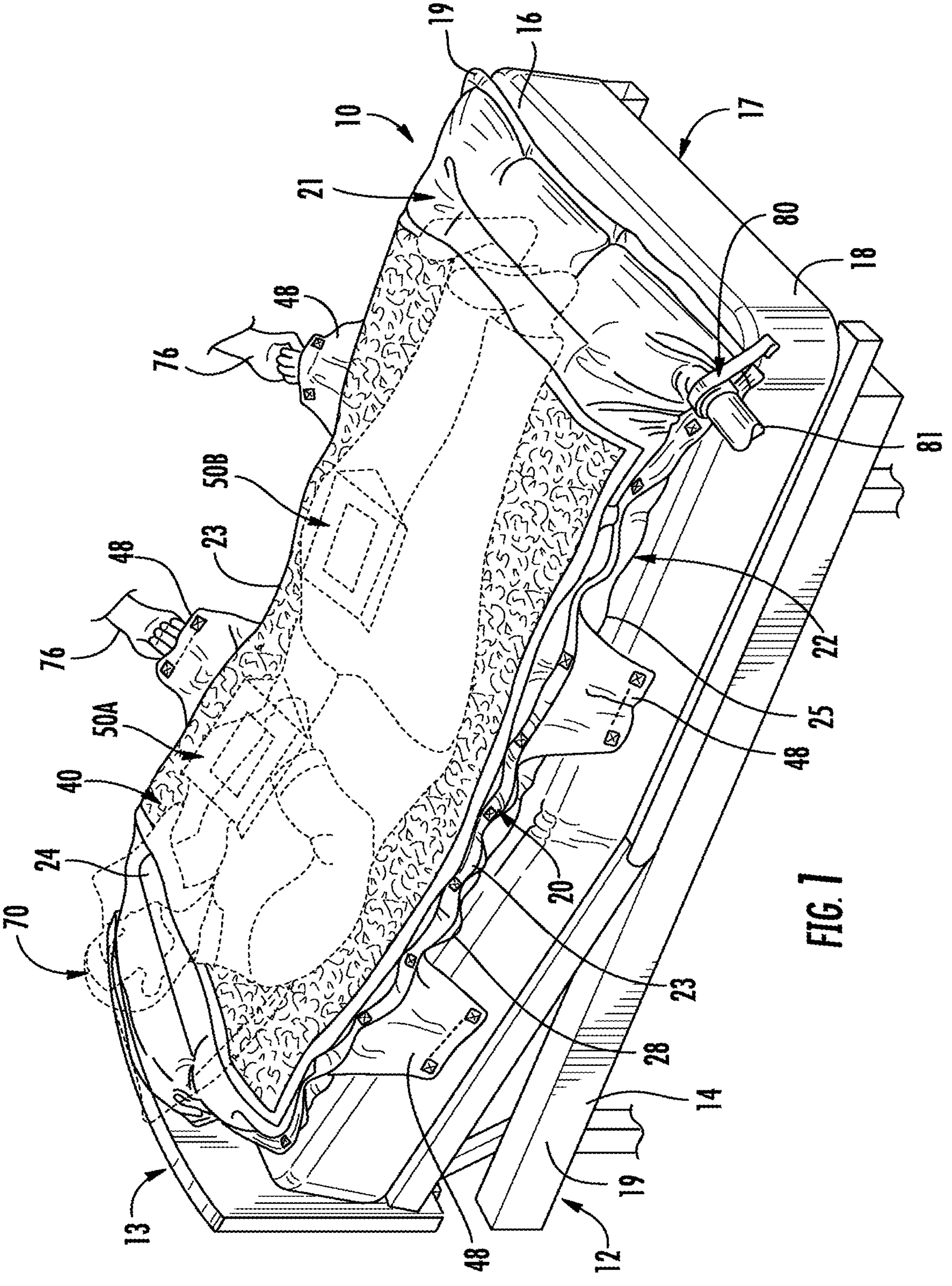
FIG. 1 is a perspective view of one embodiment of a system for use in turning and positioning a patient, according to aspects of the disclosure, with a patient shown in broken lines.

While this invention is capable of embodiment in many different forms, there are shown in the drawings, and will herein be described in detail, certain embodiments of the invention with the understanding that the present disclosure is to be considered as an example of the principles of the invention and is not intended to limit the broad aspects of the invention to the embodiments illustrated and described.

In general, the disclosure relates to a system or apparatus, including an inflatable patient support device, an absorbent body pad configured to be placed over the device, and one or more wedges configured to be placed underneath the device to support the patient in various positions, where the wedge(s) and the device form one or more selective gliding assemblies, as well as systems including one or more of such devices and methods utilizing one or more of such systems and/or devices. Various embodiments of the invention are described below.

Referring now to the figures, and initially to FIGS. 1-6, there is shown an example embodiment of a system 10 for use in turning and positioning a person resting on a surface, such as a patient lying on a hospital bed. As shown in FIG. 1, the system 10 includes an inflatable patient support device (hereinafter, “device”) 20, an absorbent body pad 40 configured to be placed over the device 20, and one or more wedges 50 configured to be placed under the device 20. The patient can be positioned on top of the body pad 40, with the body pad 40 lying on the device 20, and one or more wedges 50A,B optionally positioned underneath the device 20.

Figure 2:
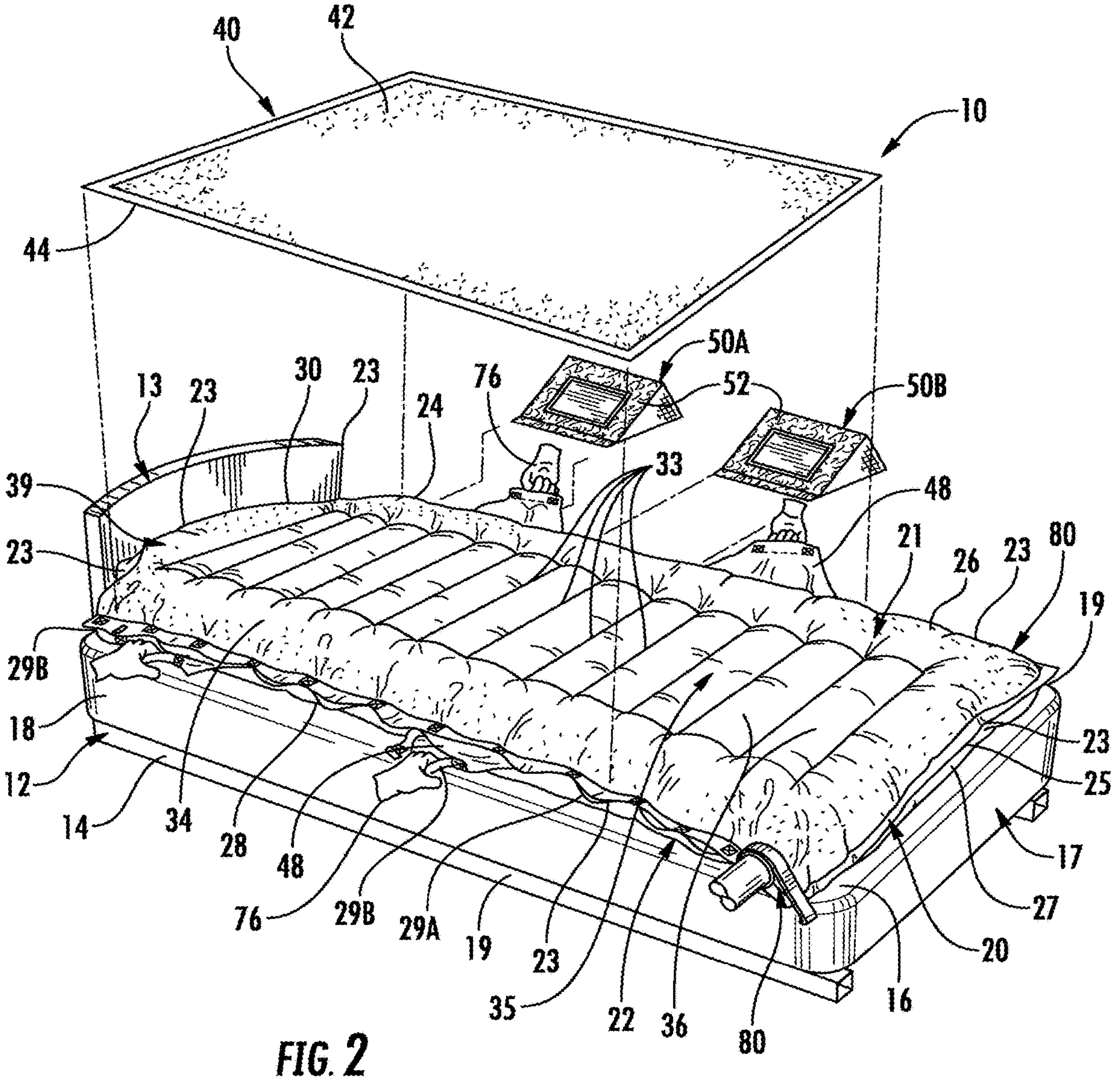
FIG. 2 is a partially-exploded perspective view of the system of FIG. 1.
Figure 4:
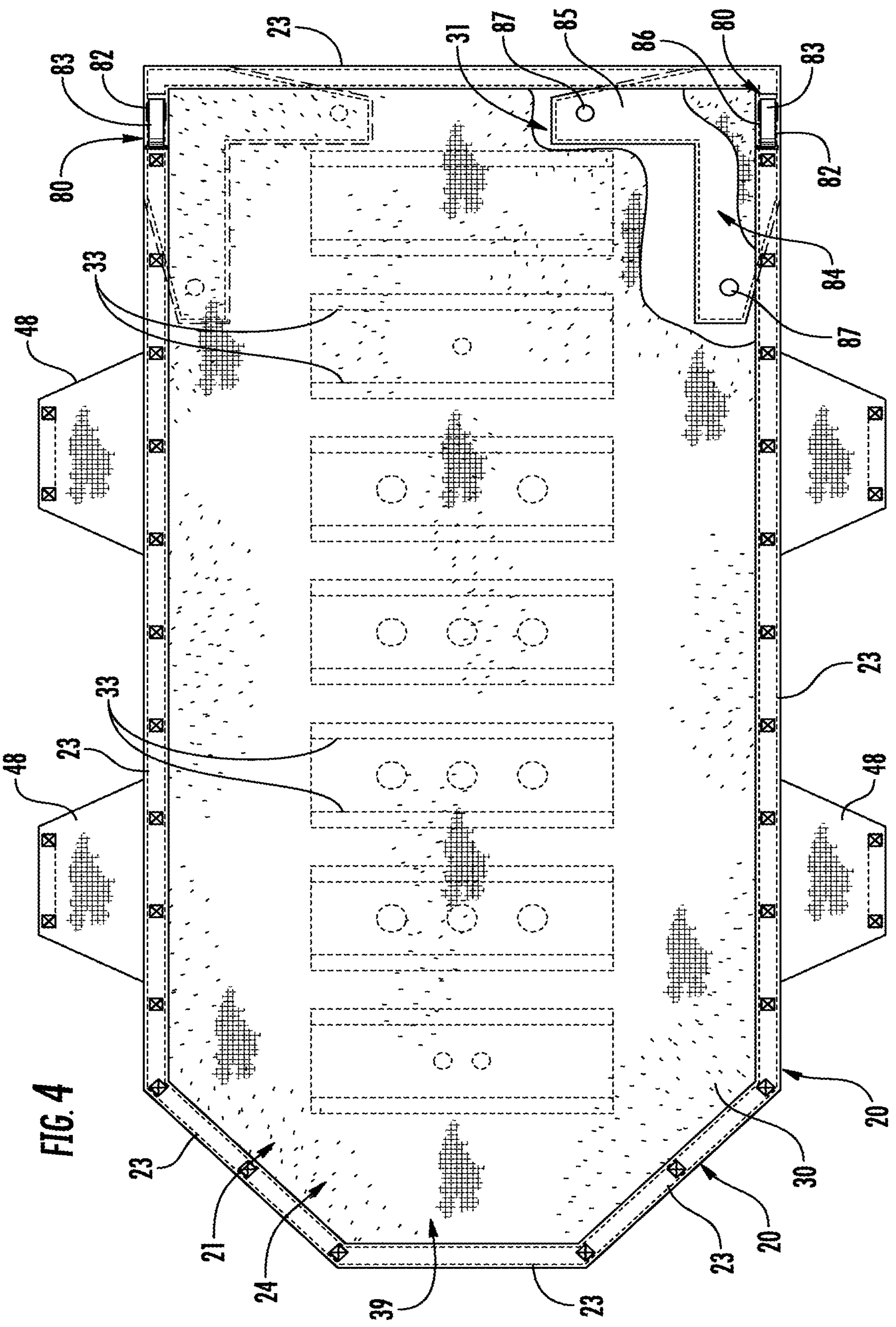
FIG. 4 is a partially-broken away top elevation view of the inflatable device of FIG. 3, with some internal detail shown in broken lines.
Figure 5:
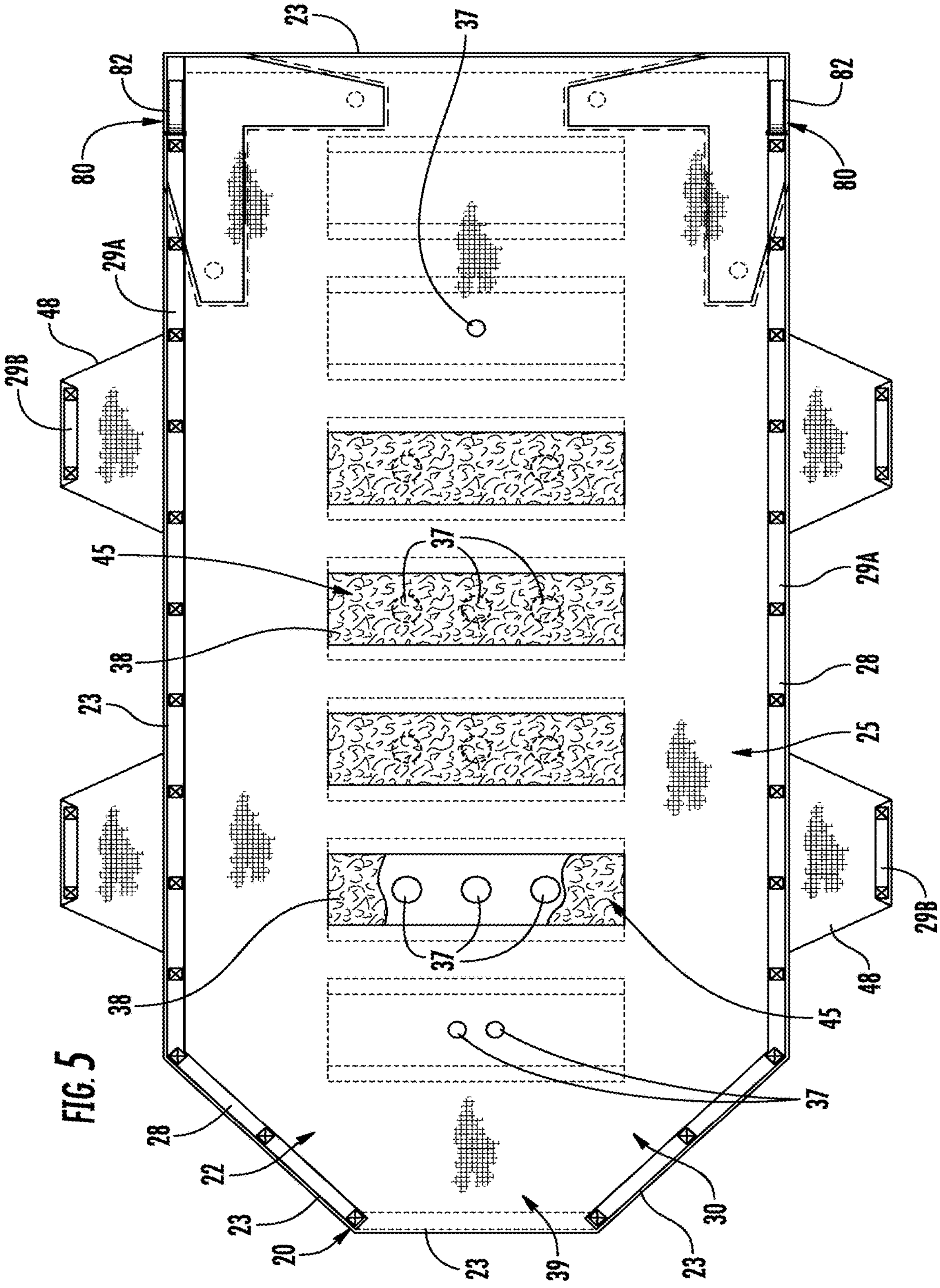
FIG. 5 is a bottom elevation view of the inflatable device of FIG. 3, with some internal detail shown in broken lines.
Figure 6:
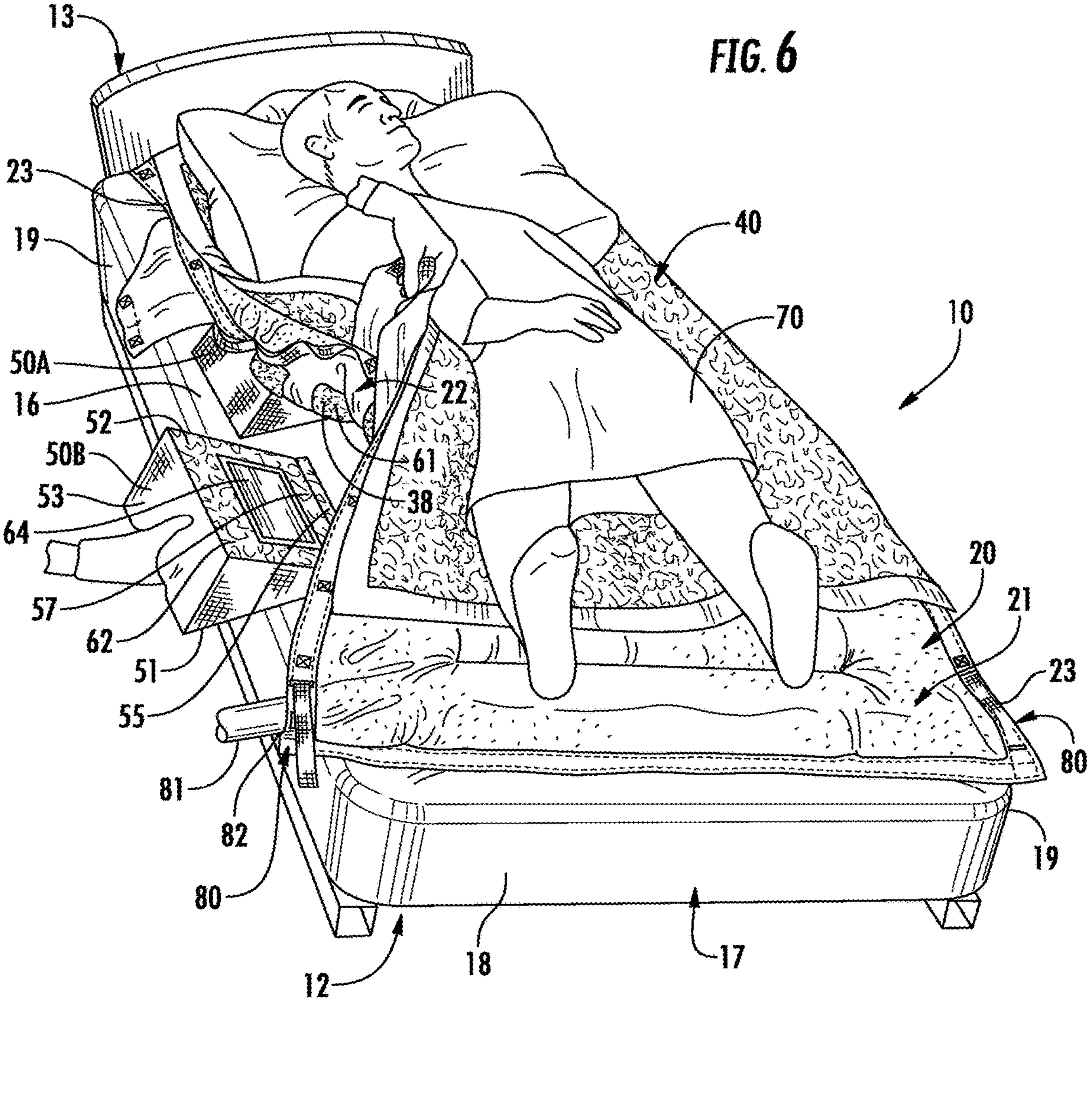
FIG. 6 is a perspective view of a caregiver inserting wedges of the system of FIG. 1 underneath the inflatable device of FIGS. 1-5.

As shown in FIGS. 1-6, the system 10 is configured to be placed on a bed 12 or other support apparatus for supporting a person in a supine position. The bed 12 generally includes a frame 14 and a supporting surface 16 supported by the frame 14, as shown in FIGS. 1-2 and 6, and has a head 13, a foot 17 opposite the head 13, and opposed sides or edges 19 extending between the head 13 and the foot 17. The supporting surface 16 can be provided by a mattress 18 or similar structure, and in various embodiments, the mattress 18 can incorporate air pressure support, alternating air pressure support and/or low-air-loss (LAL) technology. These technologies are known in the art, and utilize a pump motor or motors (not shown) to effectuate airflow into, over and/or through the mattress 18. For beds having LAL technology, the top of the mattress 18 may be breathable so that the airflow can pull heat and moisture vapor away from the patient. The bed 12 may also include one or more bed sheets (such as a fitted sheet or flat sheet), as well as pillows, blankets, additional sheets, and other components known in the art. Further, the bed 12 may be an adjustable bed, such as a typical hospital-type bed, where the head 13 (or other parts) of the bed 12 can be raised and lowered, such as to incline the patient’s upper body. It is understood that the system 10 and the components thereof can be used with other types of beds 12 as well.

In example embodiments described herein, the system 10 has one or more selective gliding assemblies 60 positioned between components of the system 10 to permit sliding of the components relative to each other in certain directions and to resist sliding of the components relative to each other in at least one direction. The selective gliding assemblies 60 are formed by one or more directionally-oriented engagement members positioned between the components and configured to engage the components to permit and limit sliding in specified directions. In general, these directionally-oriented engagement members are configured to have a resistance to sliding in at least one direction that is greater than their resistance to sliding in at least one other direction.

Figure 19:
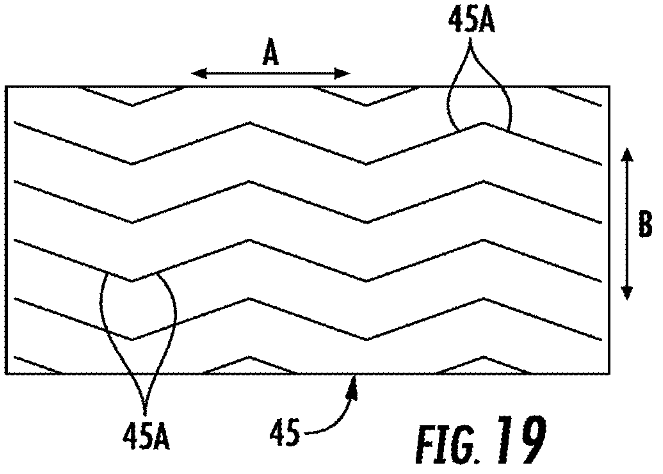
FIG. 19 is a schematic plan view of one engagement member of a selective glide assembly of the system of FIG. 1.
Figure 20:
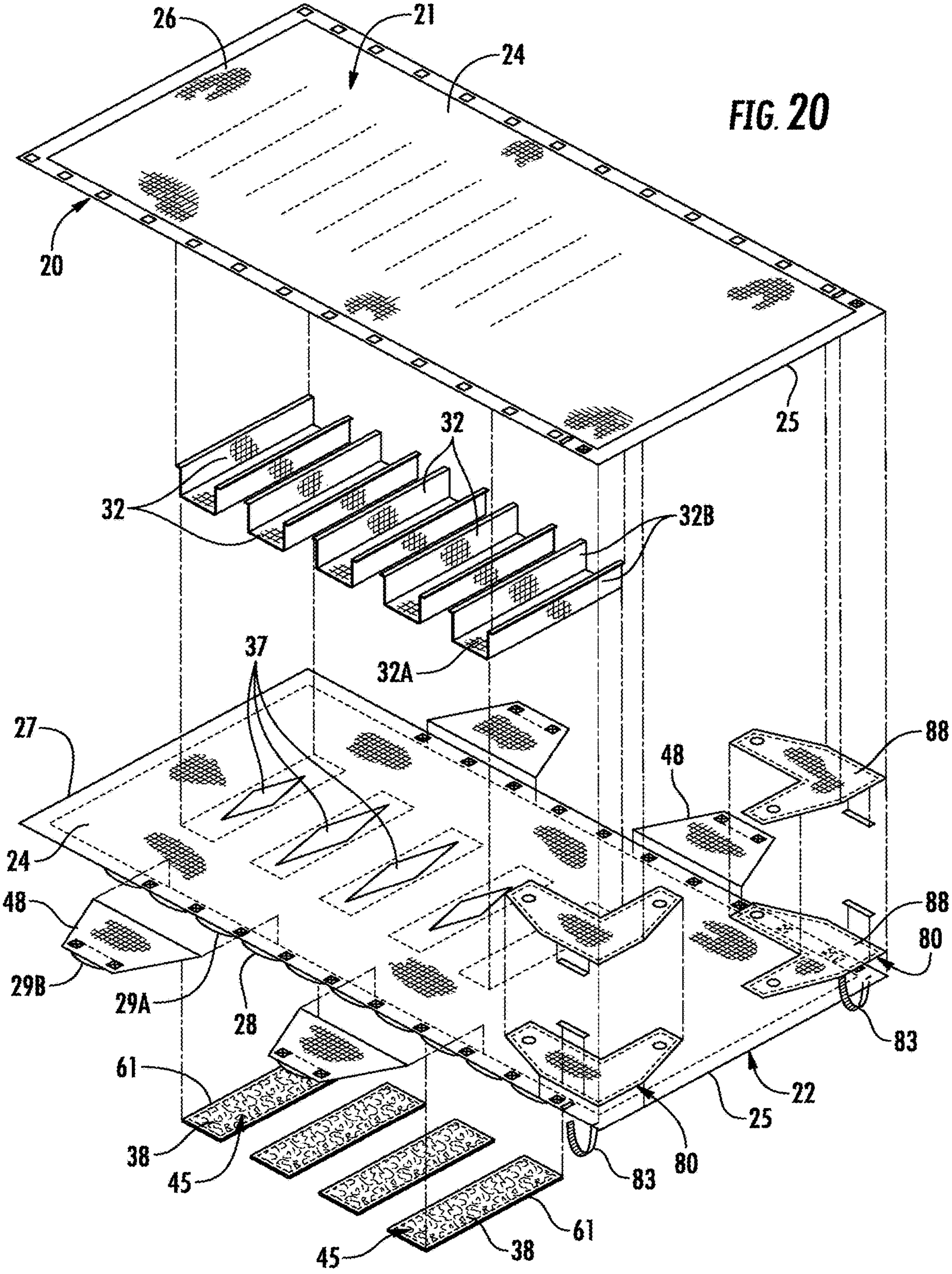
FIG. 20 is an exploded perspective view of another embodiment of a device for use with a system for turning and positioning a patient, according to aspects of the disclosure.
Figure 21:
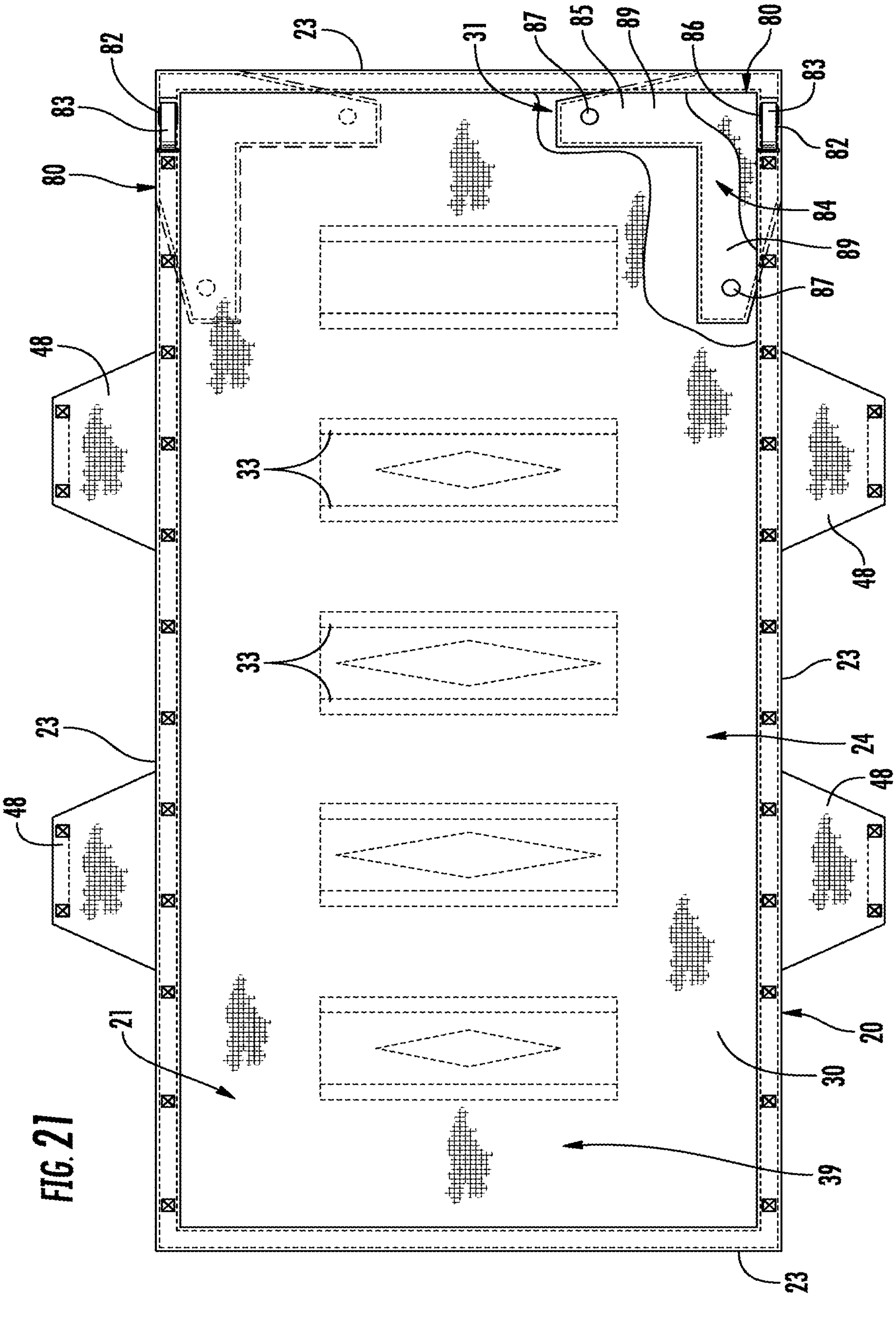
FIG. 21 is a top view of the device of FIG. 20.
Figure 22:
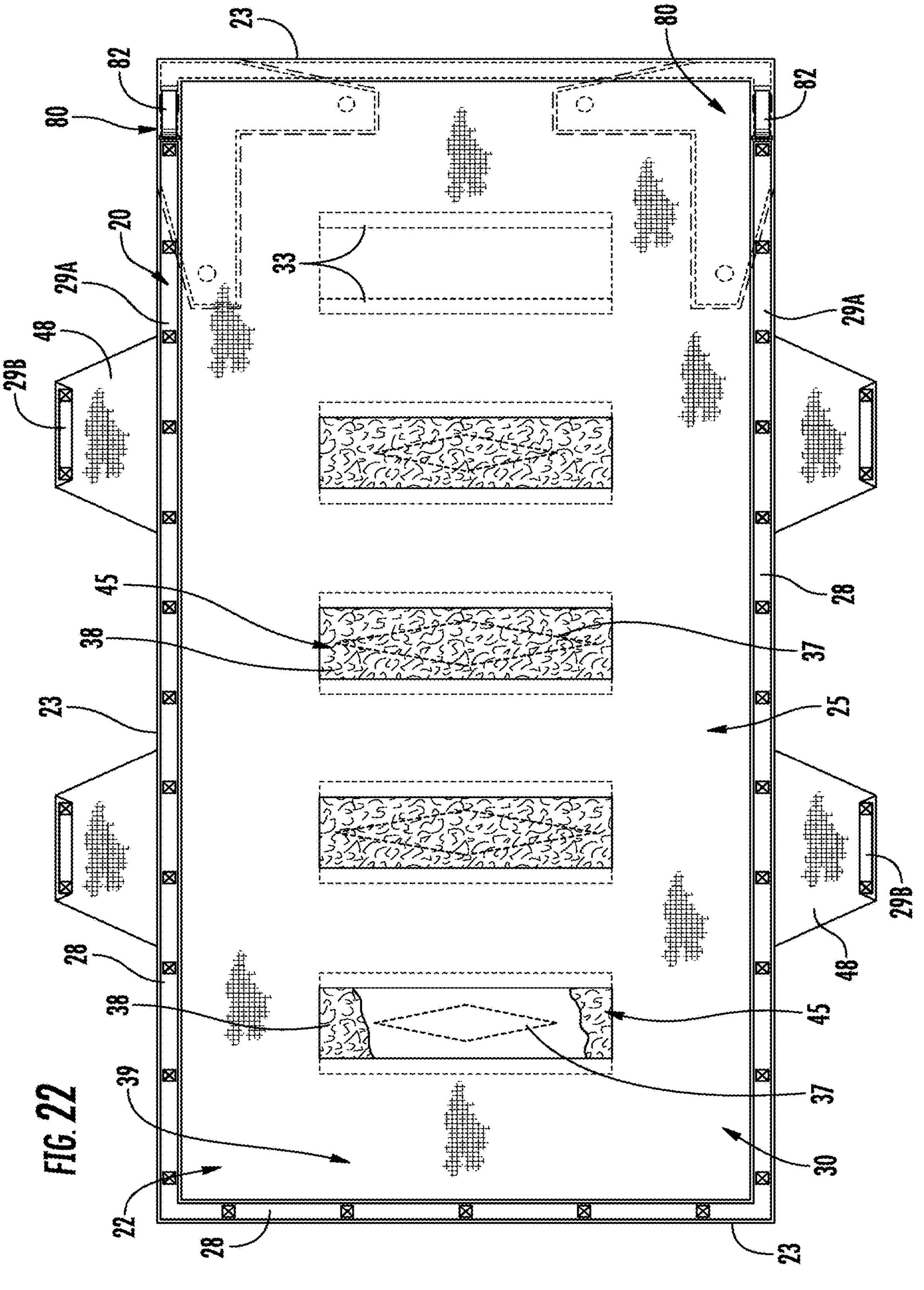
FIG. 22 is a bottom view of the device of FIG. 20.

One type of engagement member that is usable in connection with the apparatus 10 is a stitched material 45 with a directional stitching pattern that extends along a particular direction, such as a herringbone or zig-zag stitching pattern (see FIG. 19), to assist in allowing the engagement member to glide along one axis and to resist gliding along another axis. As seen in FIG. 19, the herringbone stitching pattern shown is relatively open, with links 45A forming angles of 90° or greater, such that each link 45A in the stitching pattern extends a greater distance along axis A than along axis B. In one embodiment, the links 45A may form angles of approximately 120°, approximately 110°-180° (straight line), or 90° or greater with respect to each other. Other directional stitching patterns may be utilized, including other directional stitching patterns with links 45A that are oriented and/or sized differently. In one example, the engagement member 62 may have stitching in the form of a plurality of parallel or substantially parallel lines extending generally in a single direction. The directional stitching material 45 as shown in FIG. 19 permits sliding in directions generally along the axis A, or in other words, along the directions in which the stitching pattern extends. The directional stitching material 45 as shown in FIG. 19 resists sliding in directions generally along the axis B, or in other words, across the stitches and/or transverse to the directions in which the stitching pattern extends.

One example of a stitched material usable as the directional stitching material 45 is a loop material (e.g. as used in a hook-and-loop connection), with a directional stitching pattern located on the reverse side of the loop material. This loop material may be connected to a component of the system 10 with the loop side facing inward and the reverse side facing outward to form the surface of the engagement member. The directional stitching material 45 may be formed of a different material in another embodiment, including, without limitation, a variety of different fabric materials. It is understood that such materials may include a directional stitching pattern. The directional stitching material 45 may be connected to a component of the system 10 in a surface-to-surface, confronting relation to form a layered structure in one embodiment, such as by stitching, adhesive, sonic welding, heat welding and other techniques, including techniques familiar to those skilled in the art.

As used in some embodiments described herein, two pieces of a directional stitching material 45, such as shown in FIG. 19, can be used in engagement with each other, with the axes A and B of the stitching patterns of the two pieces in alignment, to provide increased resistance to sliding along the axis B. The two pieces of directional stitching material 45 may be the same type of material or different types of material in various embodiments, and may have the same or different stitching patterns. This directional stitching material 45 may also be used in connection with other directionally-oriented engagement members to achieve increased resistance to sliding in selected directions. In various uses, the directional stitching material 45 may have a directional stitching pattern that extends primarily in the lateral or width direction of the system 10 (i.e. between side edges 23), or primarily in the longitudinal or length direction of the system 10 (i.e. between the front edge 23 and rear edge 23).

Other materials having directionally oriented textures, patterns, etc., extending in a specified direction may be usable in connection with the apparatus 10 as engagement members. For example, such a material may have a ridged or other textured structure. The directionally oriented texture may have a shape and/or orientation that is similar to one of the embodiments of the directional stitching patterns described above. Such a textured structure may be created by various techniques, including weaving, texturing (e.g. physical deformation), or application of a substance such as by printing, deposition, etc., among other techniques. Such other materials may function in the same manner as the directional stitching material 45 discussed above.

Another type of engagement member that is usable in connection with the system 10 is a directional glide material, such as a brushed fiber material or other brushed fabric material, which may have fibers that lie facing a specific direction. In general, a directional glide material resists gliding in a single direction and permits relatively free gliding in the opposite direction and along an axis perpendicular to the single direction of resistance, such that the resistance to gliding in the single direction is significantly higher than any of these three other directions identified. Additionally, a directional glide material may have structural characteristics to create this resistance and freedom for gliding in specific directions, such as structural elements that are directionally oriented. For example, the directional glide material may include projecting structures, e.g., ridges, fibers, bristles, etc., that extend non-perpendicularly from the surface of a substrate, a majority or substantial entirety of which are oriented (e.g., angled, curved, etc.) in the same general direction. One embodiment of an engagement member made of a directional glide material may be a brushed nylon fiber material (e.g. lint brush material) with about 44-48 wales per inch and about 54-58 courses per inch in one embodiment. Another type of directional glide material may be used in other embodiments, including various ridged fabric and non-fabric materials, such as a flexible ratchet material as used in a zip-tie. The directional glide material may be connected to a component of the system 10 in a surface-to-surface, confronting relation to form a layered structure in one embodiment, such as by stitching, adhesive, sonic welding, heat welding and other techniques, including techniques familiar to those skilled in the art. This directional glide material can be used in connection with a directional stitching material 45 as shown in FIG. 19 to create a selective gliding assembly 60 with a "one-way" glide arrangement. This can be done by engaging the directional glide material with the directional stitching material, with the single direction of resistance of the directional glide material being aligned with the axis along which the stitching pattern extends. This arrangement allows the engagement members to glide with the grain of the directional glide material, while resisting gliding in other directions, including the opposite direction along the same axis as the gliding direction (i.e., along one of directions A in FIG. 18 or 19).

As described herein with respect to the embodiment of FIGS. 1-6, the system may use selective gliding assemblies 60 to create directional gliding between the wedges 50 and the underside of the device 20 and/or between the wedges 50 and the bed 12. These selective gliding assemblies 60 may include one or more pieces of directional stitching material 45 and/or one or more pieces of directional glide material 49, as illustrated schematically in FIG. 18 and described in greater detail elsewhere herein. In other embodiments, selective gliding assemblies 60 may be used to create directional gliding between one or more of the above sets of components and/or between one or more other components of the system 10.

An example embodiment of the inflatable patient support device 20 is shown in greater detail in FIGS. 1-6. In general, the device 20 is flexible and foldable when in the non-inflated state (e.g., FIGS. 4-5), and has a top surface 21 and a bottom surface 22 defined by a plurality of peripheral edges 23. The device 20 is configured to be positioned on the bed 12 so that the bottom surface 22 is above the supporting surface 16 of the bed 12 and faces or confronts the supporting surface 16, and is supported by the supporting surface 16. As used herein, "above," "below," "over," and "under" do not imply direct contact or engagement. For example, the bottom surface 22 being above the supporting surface 16 means that that the bottom surface 22 may be in contact with the supporting surface 16, or may face or confront the supporting surface 16 and/or be supported by the supporting surface 16 with one or more structures located between the bottom surface 22 and the supporting surface 16, such as a bed sheet as described above. Likewise, "facing" or "confronting" does not imply direct contact or engagement, and may include one or more structures located between the surface and the structure it is confronting or facing.

Figure 3:
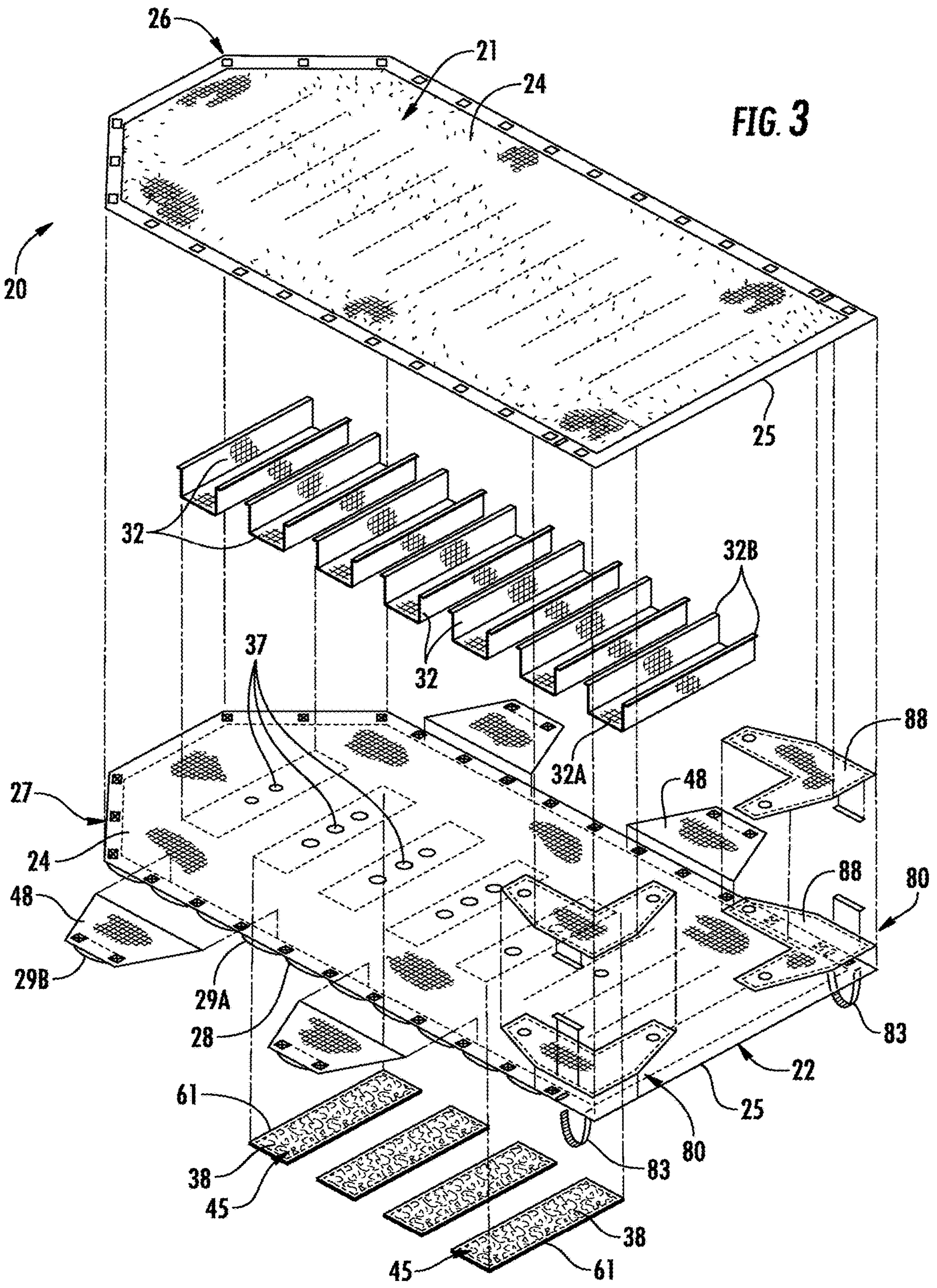
FIG. 3 is an exploded perspective view of one embodiment of an inflatable device of the system of FIG. 1.

As seen in FIGS. 3-5, the device 20 in this embodiment is an irregular hexagonal shape, having a rectangular main body portion with three peripheral edges 23 and a narrowed or tapering head portion 39 with three additional peripheral edges 23. The shape of the device 20 may be different in other embodiments, including a rectangular shape. The device 20 generally includes an inflatable body 30 that includes an internal cavity 31 configured to be inflated with air or another gaseous substance. The inflatable body 30 is defined by at least a top sheet 26 forming a top wall of the cavity 31 and a bottom sheet 27 forming a bottom wall of the cavity 31, with the top sheet 26 and the bottom sheet 27 connected together to define the cavity 31 between them. In the embodiment shown in FIGS. 1-6 and 12-13, the top and bottom sheets 26, 27 are two separate pieces of sheet material that are connected together around their peripheries, such as by stitching and/or adhesives, or one or more other connection techniques described herein. In other embodiments, the top and bottom sheets 26, 27 may be made from a single piece of material that is folded over and connected by stitching along the free ends or that is formed in a loop, or the top and/or bottom sheets 26, 27 may be formed of multiple pieces. Both the top and bottom sheets 26, 27 may be formed of the same material in one embodiment, although these components may be formed of different materials in another embodiment. It is understood that either or both of the sheets 26, 27 may have a single layer or multiple layers that may be formed of the same or different materials.

Additionally, the sheet material(s) of the top and bottom sheets 26, 27 may have properties that are desirable for a particular application. For example, the sheets 26, 27 may be breathable fabrics or other materials that have sufficient resistance to air passage to retain inflation of the inflatable body 30, while maintaining sufficient breathability to allow passage of heat and moisture vapor away from the patient, thereby enabling the device 20 to be left beneath a patient indefinitely. Such a device 20 may be used in a complementary manner with low air-loss beds, as mentioned above. The material(s) of the top and bottom sheets 26, 27 may also include specific frictional properties, as described herein. Additionally, the material of the top and bottom sheets 26, 27 may have greater permeability to water vapor (i.e., breathability) than its permeability to liquid or air. For example, the top and/or bottom sheets 26, 27 may be formed of a material that is liquid repellant and/or impermeable and may have little to no air permeability, while being permeable to moisture vapor. In one embodiment, the top and bottom sheets 26, 27 may be formed of polyester and/or nylon (polyamide), for example, a coated nylon taffeta material, which can provide these properties. The coating on the sheets 26, 27 has a higher coefficient of friction than the sheet material itself, creating a configuration with a high-friction material 24 (the coating) on one surface and a low-friction material 25 (the sheet material) on the opposite side, as described in greater detail elsewhere herein.

Figure 25:
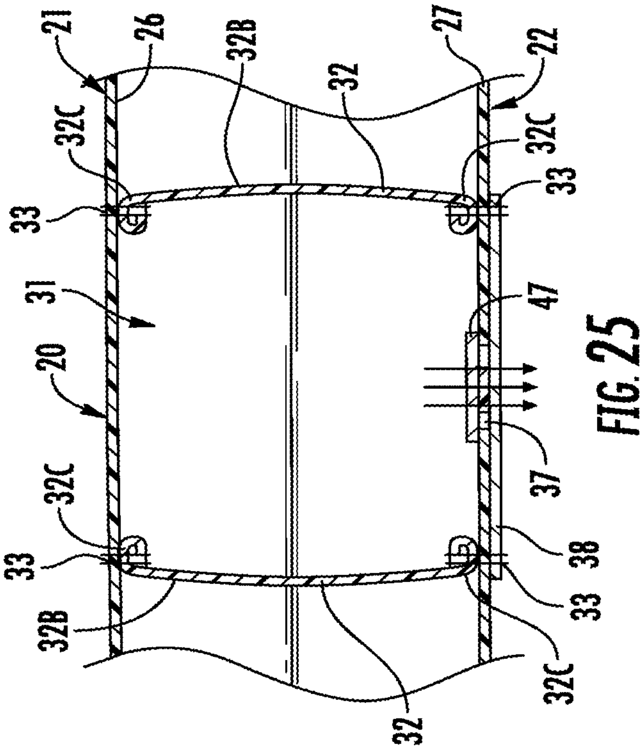
FIG. 25 is a magnified cross-section view of another embodiment of a device for use with a system for turning and positioning a patient, according to aspects of the disclosure.
Figure 24:
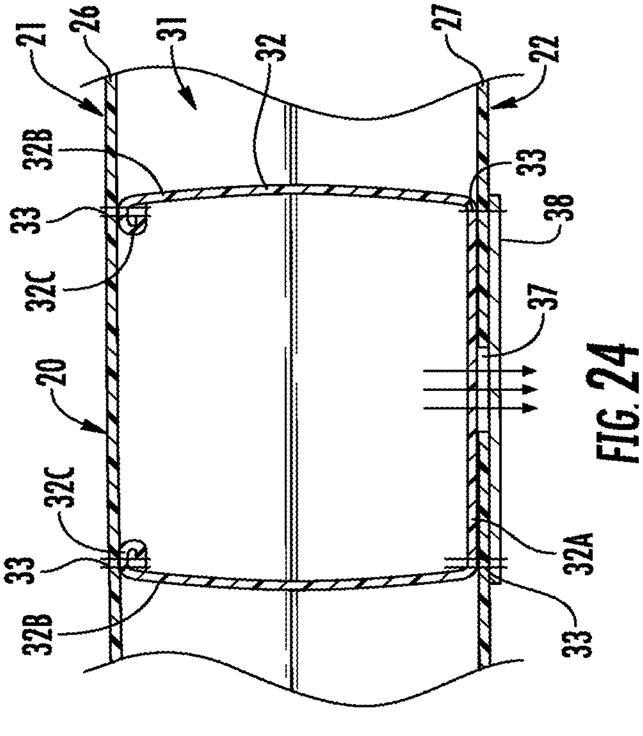
FIG. 24 is a magnified portion of the cross-section view of FIG. 23.

The inflatable body 30 of the device 20 may include one or more inflation-limiting members to create a specific inflated shape 20 for the device. In the embodiment illustrated in FIGS. 1-6 and 12-13, the inflatable body 30 has a plurality of gussets 32 connected to the top sheet 26 and the bottom sheet 27 and extending across the cavity 31. The gussets 32 in one embodiment are U-shaped in cross-section, having a base 32A connected to one of the top and bottom sheets 26, 27, with two arms 32B extending across the cavity 31 between the top and bottom sheets 26. In the embodiment of FIGS. 1-6 and 12-13, the device 20 includes U-shaped gussets 32 where the base 32A is connected to the bottom sheet 27, and each of the arms 32B is connected at opposite ends to the bottom sheet 27 and the top sheet 26. The gussets 32 are elongated, such that the U-shaped cross-section is extended in a direction between the side edges 23 and generally parallel to the head and foot edges 23 of the device 20. In this configuration, the base 32A and the two arms 32B of each gusset 32 are formed as generally planar sheet structures that are under tension when the device 20 is inflated, and the arms 32B form walls extending between the top and bottom sheets 26, 27. The gussets 32 may be connected to the sheets 26, 27 by stitching in one embodiment, and other connection techniques described herein may additionally or alternately be used as well. In the embodiment of FIGS. 1-6 and 12-13, the gussets 32 are connected along connection lines 33 that extend in a direction between the side edges 23 and generally parallel to the head and foot edges 23 of the device 20. The connection lines 33 may be formed by stitching, adhesive, welding, and/or other connection techniques or combinations of such techniques. In the embodiment shown in FIGS. 12-13, the ends 32C of the arms 32B of the gussets 32 are hemmed and stitched to the top sheet 26 along the connection lines 33, and additional stitching is used to connect the base 32A to the bottom sheet 27 to form connection lines 33 on the bottom sheet 27. The gussets 32 limit inflation of the inflatable body 30, to give the device 20 a mattress-like shape when inflated. The device 20 includes seven gussets 32 and fourteen total gusset arms 32B in the embodiment illustrated in FIGS. 1-6 and 12-13, but may include a different number of gussets 32 in another embodiment, such as to create a different inflated configuration or depending on the size of the device 20 and/or the width/spacing of the gussets 32. In other embodiments, the device 20 may include a different configuration of gussets 32, or the device 20 may include a different type of inflation-limiting structure, such as threads, wires, narrow strips of material, etc., that connect the top and bottom sheets 26, 27 to limit inflation. For example, in one embodiment (as shown in FIG. 25), the gussets 32 may include only a single arm 32B and no base 32A The fully inflated device 20 has a shape that is defined by the configuration of the edges 23 of the device 20 and the size, shape, and configurations of the gussets 32, among other factors. In one embodiment, the top surface 21 of the device 20 has a peripheral cushion 34 around at least some of the edges 23 of the device 20 and a central area 35 at least partially surrounded by the peripheral cushion 34. For example, in the embodiment as shown in FIG. 2, the peripheral cushion 34 extends along all edges 23 of the device 20, so that the central area 35 is surrounded on all sides by the peripheral cushion 34. In another embodiment, the peripheral cushion 34 may extend only on the left and right side edges 23 of the device 20, so that the cushion 34 borders the left and right sides of the central area 35. The peripheral cushion 34 is raised with respect to at least a portion of the central area 35 in the embodiment as shown in FIG. 2, to resist sliding or rolling of the patient 70 off of the device 20 when the device is inflated. The central area 35 also includes swells 36 extending between the stitching lines 33 of the gussets 32. The bottom surface 22 of the device 20 may have a similar structure when inflated, with a peripheral cushion 34 bordering a central area 35 with swells 36, where at least a portion of the central area 35 is recessed with respect to the cushion 34. It is understood that the inflated device 20 may have a different shape when under force, e.g., when a patient 70 is positioned on top of and compressing the device 20.

Figure 13:
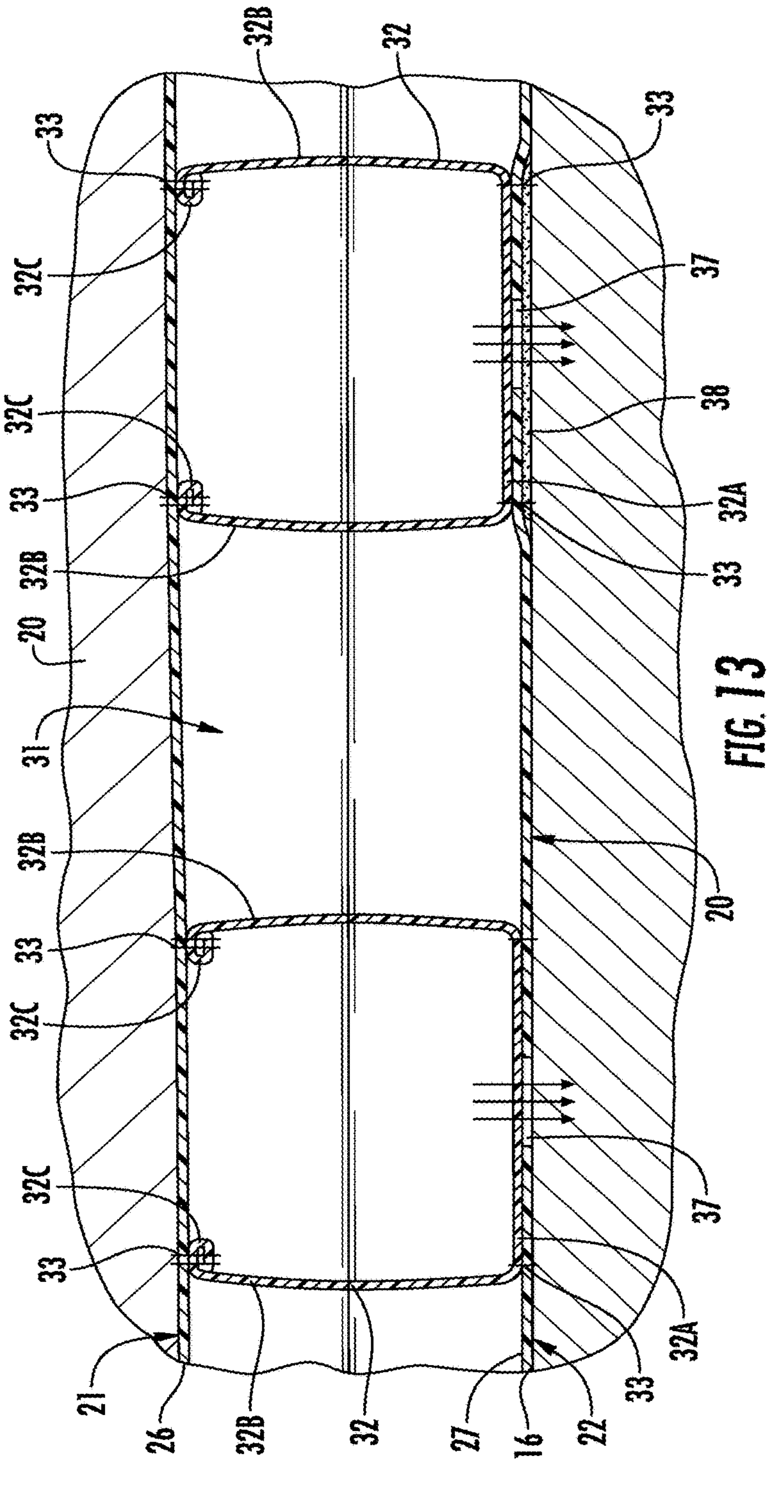
FIG. 13 is a magnified view of a portion of the inflatable device as shown in FIG. 12.

The device 20 as illustrated in FIGS. 1-6 and 12-13 includes a plurality of passages 37 in the bottom sheet 27 that permit air to pass from the cavity 31 to the exterior of the device 20. The passages 37 extend from the cavity 31 through the bottom sheet 27 to the exterior of the device 20 on the bottom surface 22. Air passing through the passages 37 is forced between the bottom surface 22 of the device 20 and the surface upon which the device 20 sits (e.g., the supporting surface 16 of the bed 12), reducing friction between the bottom surface 22 and the supporting surface. Passage of air through the passages 37 is illustrated in FIG. 13. This permits easier movement of the device 20 when a patient 70 is positioned on the device 20, as described in greater detail elsewhere herein. The passages 37 in the embodiment of FIGS. 1-6 and 12-13 are located within the central area 35 on the bottom surface 22, between the stitching lines 33 of the gussets 32. Additionally, in one embodiment, some or all of the passages 37 are located immediately below the bases 32A of one or more of the gussets 32. In the embodiment of FIGS. 1-6 and 12-13, all but one of the gussets 32 have passages 37 beneath their bases 32A, and all of the passages 37 are located beneath one of the gussets 32. In other embodiments, all of the gussets 32 may have passages 37 beneath their bases 32A, or at least a majority of the gussets 32 may have passages beneath their bases 32A. In a further embodiment, at least some (or all) of the passages 37 may be located between the gussets 32. In the embodiment shown in FIGS. 12-13, the gussets 32 (or at least the bases 32A thereof) are made from an air-permeable material, such that air passes through the bases 32A of the gussets 32 and downward through the passage(s) 37. The gusset bases 32A in this configuration can function to limit the air flow through the passages 37 to maintain a desired level of inflation of the device 20, as well as to diffuse the air flowing out of the passages 37 to improve the friction-reducing properties created by the air escaping through the passages 37. As used herein, an "air-permeable material" is a material that permits air to pass through, without the necessity for manually forming holes, passages, perforations, slits, openings, etc., in the material, such as by mechanical and/or laser cutting methods.

In other embodiments, the gussets 32 may be made from a material with limited or no air permeability. In such embodiments, air can pass through the passages 37 by passing around the lateral ends of the gussets 32 and/or through perforations that have been formed in the gusset bases 32A, or the gussets 32 may not include a base 32A, as shown in FIG. 25. The embodiment in FIG. 25 includes gussets 32 that are formed as arms 32B connected to the top and bottom sheets 26, 27, without any base 32A covering the passage 37. The device 20 in FIG. 25 has a piece 47 of an air-permeable material that is separate from the gussets 32 to cover the passage 37, in order to achieve the airflow limiting and diffusion functions described above. The separate piece 47 of the air-permeable material in FIG. 25 is shown as covering a single passage 37, however in other embodiments, one piece 47 of the air-permeable material may cover multiple passages 37, and the device 20 may include a single piece 47 of the air-permeable material that covers some or all of the passages 37 in one embodiment. It is understood that in various embodiments, some or all of the passages 37 generally have some form of air-permeable material covering in order to limit and diffuse airflow through the passage 37, which may include portions of gussets 32, separate pieces 47 of air-permeable material, other structures, and/or combinations of such structures. The embodiment in FIGS. 1-13 has air-permeable material covering the passage 37 on both the inner and outer surfaces of the bottom sheet 27, but the device 20 may include air-permeable material on only the inner or outer surface of the bottom sheet 27 in another embodiment.

As described herein, some embodiments include at least one piece of an air-permeable material covering some or all of the passages 37, such as the embodiments of FIGS. 1-13, FIGS. 20-24, and FIG. 26, where the air-permeable gussets 32 cover some or all of the passages 37, and the embodiment of FIG. 25, where a separate piece 47 of air-permeable material covers some or all of the passages 37. The permeability of such air-permeable materials can limit or govern the rate of airflow through each passage 37. In one embodiment, the permeability of the air-permeable material covering the passage(s) 37 is configured so that airflow through the passages 37 is sufficiently restricted to keep the device 20 inflated, while also being sufficiently large to permit an effective amount of air to pass through the passage(s) 37 to provide friction reduction between the device 20 and the supporting surface 16. When an air-permeable fabric is used in this structure, the "tightness" of the warp or weave of the material and the resultant sizes of the interstices between the fabric threads influence the permeability of the fabric. Thus, in one embodiment, an air-permeable fabric material may be used that has a suitable average interstice size to provide the desired level of permeability and airflow. A rip-stop nylon fabric material is one example of an air-permeable material that can be used for the gussets 32 and/or other pieces 47 covering the passages 37.

The overall permeability of the materials covering each passage 37 (including the gusset 32, the separate piece 47 of air-permeable material, and/or the cover 38, depending on configuration) permits an overall airflow rate of about 36-46 CFM (cubic feet per minute) through the passage 37 in one embodiment, or an overall airflow rate of 39-43 CFM in another embodiment, e.g., an airflow rate of about 41 CFM. In one embodiment, this overall airflow rate may result from a combination of a gusset 32 or piece 47 of air-permeable material and a cover 38 as described herein. In such an embodiment, the gusset 32 or piece 47 of air-permeable material may have a lower permeability than the cover 38, as described herein, such as a permeability of 39-47 CFM, a permeability of 41-45 CFM, or a permeability of about 43 CFM, in various examples. The higher-permeability cover 38 may have a permeability of 300-500 CFM, or 350-440 CFM, or about 390 CFM, in various examples. It is understood that these airflow rates are calculated free of extrinsic restrictions, e.g., the bottom surface 22 of the device 20 being placed against a supporting surface 16 in use may affect the actual airflow rates through the passages 37 in use, which is not reflected in the reported figures.

As described herein, in one embodiment, some form of air-permeable material covers all of the passages 37 and limits the airflow through each passage 37, so that the airflow rate through each of the passages 37 is restricted. It is understood that in such an embodiment, the size of the passage 37 may affect the overall airflow rate through each passage 37, such as in the embodiment of FIGS. 20-24, which includes passages 37 of different sizes. All of the passages 37 in this configuration may be covered with the same air-permeable material, or different air-permeable materials with similar permeabilities, in one embodiment. Additionally, as shown in FIGS. 12-13 and 23-26, at least some of the passages 37 may be covered by multiple pieces of air-permeable material, e.g., the gusset 32 and the cover 38 in FIGS. 12-13, 23-24, and 26, and the piece 47 and the cover 38 in FIG. 25. In such a configuration, the two different pieces of air-permeable material covering each passage 37 may have different permeabilities, such that the material with the lower permeability governs the airflow rate through the passage 37. In other words, a passage 37 may be covered by two pieces of air-permeable material, where the first piece has a lower permeability value than the second piece and permits a lower airflow rate than the second piece. In the embodiments of FIGS. 12-13 and 23-26, the permeability of the material on the inner surface of the bottom sheet 27, i.e., the gussets 32 and the pieces 47, is lower than the permeability of the material on the bottom surface 22, i.e., the covers 38. Thus, the permeability of the gussets 32 and the pieces 47 in these embodiments govern the airflow rate through the passages 37. In another embodiment, the device 20 may have an air-permeable piece connected to the bottom surface 22 that functions to limit the airflow through the passage 37, optionally with a second, higher-permeability piece also connected to the bottom sheet 27, either on the inner surface of the bottom sheet 27 or on the bottom surface 22 above or below the first piece of air-permeable material. Further, it is understood that the permeability of any materials covering the passages 37 may be greater than the overall permeability of the materials defining the cavity 31, e.g., the top and bottom sheets 26, 27 in the embodiments of FIGS. 1-26.

The passages 37 in the embodiment of FIGS. 1-6 and 12-13 are arranged in laterally-extending rows and are all circular in shape, varying in size. As seen in FIGS. 4-5, the passages 37 nearest the head and foot edges 23 of the device

Figure 14:
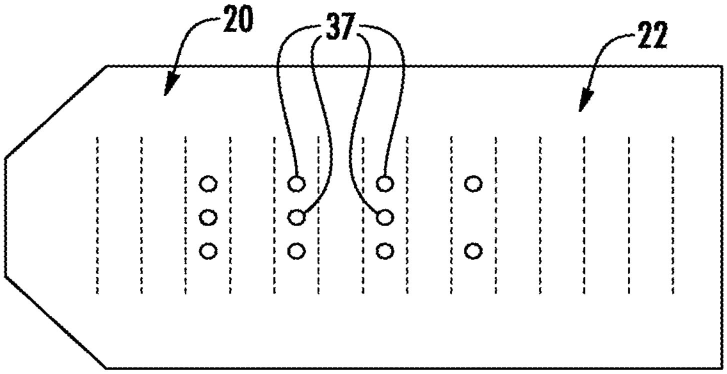
FIGS. 14-17 are bottom elevation views of additional embodiments of inflatable devices configured for use with the system of FIG. 1, according to aspects of the disclosure.
Figure 15:
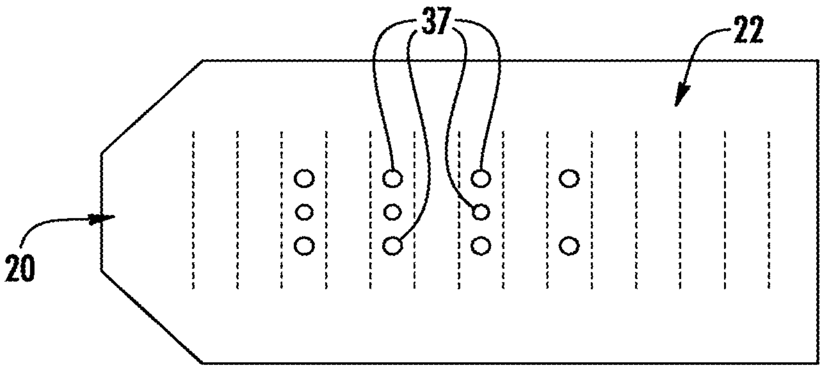
Figure 16:
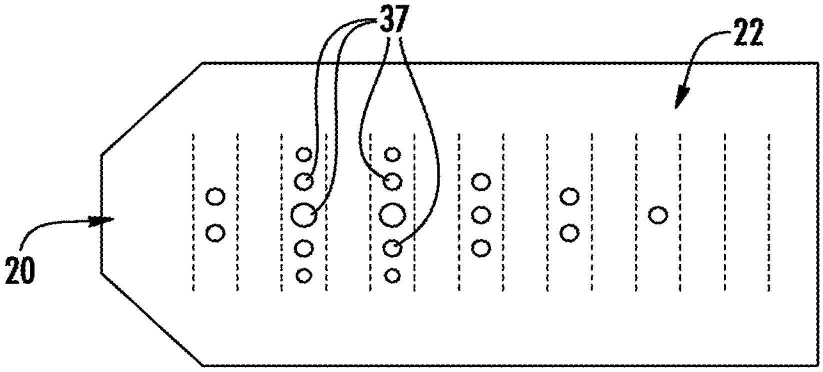
Figure 17:
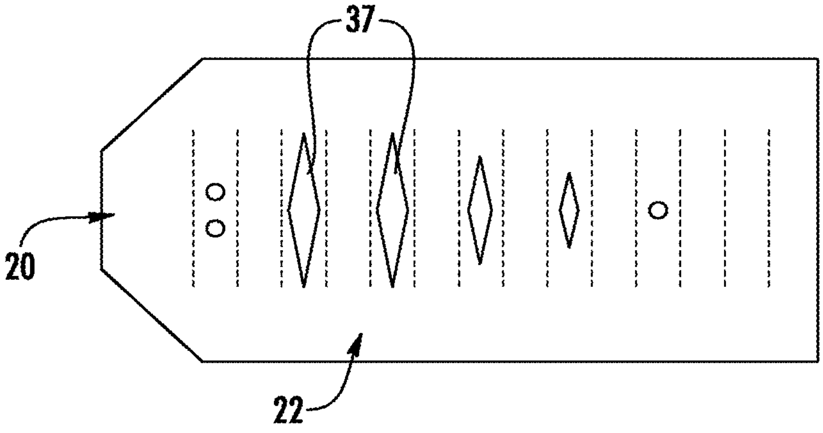

20 are smaller than the passages 37 closer to the middle of the device 20, with the larger passages 37 being arranged into three lateral rows of three passages 37 and one lateral row of two passages 37. The device 20 may have other configurations of passages 37 in other embodiments, including different shapes, sizes, numbers, and/or arrangements of passages 37. For example, FIGS. 14-17 illustrate potential alternate configurations of passages 37 in the device 20. FIG. 17 illustrates a configuration with a combination of circular passages 37 as in FIGS. 1-6 and diamond-shaped passages 37 that are elongated in the lateral (side-to-side) direction. The device 20 in FIG. 17 has two large diamond passages 37, and two additional diamond passages 37 that are progressively smaller toward the foot edge 23 of the device 20. FIG. 15 illustrates a configuration with lateral rows of circular passages 37 that have different sizes, with a smaller passage 37 in the center and larger passages 37 on each side of the smaller passage 37. FIG. 16 illustrates a configuration with lateral rows of circular passages 37 that have different sizes, with the largest passage in the center and additional passages 37 on both sides of the largest passage 37, growing progressively smaller toward the side edges 23. FIG. 14 illustrates a configuration similar to that of FIGS. 1-6, but with passages 37 that are smaller in size and fewer in number. It is noted that the sizes and arrangement of the passages 37 may place passages 37 occupying a greater aggregate surface area in the areas designed to be positioned beneath the upper body and torso of the patient 70, as these areas will typically support greater weight and can benefit from an increased volume of air forming the air cushion in those areas. Still further configurations are possible.

In one embodiment, the device 20 may further include covers 38 that cover at least some of the passages 37, where the covers 38 are air-permeable and permit air to flow through them to form the air cushion beneath the device 20. The covers 38 may be connected to the bottom surface 22 of the device 20 by stitching the cover 38 to the bottom sheet 27 around the perimeter of each cover 38 in one embodiment. Other connection techniques may be used in other embodiments, including any technique(s) described herein. The covers 38 in the embodiment of FIGS. 1-6 are rectangular in shape, but may have a different shape in other embodiments. Additionally, in the embodiment of FIGS. 1-6 and 12-13, each cover 38 covers all of the passages 37 in a lateral row, and each cover 38 is positioned beneath a single gusset 32 and is aligned with said gusset 32, but not all passages 37 are covered by a cover 38. In other embodiments, the size, arrangement, and number of the covers 38 may be different. For example, in one embodiment, a cover 38 may cover multiple passages 37 that are spaced from each other in the head-toe direction on the device 20, and in another embodiment, the device 20 may have a single cover 38 or a pair of covers 38 covering some or all of the passages 37. As described herein, some or all of the covers 38 may be formed of a directional stitching material 45, which is configured to interact with contacting surfaces of the wedge(s) 50A-B and/or the bed 12 to limit sliding of the device 20 in one or more directions. The covers 38 may therefore extend sufficiently close to both of the side edges 23 of the device 20 that they will engage the ramp surface(s) 52 of the wedge(s) 50A-B in use. The covers 38 may be positioned beneath the upper body, torso, sacral area, and thigh areas of the patient 70, to ensure contact with the wedge(s) 50A-B. The covers 38 may further limit ingress of dust, dirt, debris, etc., into the passages 37, and the covers 38 can also function to limit the air flow through the passages 37 and diffuse the air flowing out of the passages 37, as similarly discussed above with respect to the gussets 32. The use of two different materials covering the passages 37 in this embodiment may enhance this functionality. It is understood that the devices 20 in FIGS. 14-17 may include covers 38 that are similar to the covers 38 in FIGS. 1-6 and 12-13 discussed herein.

In other embodiments, the covers 38 may be formed from a different material, such as a different type of fabric material that may or may not have directional friction properties. For example, in one embodiment, the device 20 may utilize covers 38 covering one or more of the passages 37 that are not made of a material with directional friction properties, and the device 20 may have separate pieces of the directional stitching material 45 positioned elsewhere on the bottom surface 22. In a further embodiment, the device 20 may not utilize any covers 38, and the device 20 may further have pieces of the directional stitching material 45 positioned elsewhere on the bottom surface 22.

In the embodiment illustrated in FIGS. 1-6, the top surface 21 of the device 20 has at least a portion formed of a high-friction or gripping material 24, and the bottom surface 22 has at least a portion formed of a low-friction material 25. In one embodiment, both the top and bottom sheets 26, 27 are made from the low-friction material 25, such as by using a low-friction sheet material, and the high-friction material 24 may be connected to at least the top sheet 26. For example, the high-friction material 24 may be or include a coating applied to the inflatable body 30, such as a spray coating. In the embodiment of FIGS. 1-6, both the top and bottom sheets 26, 27 include the coating of the high friction material 24, with the coating on the top sheet 26 facing outward to form part of the top surface 21 of the device 20 and the coating on the bottom sheet 27 facing inwardly to form a surface of the cavity 31. This coating may be a polyurethane coating that is waterproof and/or breathable in one embodiment. This inward-facing high-friction coating 24 on the bottom sheet 27 can resist slipping of the top and bottom sheets 26, 27 with respect to each other. In another embodiment, only the top sheet 26 has the coating of the high-friction material 24. In another embodiment, the high-friction material 24 may be in the form of one or more pieces of high-friction sheet material connected to the top surface 21 of the inflatable body 30 in a surface-to-surface, confronting relation to form a layered structure, in various embodiments. For example, the high friction material 24 may be a knitted material, which can enhance comfort, and may be made of polyester and/or another suitable material. The material 24 can then be treated with a high friction substance, such as a hot melt adhesive or appropriate plastic, which can be applied as a discontinuous coating to promote breathability. In a further embodiment, the portion of the inflatable body 30 forming the top surface 21 (e.g., top sheet 26) may be formed of the high-friction material 24, while the portion of the inflatable body 30 forming the bottom surface 22 (e.g., bottom sheet 27) may be formed of the low-friction material 25. It is noted that the high-friction material 24 may form or cover the entire top surface 21 of the device 20 in one embodiment, or may only form or cover a portion of the top surface 21 in another embodiment, e.g., the low-friction material 25 may form a portion of the top surface 21, with the edges of the high-friction material 24 being recessed from the edges 23 of the device 20. Similarly, the low-friction material 25 may form at least a portion of the bottom surface 22 of the device 20.

As described in greater detail below, the low-friction material 25 permits sliding of the device 20 in contact with the supporting surface 16 of the bed 12, which may include a fitted bed sheet 15 or other sheet, and the high-friction material 24 provides increased resistance to slipping or sliding of the patient and/or the body pad 40 on which the patient may be lying, in contact with the device 20. The low-friction material 25 may also have rip-stop properties, and may have suitable structural strength and stability to form the primary structural component of the device 20. The high-friction and/or low-friction materials 24, 25 can also be treated with a water repellant, such as polytetrafluoroethylene (PTFE). In other embodiments, the high-friction and/or low-friction materials 24, 25 may include any combination of these components, and may contain other components in addition to or instead of these components.

Generally, the high friction material 24 has a coefficient of friction that is higher than the coefficient of friction of the low friction material 25. In one embodiment, the coefficient of friction for the high friction material 24 is about 8-10 times higher than the coefficient of friction of the low friction material 25. In another embodiment, the coefficient of friction for the high friction material 24 is between 5 and 10 times higher, or at least 5 times higher, than the coefficient of friction of the low friction material 25. The coefficient of friction, as defined herein, can be measured as a direct proportion to the pull force necessary to move either of the materials 24, 25 in surface-to-surface contact with the same third material, with the same normal force loading. Thus, in the embodiments above, if the pull force for the high friction material 24 is about 8-10 times greater than the pull force for the low friction material 25, with the same contact material and normal loading, the coefficients of friction will also be 8-10 times different. It is understood that the coefficient of friction may vary by the direction of the pull force, and that the coefficient of friction measured may be measured in a single direction. For example, in one embodiment, the above differentials in the coefficients of friction of the high friction material 24 and the low friction material 25 may be measured as the coefficient of friction of the low friction material 25 based on a pull force normal to the side edges 23 (i.e. proximate the handles 28) and the coefficient of friction of the high friction material 24 based on a pull force normal to the top and bottom edges 23 (i.e. parallel to the side edges 23).

Additionally, the coefficient of friction of the interface between the high-friction material 24 and the body pad 40 is greater than the coefficient of friction of the interface between the low friction material 25 and the bed sheet or supporting surface 16. It is understood that the coefficients of friction for the interfaces may also be measured in a directional orientation, as described above. In one embodiment, the coefficient of friction for the interface of the high friction material 24 is about 8-10 times higher than the coefficient of friction of the interface of the low friction material 25. In another embodiment, the coefficient of friction for the interface of the high friction material 24 is between 5 and 10 times higher, or at least 5 times higher, than the coefficient of friction of the interface of the low friction material 25. It is understood that the coefficient of friction for the interface could be modified to at least some degree by modifying factors other than the device 20. For example, a high-friction material (e.g., substance or surface treatment) may be applied to the bottom surface 44 of the pad 40, to increase the coefficient of friction of the interface, which may be done in addition to, or in place of, using the high-friction material 24 on the device 20. An example of a calculation of the coefficients of friction for these interfaces is described in greater detail in U.S. Patent Application Publication No. 2012/0186012, published Jul. 26, 2012, which is incorporated by reference herein in its entirety and made part hereof, which calculation is made using a rip-stop nylon material as the low friction material 25 and a knitted material treated with a hot melt adhesive as the high friction material 24. The relative coefficients of friction of the high friction material 24 and the low friction material 25 used in the example calculation are also described in the aforementioned publication.

In an alternate embodiment, the device 20 may not utilize a high friction surface, and instead may utilize a releasable connection to secure the pad 40 in place with respect to the device 20. For example, the device 20 and pad 40 may include complementary connections, such as hook-and-loop connectors, buttons, snaps, or other connectors. In a further embodiment, the device 20 may be used without a pad 40, with the patient 70 directly in contact with the top surface 21 of the sheet, and the high-friction material 24 can still resist sliding of the patient on the device 20.

In one embodiment, the device 20 further has a directional stitching material 45 connected to the bottom surface 22, which may be in the form of one or more additional pieces of sheet material that is formed partially or entirely of the directional stitching material 45. Additionally, the one or more additional pieces of the directional stitching material 45 may form at least a portion of the bottom surface 22 of the device 20, with the edges of each piece being recessed from the edges 23 of the device 20, and with the pieces of the directional stitching material 45 being spaced from each other. In the embodiment of FIGS. 1-6, the device 20 has the covers 38 formed of the directional stitching material 45, and the material of the covers 38 allows airflow through while also providing directional friction properties as discussed herein. The covers 38 may be connected to the device 20 by stitching in one embodiment, but may have additional or alternate connections in other embodiments, including any connections described herein. In another embodiment, the device 20 may have separate pieces of directional stitching material 45 on the bottom surface 22, and the covers 38 may be made of a different type of material, or may be absent.

Figure 18:
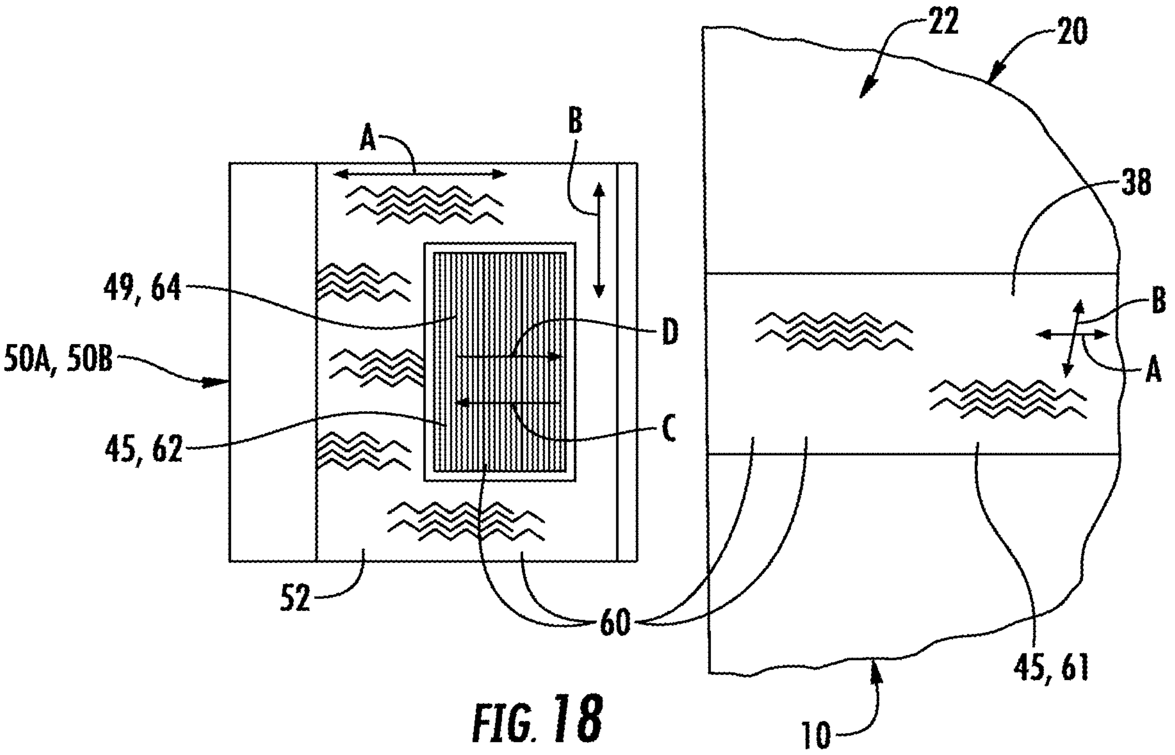
FIG. 18 is a schematic plan view of various selective glide assemblies of the system of FIG. 1, with arrows schematically illustrating directions of free movement and directions of resistance to movement between the components of the system.

The directional stitching material 45 on the bottom surface 22 of the device 20, e.g., the covers 38 in the embodiment of FIGS. 1-6, forms engagement members 61 of a selective gliding assembly 60 (which may be referred to as "sheet engagement members"), to permit movement of the device 20 in desired directions and resist movement of the device 20 in undesired directions. It is understood that in another embodiment, the device 20 may have one or more such engagement members 61 on the bottom surface 22 that are not configured as covers 38 for the passages 37, and such an embodiment may additionally have covers 38 that may or may not be formed of a directional glide material 45, or such an embodiment may have no covers 38. In the embodiment of FIGS. 1-6, the axis B (along which gliding is resisted) is oriented to extend between the top and bottom edges 23 and parallel to the side edges 23, and the axis A (along which gliding is allowed) is oriented to extend between the side edges 23 and parallel to the top and bottom edges 23, as shown in FIGS. 18-19. When the wedge(s) 50A-B are inserted in position as shown in FIG. 6, then relative to the wedge(s) 50A-B, the axis B is oriented to extend parallel to at least one of the front end 57 (or the apex 55) and the back wall 53 of the wedge and/or between the side walls 54, and the axis A is oriented to extend between the front end 57 and the back wall 53 of the wedge and/or parallel to the side walls 54. This arrangement is illustrated schematically in FIG. 18. In a further embodiment, one or more of the engagement members 61 may be formed of a different directionally-oriented material, and/or may be oriented to allow/resist gliding in different directions. For example, if the orientations of the engagement members 61 as depicted in FIG. 18 are turned 90°, then movement in a direction extending between the side edges 23 and parallel to the top and bottom edges 23 would be resisted, and movement in a direction extending between the top and bottom edges 23 and parallel to the side edges 23 would be allowed.

In one embodiment, as illustrated in FIGS. 1-6, the device 20 may also include one or more handles 28, 48 to facilitate pulling and other movement of the device 20. Such handles 28, 48 may be configured for multiple different types of movement, including "boosting" the patient 70 on the bed 12 (i.e., moving the patient 70 toward the head 13), positioning the patient 70 on the bed 12, pulling the patient 70 up onto the wedges 50A-B, moving the patient 70 from one bed 12 or other surface to another, etc. As shown in FIGS. 1-6, the device 20 has handles 28 formed by strips 29A-B of a strong material that are connected (e.g., stitched) in periodic fashion to the bottom surface 22 at or around both side edges 23 of the device 20, as well as the top edge 23 of the device. The non-connected portions can be separated slightly from the device 20 to allow a user's hands 76 to slip underneath, and thereby form the handles 28. The handles 28 formed by the strips 29A on the side edges 23 of the device 20 are useful for pulling the device 20 laterally, to move the patient 70 laterally on the bed 12. The device 20 also includes handles 48 in the form of flaps that are connected (e.g., stitched) to the bottom surface 22 of the device 20 and extend outwardly from the device 20. The handles 48 extend generally outward from the side edges 23 of the device 20, and in the embodiment of FIGS. 1-6, the device 20 has two handles 48 on each side. The handles 48 may also include strips 29A of the same material as the handles 28, to provide a point for gripping. In other embodiments, a larger or smaller number of handles 48 may be used. The handles 28, 48 may be useful for moving the device 20 and the patient 70 in many different ways, including pulling the device 20 laterally, turning the patient 70, and/or pulling the device 20 toward the head 13 of the bed 12 to "boost" the patient 70 and device 20 if they begin to slide toward the foot 17 of the bed 12, which may tend to happen especially when the patient 70 is inclined. In particular, the handles 48 extending from the sides 23 of the device 20 are constructed to facilitate rolling of the patient 70, and the wide base of the handles 48 spreads the force exerted on the device 20 over a larger area, which puts less pressure on the patient 70 during rolling. In other embodiments, the device 20 may include a different number or configuration of the handles 28, 48 as described above. Further, the handles 28, 48 may be connected to the device 20 in a different way, such as by heat welding, sonic welding, adhesive, etc. Other types of handles may be utilized in further embodiments.

Figure 9:
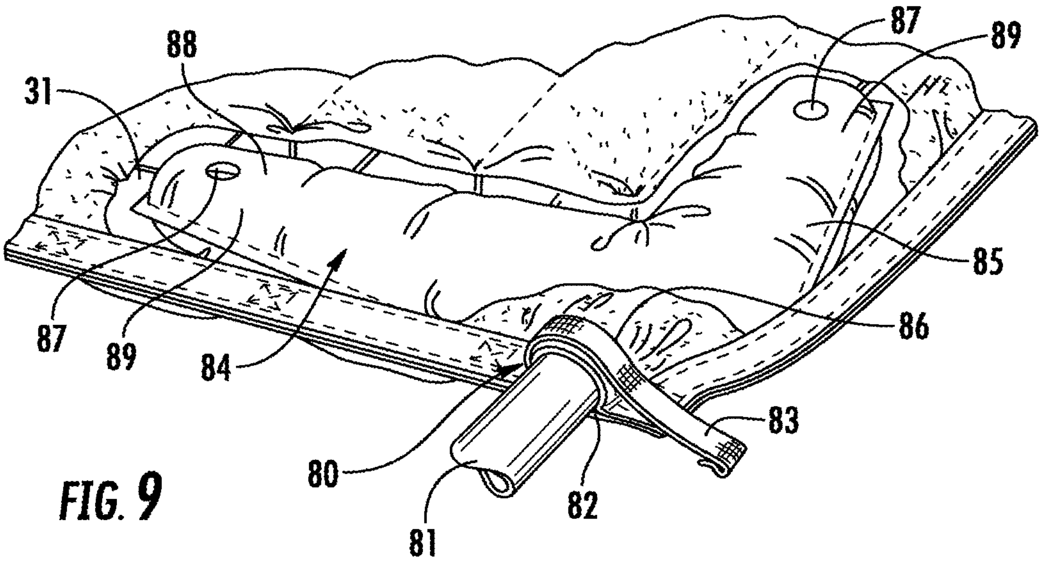
FIG. 9 is a perspective view of the inflatable device of FIGS. 1-5 with an air output connected to a port on the inflatable device.
Figure 10:
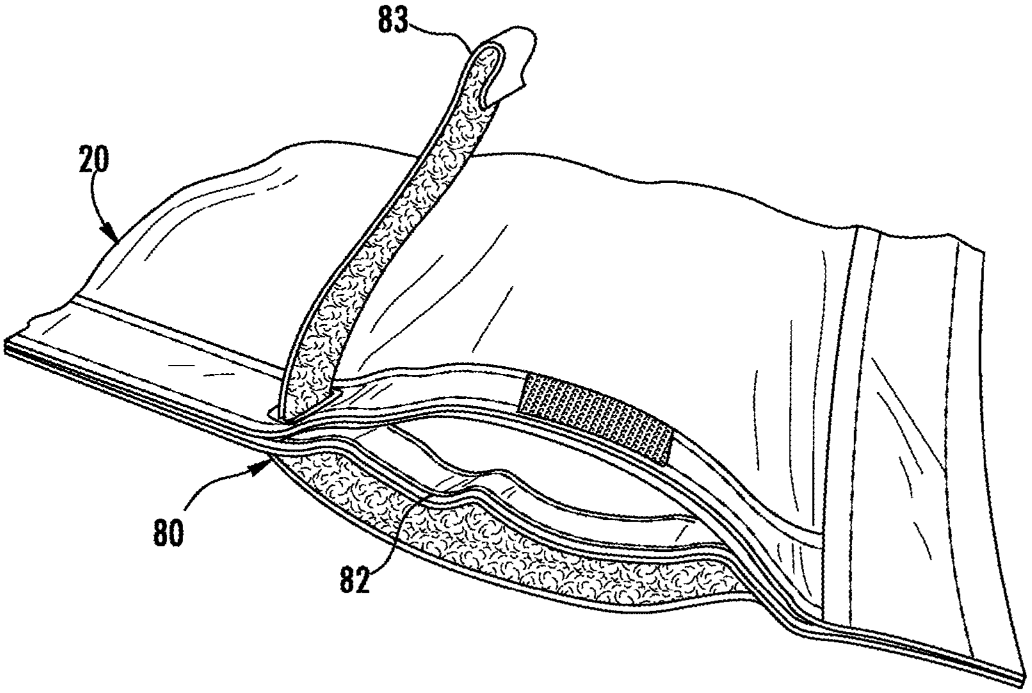
FIG. 10 is a magnified view of the port of the inflatable device shown in FIG. 9.
Figure 11:
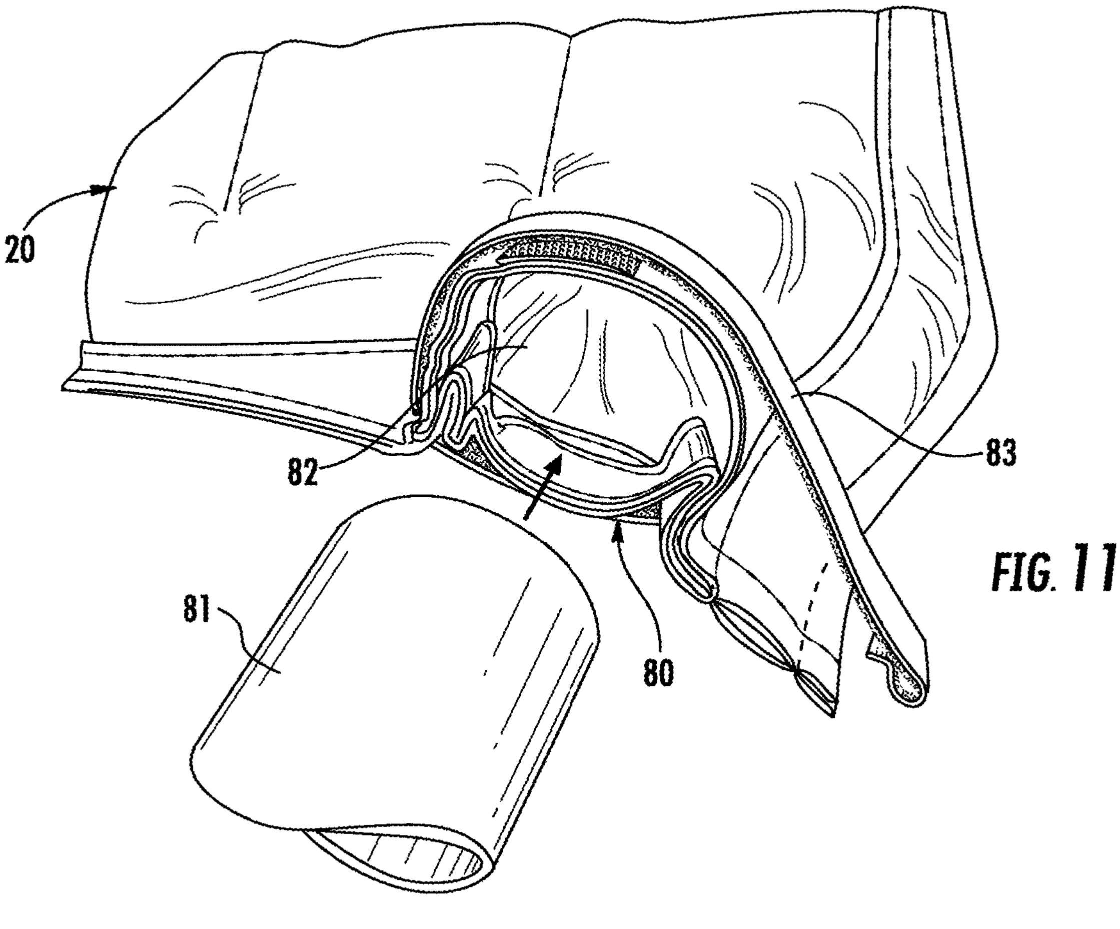
FIG. 11 is a magnified view of the port of the inflatable device shown in FIGS. 9-10, with the air output in position for insertion into the port.
Figure 12:
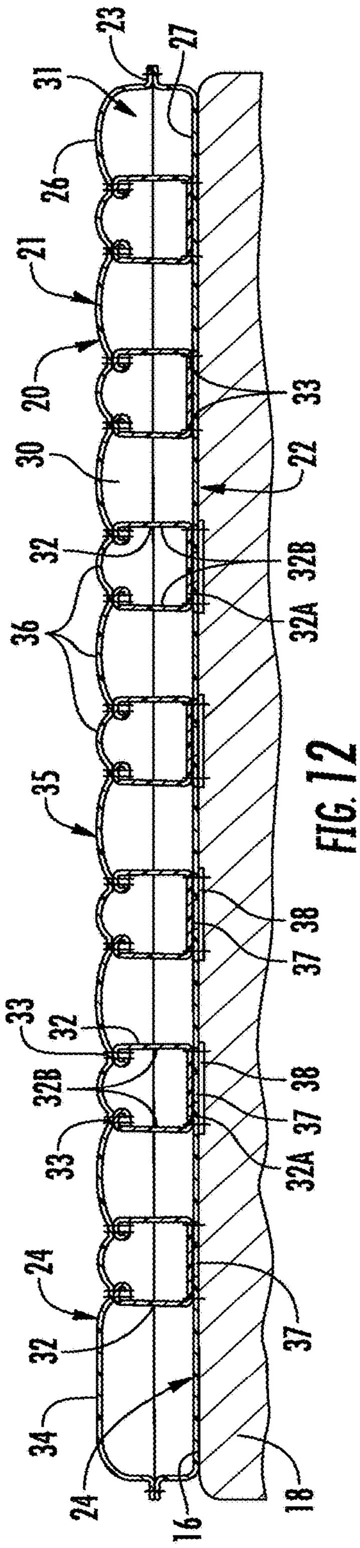
FIG. 12 is a cross-sectional view of the inflatable device of FIGS. 1-5.

The device 20 may be inflated by connection to an air output 81 as illustrated in FIGS. 1-6 and 9-11. The device 20 may include one or more inflation ports 80 for connection to the air output 81. It is understood that a device 20 with multiple ports 80 may include ports 80 on one or more different edges 23 of the device 20, and that the port(s) 80 may be along any edge 23 of the device 20. In the embodiment of FIGS. 1-6 and 9-11, the device 20 includes two inflation ports 80, each located along one of the side edges 23 of the device 20, proximate the foot edge 23. Generally, only one of the inflation ports 80 is used at a time, and the dual ports 80 provide for use in diverse arrangements, although both ports 80 could be used simultaneously. In one embodiment, each of the ports 80 includes an opening 82 configured to receive a portion of the air output 81 and a retaining mechanism 83 configured to retain the portion of the air output 81 within the opening 82. The retaining mechanism 83 in the embodiment of FIGS. 1-6 and 9-11 is a strap that wraps around the opening 82 and fastens to itself by a hook-and-loop fastener, as illustrated in FIGS. 9-11. Other fasteners could be used, such as snaps, buttons, ties, etc. The air output 81 illustrated in FIGS. 1-6 and 9-11 is a hose that may be connected to a pump 90 (see FIGS. 27-29) that pumps air through the air output 81. As shown in FIGS. 1-6 and 9-11, the air output 81 (hose) is received within the opening 82, and the retaining mechanism 83 (strap) is fastened to secure the air output 81 in place.

The device 20 may also have a valve 84 in communication with the port 80, as illustrated in FIGS. 3-5 and 9. The valve 84 in this embodiment is formed by a pocket 85 that is positioned within the cavity 31 and has an entrance opening 86 in communication with the opening 82 of the port 80 and at least one exit opening 87 in communication with the cavity 31. The pocket 85 may be formed by one or more sheets 88 of flexible material that are folded and/or connected together to define the pocket 85 in the desired shape. Additionally, the pocket 85 may be connected to the inner surfaces of the cavity 31 by stitching or another technique described herein. In the embodiment of FIGS. 3-5 and 9, the pocket 85 is stitched to the inside of the device 20 only around the port 80, and the rest of the pocket 85 is free within the cavity 31. The exit opening(s) 87 may be spaced from the entrance opening 86 so that air must flow through the pocket 85 to reach the cavity 31. In this configuration, airflow through the port 80 passes through the valve 84 by flowing from the port 80 through the entrance opening 86, then through the pocket 85 and out through the exit opening 87 into the cavity 31. The pocket 85 in the embodiment of FIGS. 3-5 and 9 has two branches 89 extending away from each other, e.g., to form an L-shape, and the exit openings 87 are located near the ends of the branches 89 to space them from the entrance opening and from each other 86. The valve 84 may perform multiple functions. For example, the pocket 85 may compress when there is no inward airflow through the entrance opening 86, thus resisting or preventing reverse airflow through the valve 84 and the port 80 when the port 80 is not being used for inflation (i.e., when another port 80 is being used). As another example, the valve 84 reduces noise and dispersion of the air during inflation. As a further example, the pocket 85 may also protect the air output 81 from contact with dirt, dust, debris, and other matter that may be present within the cavity 31. As yet another example, the positioning of the exit openings 87 in the embodiment illustrated in FIGS. 3-5 and 9 makes it difficult or impossible for the patient's leg to rest on top of both of the exit openings 87 of a single valve 84, which could impede air flow through the valve 84. In other embodiments, the valve 84 may be differently configured, such as by having a different shape, a greater or smaller number of exit openings 87, etc. It is understood that the valve 84 and other inflation components of the system 10 are described for use with air, but may be used with any suitable gas. Accordingly, terms such as "air" and "airflow" as used herein may refer to any suitable gas.

Figure 29:
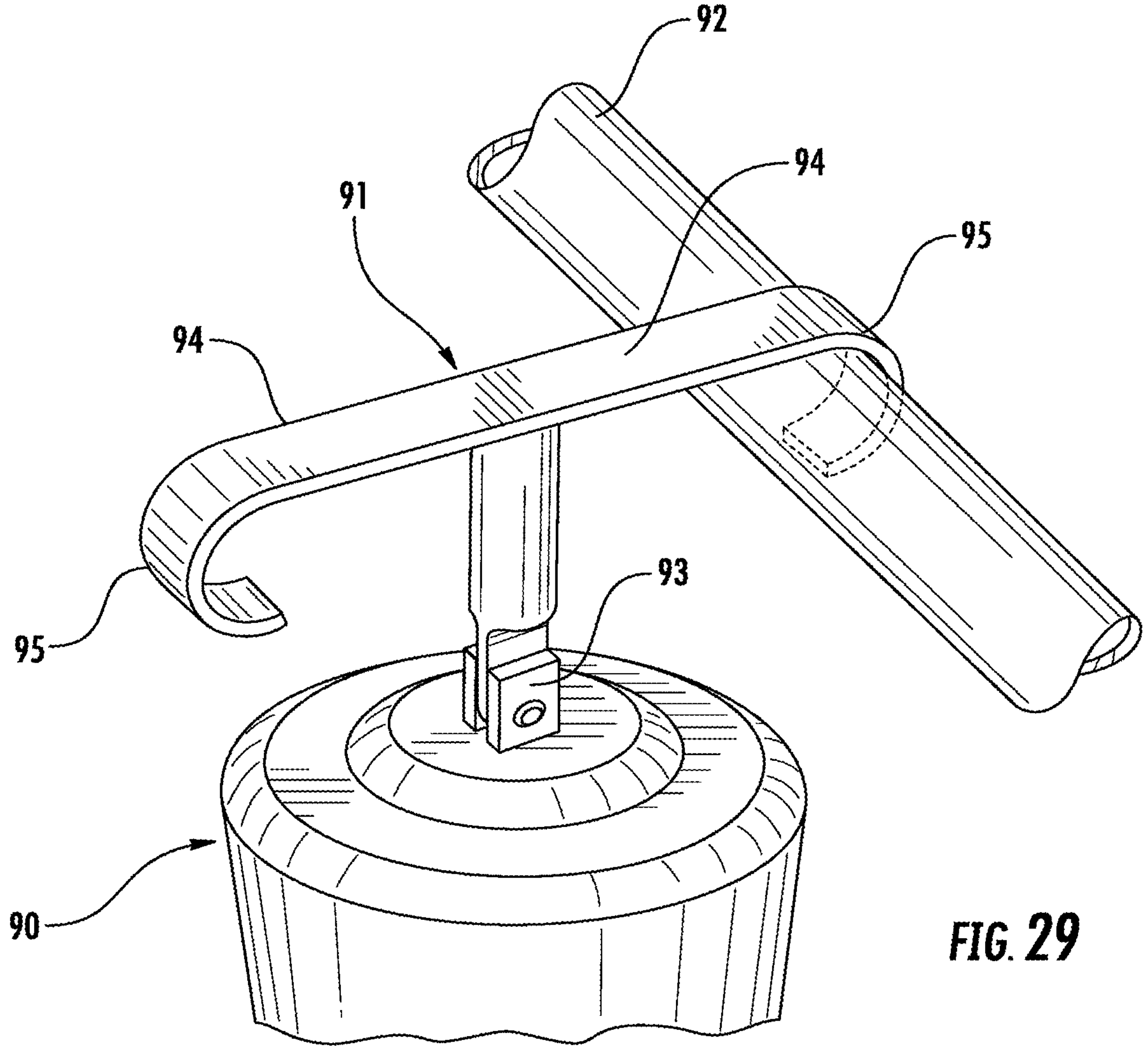
FIG. 29 is a perspective view of a portion of a pump according to aspects of the present disclosure.
Figure 30:
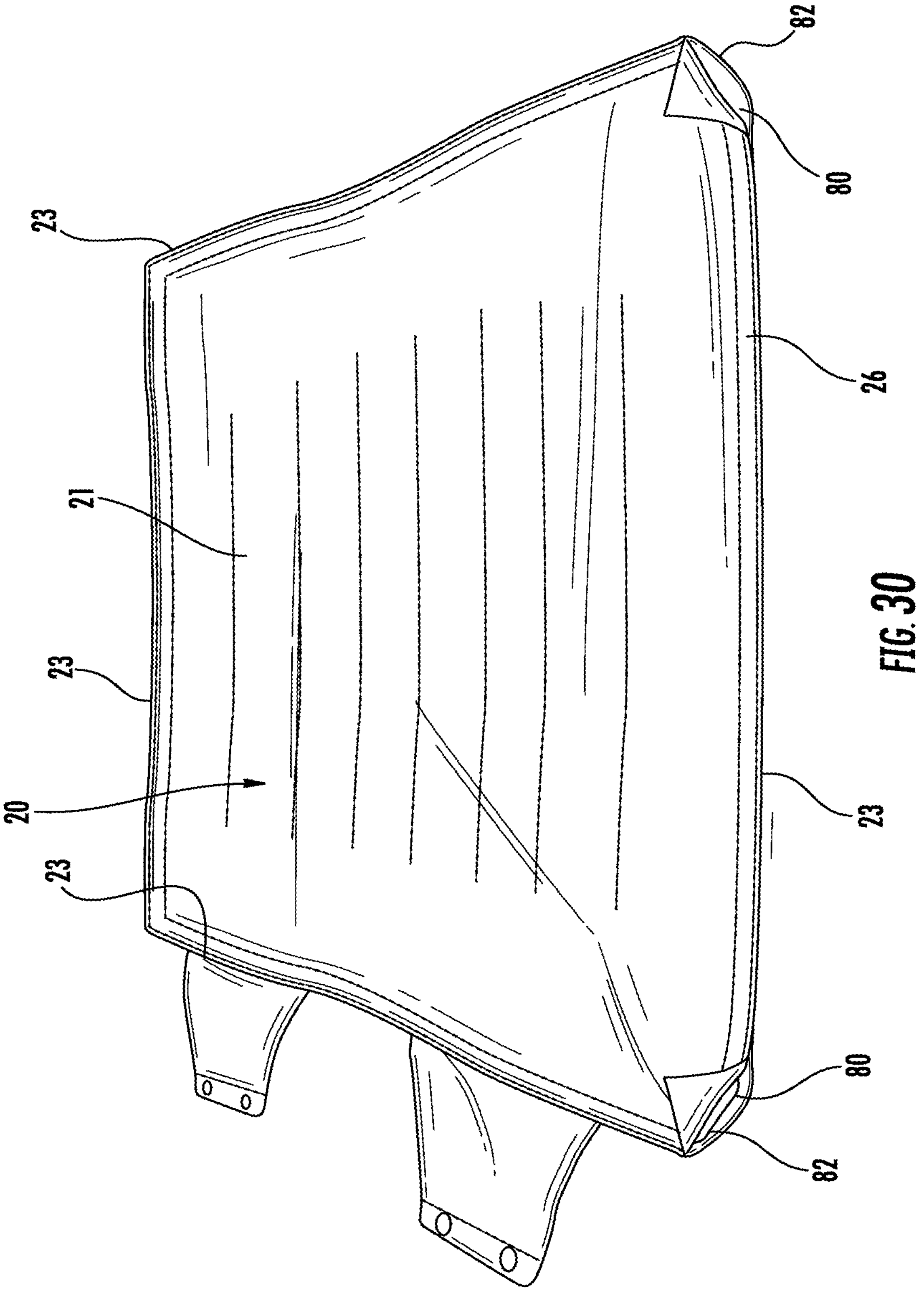
FIG. 30 is a top elevation view of another embodiment of a device for use with a system for turning and positioning a patient, according to aspects of the disclosure.
Figure 31:
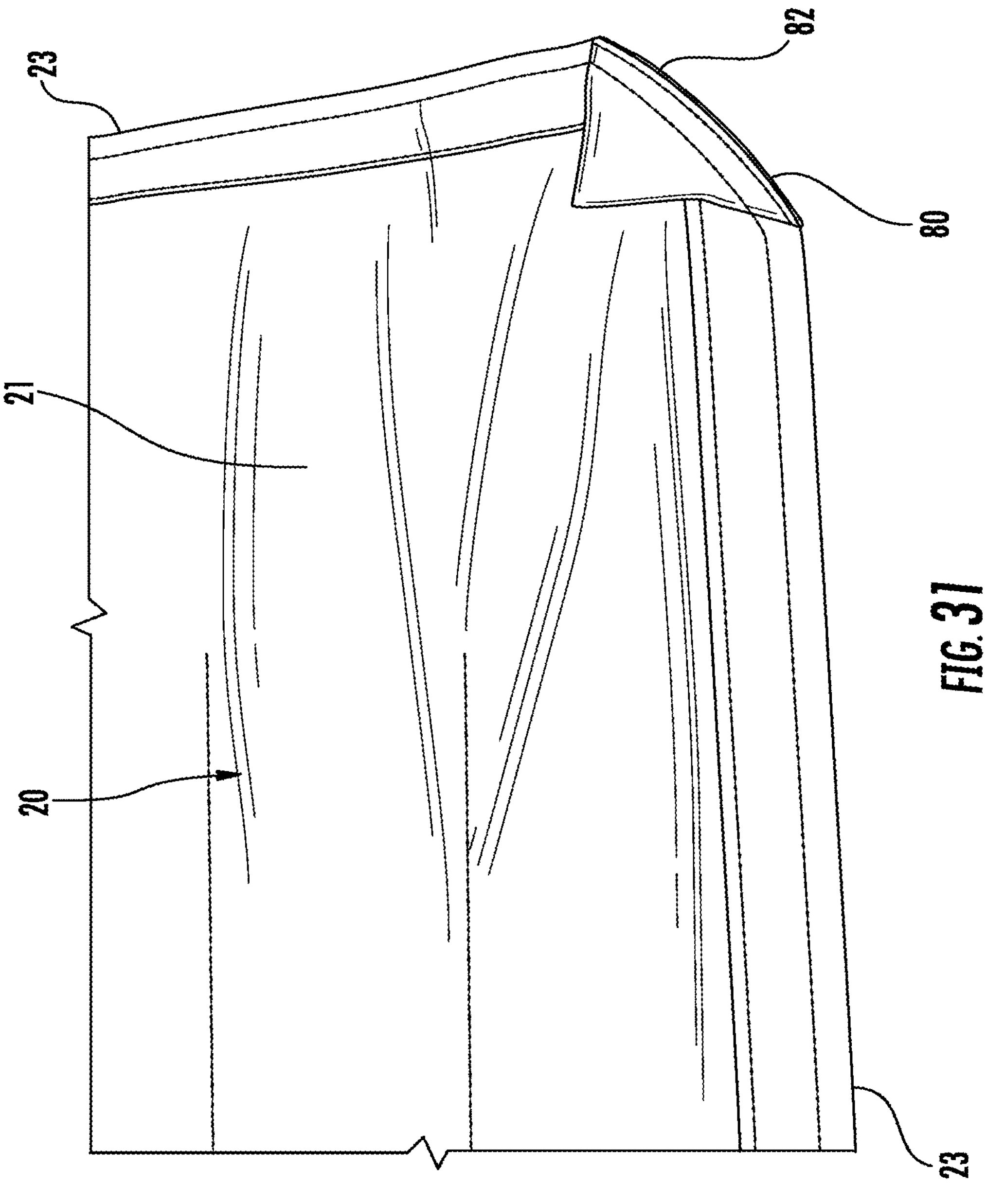
FIG. 31 is a top plan view of a portion of the device of FIG. 30.
Figure 32:
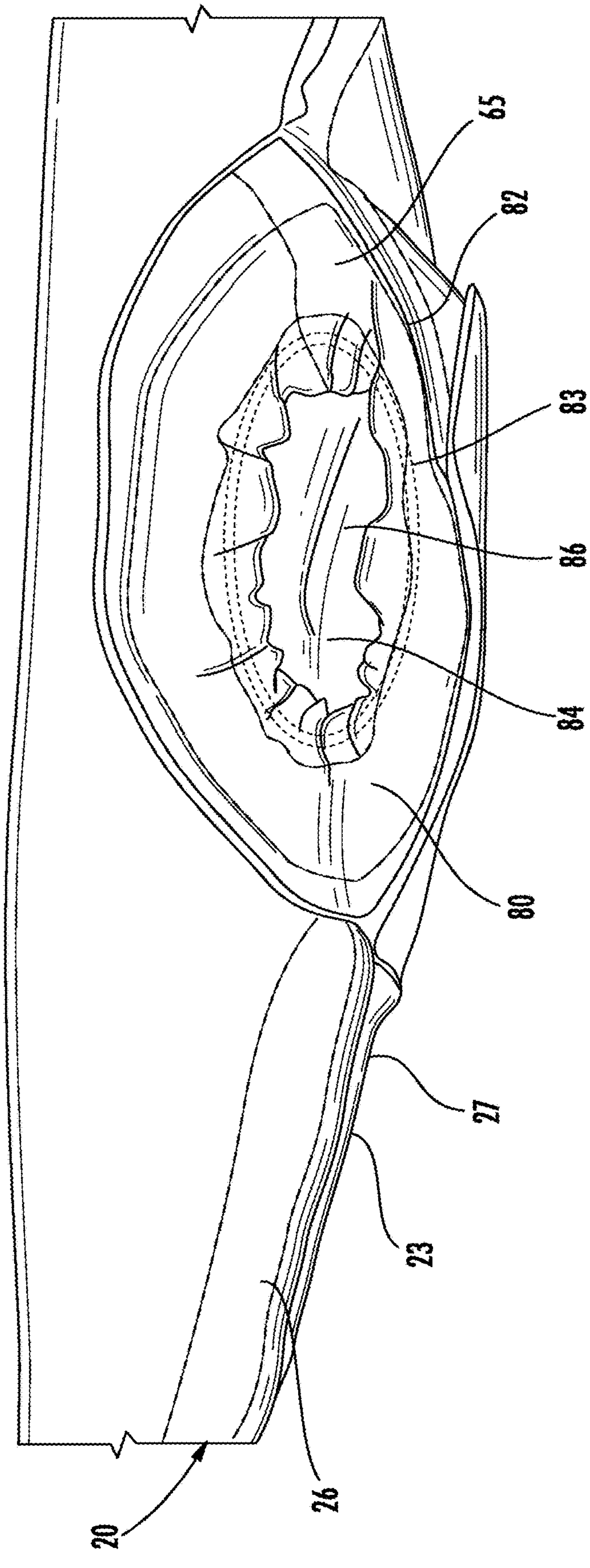
FIG. 32 is a magnified side view of a port of the device of FIG. 30.

One embodiment of the pump 90 is shown in FIG. 29. The pump 90 in this embodiment has a hose (not shown) that functions as the air output 81, as described above. Additionally, the pump 90 has an attachment mechanism 91 that is configured to releasably attach the pump 90 to a structure 92, such as a railing of the bed 12. The use of the attachment mechanism 91 may prevent the pump 90 from moving around during use and potentially dislodging the air output 81 from the port 80 and may keep the pump 90 out of the way of caregivers who may try to maneuver around the bed 12 to deliver care to the patient 70. In the embodiment of FIG. 29, the attachment mechanism 91 is a T-shaped bar that is connected to the pump by a hinge 93 and has two arms 94 with hooks 95 at the ends thereof. These hooks 95 allow either arm to be connected to a structure 92 to hang the pump 90 from the structure 92, as shown in FIG. 29. In other embodiments, the pump 90 may include a differently configured attachment mechanism 91.

Figure 27:
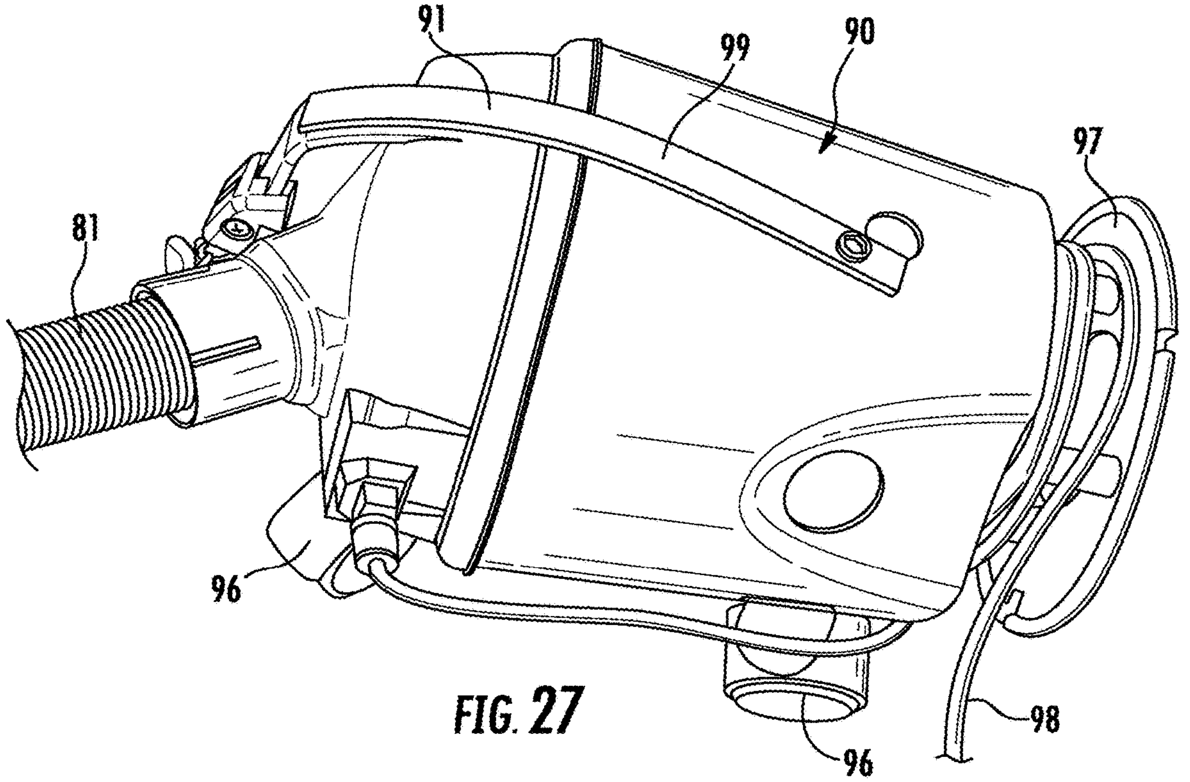
FIG. 27 is a perspective view of a pump according to aspects of the present disclosure.
Figure 28:
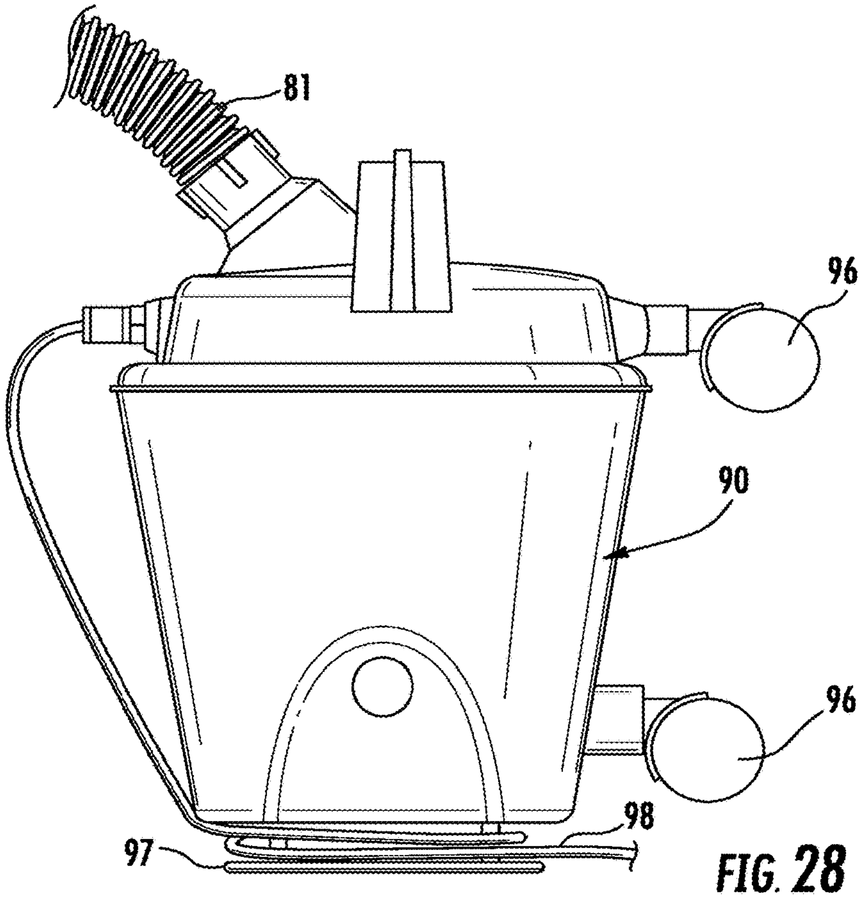
FIG. 28 is a side view of the pump of FIG. 27.

Another embodiment of the pump 90 is shown in FIGS. 27-28. In this embodiment, the pump 90 is configured for sitting on the floor or other surface in multiple different configurations. The pump 90 in FIGS. 27-28 includes wheels 96 for mobility, and the wheels 96 are placed along the longest dimension of the pump 90, such that the pump 90 is configured to sit in a low-profile configuration when sitting on the wheels 96. This low-profile configuration may permit the pump 90 to sit under the bed 12 and out of the way when not in use. The pump 90 also includes a standing base 97 configured to support the pump 90 in a standing configuration so that the wheels 96 do not contact the ground and the pump 90 does not move freely. The base 97 may also be configured to provide a structure for the power cord 98 to wrap around, as shown in FIGS. 27-28. The pump 90 may further include a strap 99 for holding the air output hose 81 when not in use and/or to function as an attachment mechanism 91 for attachment to a structure 92, such as the bed 12. In another embodiment, the pump 90 may include a clip or other form of attachment (not shown) that can be used to hold the air output hose 81 in place This clip or attachment may be magnetic, so as to hold the air output hose 81 in place by attraction to a metal wire or other metallic material used in the air output hose 81. It is understood that in other embodiments, the pump 90 may include a combination of features of the embodiment in FIG. 29 and the embodiment in FIGS. 27-28, or may include additional features. For example, in other embodiments, the pump 90 of FIGS. 27-28 may include an attachment mechanism 91, such as a carabiner clip (not shown) or an attachment mechanism 91 configured as in the embodiment of FIG. 29, or the pump 90 of FIG. 29 may include wheels 96 or a standing base 97 as in the embodiment of FIGS. 27-28. As another example, the pump 90 may include one or more switches (not shown) for powering the pump 90 on/off and potentially other controls as well. Such a switch or switches may include one or more hard-wired switches and/or remote switches (e.g., an RF switch).

The body pad 40 is typically made from a different material than the device 20 and contains an absorbent material, along with possibly other materials as well. The pad 40 provides a resting surface for the patient, and can absorb fluids that may be generated by the patient. The pad 40 may also be a low-lint pad, for less risk of wound contamination, and is typically disposable and replaceable, such as when soiled. The top and bottom surfaces 42, 44 may have the same or different coefficients of friction. Additionally, the pad 40 illustrated in the embodiments of FIGS. 1-2 is approximately the same width and slightly shorter in length as the device 20, and both the device 20 and the pad 40 are approximately the same width as the bed 12 so that the edges 23 of the device 20 and the edges of the pad 40 are proximate the side edges of the bed 12, but may be a different size in other embodiments.

In one embodiment, the pad 40 may form an effective barrier to fluid passage on one side (e.g., the underside 44), in order to prevent the device 20 from being soiled, and may also be breathable, in order to permit flow of air, heat, and moisture vapor away from the patient and lessen the risk of pressure ulcers (bed sores). The device 20 (or at least the top sheet 26 thereof) may also be breathable to perform the same function, as described above. A breathable device 20 used in conjunction with a breathable pad 40 can also benefit from use with a LAL bed 12, to allow air, heat, and moisture vapor to flow away from the patient more effectively, and to enable creation of an optimal microclimate around the patient. The pad 40 may have differently configured top and bottom surfaces 42, 44, with the top surface 42 being configured for contact with the patient and the bottom surface 44 being configured for contact with the device 20.

The system 10 may include one or more wedges 50A-B that can be positioned under the device 20 to provide a ramp and support to slide and position the patient slightly on his/her side, as described below. FIGS. 2 and 6-8A illustrate example embodiments of wedges 50A-B that can be used in conjunction with the system 10. The wedge 50A-B has a body 56 that can be triangular in shape, having a base wall or base surface 51, a ramp surface 52 that is positioned at an oblique angle to the base wall 51, a back wall 53, and side walls 54. In this embodiment, the base wall 51 and the ramp surface 52 meet at an oblique angle to form an apex 55 at the front end 57 of the wedge 50A-B, and the back wall 53 is positioned opposite the front end 57 and the apex 55 and approximately perpendicular to the ramp surface 52. The apex 55 may be the smallest angle of any of the corners of the wedge 50A-B, in one embodiment. It is understood that the term "apex" does not necessarily imply that the surfaces (e.g., the base wall 51 and the ramp surface 52) directly join to form a point or an angular edge, and that the "apex" as described herein may be an identifiable surface (e.g., rounded, beveled, flattened, etc.). FIGS. 8B and 8C illustrate example embodiments of wedges 50A-B that have an apex 55 that is flattened or beveled (FIG. 8B) or significantly rounded (FIG. 8C). The side walls 54 in this embodiment are triangular in shape and join at approximately perpendicular angles to the base wall 51, the ramp surface 52, and the back wall 53. In this embodiment, the surfaces 51, 52, 53, 54 of the wedge body 56 are all approximately planar when not subjected to stress, but in other embodiments, one or more of the surfaces 51, 52, 53, 54 may be curved or rounded. FIG. 8D illustrates an example embodiment of a wedge 50A-B where the ramp surface 52 has a curved contour. Any of the edges between the surfaces 51, 52, 53, 54 of the wedge body 56 may likewise be curved or rounded, including at the apex 55.

The wedge body 56 in this embodiment is at least somewhat compressible or deformable, in order to provide greater patient comfort and case of use. Any appropriate compressible material may be used for the wedge body 56, including various polymer foam materials, such as a polyethylene and/or polyether foam. A particular compressible material may be selected for its specific firmness and/or compressibility, and in one embodiment, the wedge body 56 is made of a foam that has relatively uniform compressibility. In another embodiment, the wedge body 56 may be made partially or completely from a different material, including substantially non-compressible materials. For example, the wedge body 56 may be made entirely from a substantially non-compressible material, or the wedge body 56 may have a substantially non-compressible core with a shell of a compressible material around the core, in various embodiments.

The wedge 50A-B is configured to be positioned under the device 20 and the patient, to position the patient at an angle, as described in greater detail below. In this position, the base wall 51 of the wedge 50A-B faces downward and engages or confronts the supporting surface 16 of the bed 12, and the ramp surface 52 faces toward the device 20 and the patient and partially supports at least a portion of the weight of the patient. The angle of the apex 55 between the base wall 51 and the ramp surface 52 influences the angle at which the patient is positioned when the wedge 50A-B is used. In one embodiment, the angle between the base wall 51 and the ramp surface 52 may be up to 45°, or between 15° and 35° in another embodiment, or about 30° in a further embodiment, as shown in FIG. 8A. Positioning a patient at an angle of approximately 30° is currently clinically recommended, and thus, a wedge 50A-B having an angle of approximately 30° may be the most effective for use in positioning most immobile patients. If clinical recommendations change, then a wedge 50A-B having a different angle may be considered to be the most effective. The wedge 50A-B may be constructed with a different angle as desired in other embodiments. It is understood that the device 20 may be usable without the wedges 50A-B, or with another type of wedge, including any commercially available wedges, or with pillows in a traditional manner. For example, the device 20 may be usable with a single wedge 50A-B having a greater length, or a number of smaller wedges 50A-B, rather than two wedges 50A-B, in one embodiment. As another example, two wedges 50A-B may be connected together by a narrow bridge section or similar structure in another embodiment. It is also understood that the wedge(s) 50A-B may have utility for positioning a patient independently and apart from the device 20 or other components of the system 10, and may be used in different positions and locations than those described and illustrated herein.

In one embodiment, the wedges 50A-B may have a directionally-oriented material (e.g., a directional stitching material 45, directional glide material, etc.) covering at least a portion of the ramp surface 52, and potentially other surfaces as well. In the embodiments illustrated in FIGS. 2 and 6-8, the wedges 50A-B have the directional stitching material 45 covering the ramp surface 52. In another embodiment, the directional stitching material 45 may additionally or alternately cover the base wall 51, the back wall 53, and/or the side walls 54. The directional stitching material 45 in this embodiment forms an engagement member 62 (which may be referred to as a "ramp engagement member") of a selective gliding assembly 60 on the ramp surface 52. In this embodiment, the directional stitching material 45 on the ramp surface 52 has the axis B (along which gliding is resisted) extending between the side walls 54 and parallel to the front end 57 and/or the apex 55, as illustrated in FIG. 18. Accordingly, the axis A (along which gliding is allowed) extends perpendicular to the front end 57 and/or the apex 55 and parallel to the side walls 54 in this embodiment, as illustrated in FIG. 18. In this arrangement, the directional stitching material 45 resists movement of the wedges 50A-B in directions parallel to the ramp surface 52 and perpendicular to the side walls 54, as described in greater detail herein. Similarly, the directional stitching material 45 resists movement of another surface in contact with the directional stitching material 45 (e.g., the bottom surface 22 of the device 20) relative to the wedges 50A-B in directions along to the ramp surface 52 (i.e., parallel to the front end 57, the apex 55 and/or the back wall 51) and perpendicular to the side walls 54. The directional stitching material 45 also engages the engagement members 61 of the directional stitching material 45 on the bottom surface 22 of the device 20 to enhance the selective gliding effect of the selective gliding assembly. This arrangement is illustrated schematically in FIG. 18. The other surfaces (e.g., the base wall 51, the back wall 53, and the side walls 54) of the wedges 50A-B are covered by a wrapping material 43 in the embodiment of FIGS. 2 and 6-8. This wrapping material 43 may be a taffeta fabric or other suitable material. In another embodiment, one or more of these surfaces may not be covered by any material, so that the inner material of the wedges 50A-B is exposed, or one or more of these surfaces may be partially covered by a material.

In the embodiments illustrated in FIGS. 2 and 6-8, the wedges 50A-B also have engagement members 64 in the form of patches of a directional glide material 49 located on one or more surfaces. The wedges 50A,B illustrated in FIGS. 2 and 6-8 have engagement members 64 of the directional glide material 49 located on the ramp surface 52 and the base wall 51 (which may also be referred to as a "ramp engagement member" and a "base engagement member," respectively). In another embodiment, one of the wedges 50B may have an engagement member 64 of the directional glide material 49 located on the ramp surface 52, but not on the base wall 51. Each of the engagement members 64 in this embodiment have the directional glide material 49 oriented so that the direction C of allowed movement of another surface with respect to the base wall 51 or the ramp surface 52 extends from the front end 57 and/or the apex 55 toward the back wall 53, as illustrated in FIG. 18. For example, for a brushed nylon fiber material, the fibers would be angled toward the back wall 53, so that gliding over the engagement member 64 in the direction C from the front end 57 and/or the apex 55 toward the back wall 53 is free, while gliding in the opposite direction D from the back wall 53 toward the front end 57 and/or the apex 55 is resisted. It is understood that this gliding is explained above with respect to the movement of another surface in contact with the directional glide material 49 (e.g., the bottom surface 22 of the device 20 or the bed sheet 15) relative to the wedge 50A-B. This same directional relationship can alternately be expressed as resisting movement of the wedge 50A-B with respect to the other surface in a direction from the front end 57 and/or the apex 55 toward the back wall 53 (e.g., resisting the wedge 50A-B from moving away from the patient), while allowing free gliding of the wedge 50A-B with respect to the other surface in a direction from the back wall 53 toward the front end 57 and/or the apex 55 (e.g., allowing easy insertion of the wedge 50A-B beneath the device 20).

Figure 7:
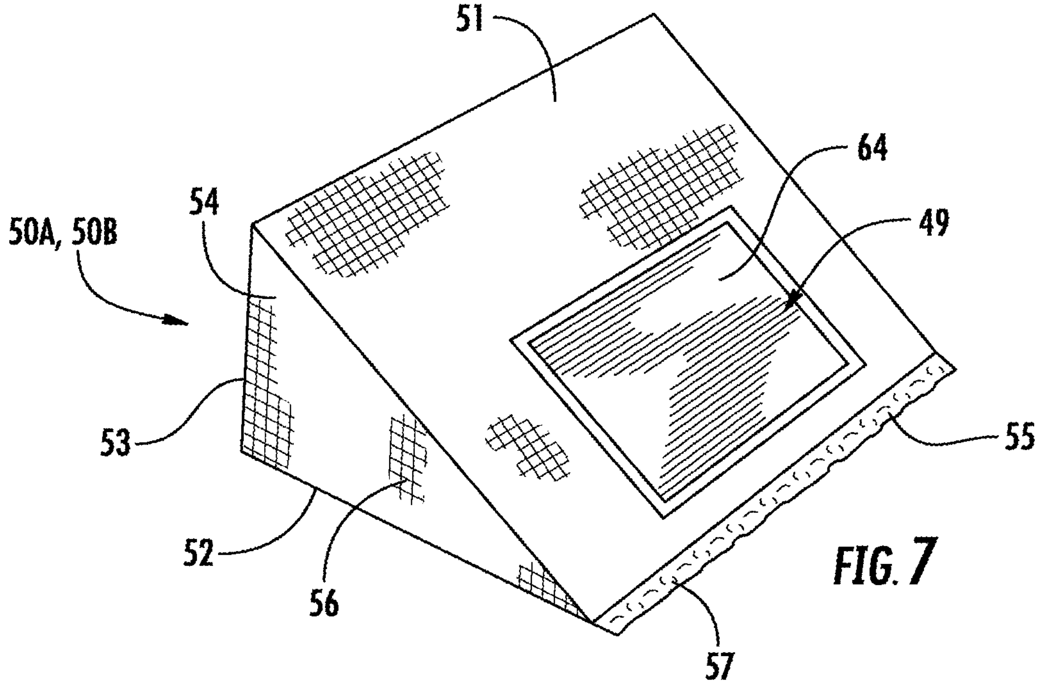
FIG. 7 is a bottom perspective view of a wedge of the system of FIG. 1.
Figure 8:
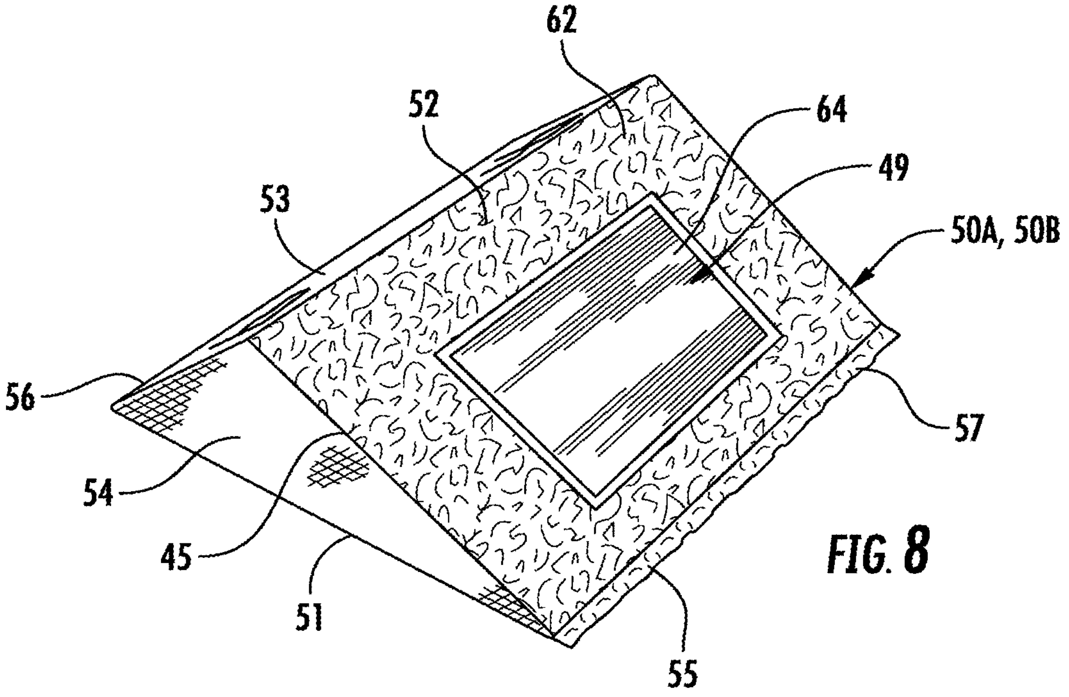
FIG. 8 is a top perspective view of the wedge of FIG. 7.
Figure 8A:
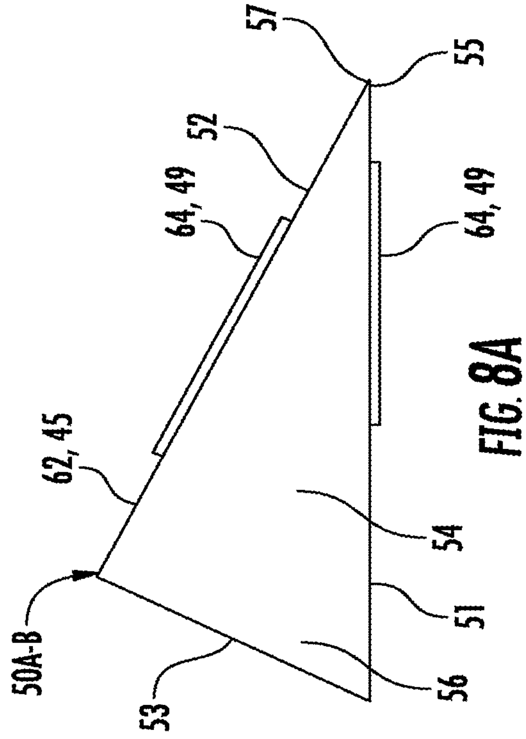
FIG. 8A is a side view of the wedge of FIG. 7.
Figure 8B:
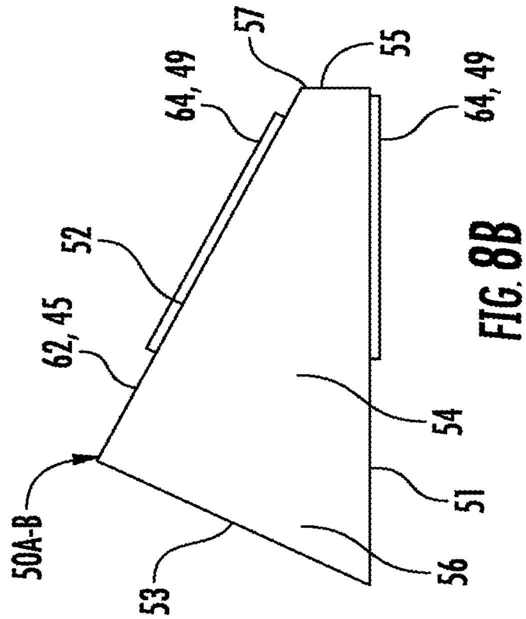
FIGS. 8B-8D are side views of additional embodiments of a wedge that is usable in connection with the system of FIG. 1.
Figure 8C:
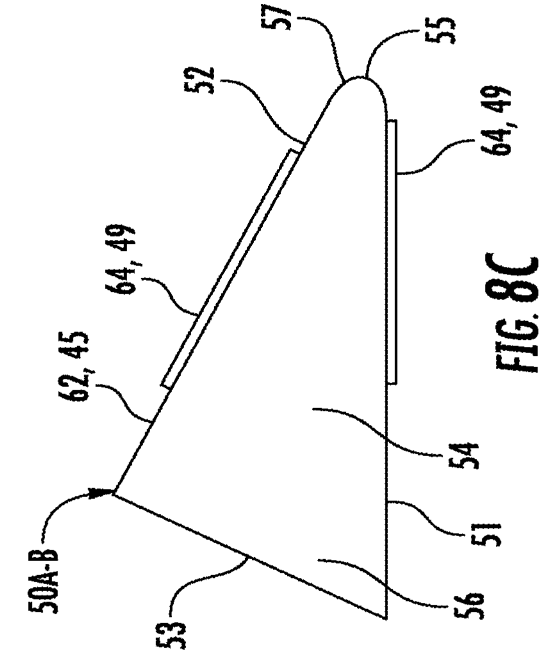
Figure 8D:
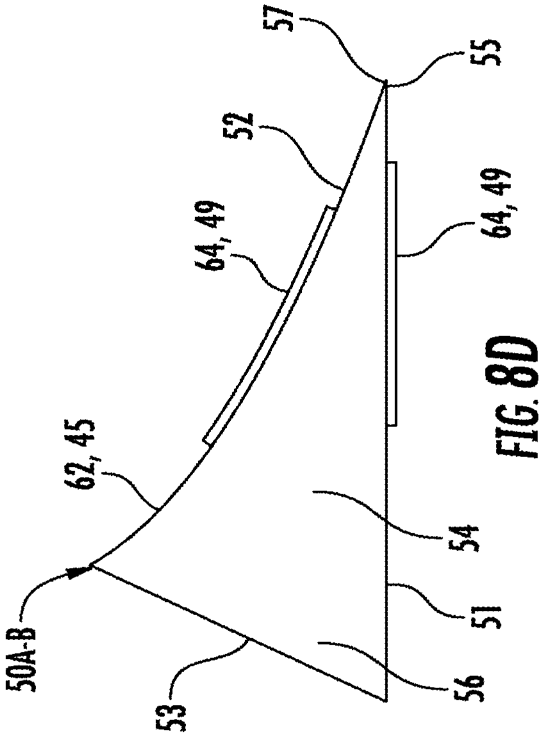

In the embodiments illustrated in FIGS. 2 and 6-8, the patches of the directional glide material 49 covered only a portion of the surfaces 51, 52 on which they were located, such that the edges of the directional glide material 49 are spaced from the edges of the respective surfaces on which they are located. In this configuration, the amount of the directional glide material 49 is sufficient to provide good resistance to unwanted slipping, but is not excessively expensive and leaves part of the directional stitching material 45 on the ramp surface 52 exposed to provide further functionality. For example, in one embodiment, the directional glide material 49 may cover approximately 20-40% of the surface area of the respective surface on which it is disposed, and in another embodiment, the directional glide material 49 may cover approximately 25-30% of the respective surface. In other embodiments, the directional glide material 49 may be located, sized, and/or oriented differently, and generally cover at least a portion of the surfaces on which they are located. Additionally, each of the patches of the directional glide material 49 may have a border to help resist abrasion, fraying, and or other wear, as shown in FIGS. 7-8. Such a border may be created by stitching (e.g., serge stitch), addition of a durable material, or other technique. Further, each of the patches of the directional glide material 49 may be connected to the wedge 50A-B by stitching, adhesive or other bonding, and/or other techniques. The engagement members 64 may have other configurations in other embodiments, including using different types of directionally-oriented materials.

As described above, the engagement members 62 of the directional stitching material 45 on the ramp surfaces 52 of the wedges 50A-B engage the engagement members 61 of the directional stitching material 45 on the bottom surface 22 of the device 20 to enhance the selective gliding effect of the selective gliding assembly 60. This engagement resists movement of the device 20 with respect to the wedges 50A-B along the axis B, and particularly, in the direction from the top edge 23 to the bottom edge 23 of the device 20, or in other words, from the head 13 to the foot 17 of the bed 12. In one embodiment, the directional stitching material 45 sliding upon another piece of the same material provides a resistance to sliding along the axis B on both pieces of material that is at least 3× greater (e.g., 3.6× in one embodiment) than the resistance to sliding along the axis A on both pieces of material. In other embodiments, the directional stitching material 45 sliding upon another piece of the same material provides a resistance to sliding along the axis B on both pieces of material that is at least 2× greater, or at least 2.5× greater, than the resistance to sliding along the axis A on both pieces of material. These and all other relative measurements of resistance to sliding described herein may be calculated using ASTM D1894. Additionally, the engagement members 64 of the directional glide material 49 engage the engagement members 61 of the directional stitching material 45 on the bottom surface 22 of the device 20 to resist movement of the device 20 with respect to the wedges opposite to the direction C, from the back wall 53 toward the front end 57 and/or the apex 55 of the wedges 50A-B, or in other words, to resist sliding of the device 20 down the slope of the ramp surface 52. In one embodiment, the directional stitching material 45 sliding upon the directional glide material 49 along the axis A of the material 45 and in the direction D of the material 49 provides a resistance to sliding that is at least 3× greater (e.g., 3.5× in one embodiment) than the resistance to sliding along the axis A and in the direction C. In another embodiment, the directional stitching material 45 sliding upon the directional glide material 49 along the axis A of the material 45 and in the direction D of the material 49 provides a resistance to sliding that is at least 2× greater, or at least 2.5× greater, than the resistance to sliding along the axis A and in the direction C. Additionally, in one embodiment, the directional stitching material 45 sliding upon the directional glide material 49 along the axis B of the material 45 (perpendicular to the directions C and D of the material 49) provides a resistance to sliding that is at least 3.5× greater (e.g., 4.1× in one embodiment) than the resistance to sliding along the axis A and in the direction C. In another embodiment, the directional stitching material 45 sliding upon the directional glide material 49 along the axis B of the material 45 (perpendicular to the directions C and D of the material 49) provides a resistance to sliding that is at least 2× greater, at least 2.5× greater, or at least 3× greater, than the resistance to sliding along the axis A and in the direction C.

The combination of these engagements between the engagement members 61, 62, 64 creates a selective gliding assembly 60 with a "one-way" gliding arrangement between the device 20 and the wedges 50A-B, where the device 20 can only freely move in the direction C toward the back walls 53 of the wedges 50A-B, which allows the device 20 and the patient 70 to be pulled up onto the ramp surfaces 52 of the wedges 50A-B without resistance, as described herein. The engagement member 64 of the directional glide material 49 on the base wall 51 of the wedge 50A,B also resists sliding of the wedge 50A, B away from the front end 57 and/or the apex 55, or in other words, resists sliding of the wedge 50A,B out from underneath the device 20. In one embodiment, the directional glide material 49 sliding against a typical bed sheet material in the direction D provides a resistance to sliding that is at least 2.5× greater (e.g., 2.9× in one embodiment) than the resistance to sliding in the direction C. Additionally, in one embodiment, the directional glide material 49 sliding against a typical bed sheet material perpendicular to the directions C and D (i.e. toward the foot 17 of the bed 12) also provides a resistance to sliding that is at least 2.5× greater (e.g., 2.5× in one embodiment) than the resistance to sliding in the direction C. The base walls 51 of the wedges 50A-B may also include a material or feature to offer some resistance to sliding of the wedges 50A-B along the axis B in one embodiment, and particularly, in the direction from the top edge 23 to the bottom edge 23 of the device 20, or in other words, from the head 13 to the foot 17 of the bed 12. For example, a directional stitching material 45 or another directionally-oriented material may be used for this purpose. The resistance to sliding provided by such material may be less than the resistance of the selective gliding assemblies 60 between the device 20 and the ramp surfaces 52 of the wedges 50A-B, such that the device 20 will not be encouraged to slide relative to the wedges 50A-B, and the device 20, the pad 40, the wedges 50A-B, and the patient 70 may move together without slipping relative to one another.

As described herein, the selective gliding assemblies 60 can resist movement in one or more directions and allow free movement in one or more different directions, which may be transverse or opposed to each other. It is understood that the "resistance" to sliding may be expressed using a difference in pull force necessary to create sliding movement between the same pieces of material in different directions. For example, if a selective gliding assembly is considered to "resist" sliding in one direction and "allow" sliding in another direction, this may be determined by having a relatively greater pull force necessary to create sliding movement between two engaging materials in the former direction and a relatively smaller pull force necessary to create sliding movement between the same two materials in the latter direction. The difference in resistance may be expressed quantitatively as well, such as described elsewhere herein. In one embodiment, a selective gliding assembly 60 may resist movement in one direction and may allow movement in another direction that is opposed (i.e., angled 180° to) the first direction. In another embodiment, a selective gliding assembly 60 may resist movement in one direction and may allow movement in another direction angled 90° to the first direction. In a further embodiment, a selective gliding assembly 60 may allow movement in one direction and may resist movement in at least two other directions angled 90° and 180° to the first direction. Still further types of directional gliding assemblies 60 may be constructed using materials as described herein and/or additional materials with directional properties.

In other embodiments, the apparatus 10 may include a different type of supporting device other than the wedges 50A-B illustrated in FIGS. 2 and 6-8, such as a different type or configuration of wedge or a different type of supporting device. For example, the wedges 50A-B may be joined together to form a single wedge in one embodiment, which may include a gap at the sacral area. As another example, the system 10 may include a supporting device in the form of a pillow or cushion. It is understood that any supporting device for turning patients 70 that may be included with the system 10 may include any of the features of the wedges 50A-B described herein, including the engagement members 62, 64 for forming selective glide assemblies 60.

FIGS. 20-24 illustrate another embodiment of an inflatable patient support device 20 for use in connection with a system or apparatus 10 as described above. It is understood that the device 20 in FIGS. 20-24 may be used in connection with the wedges 50A-B, the absorbent body pad 40, and other components of the system 10 as described elsewhere herein, and the use of the device 20 of FIGS. 20-24 in connection with these other components is not illustrated or described in detail herein for the sake of brevity. Additionally, the device 20 of FIGS. 20-24 includes many components and features that are similar or identical to the components and features of the device 20 described herein with respect to other embodiments, e.g., the embodiment in FIGS. 1-13. Such similar or identical components are referred to using similar reference numbers and may not be described again in detail with respect to FIGS. 20-24, for the sake of brevity. Thus, it is understood that the device 20 in FIGS. 20-24 may include any of the components, features, or variations thereof described elsewhere herein with respect to other embodiments.

Figure 23:
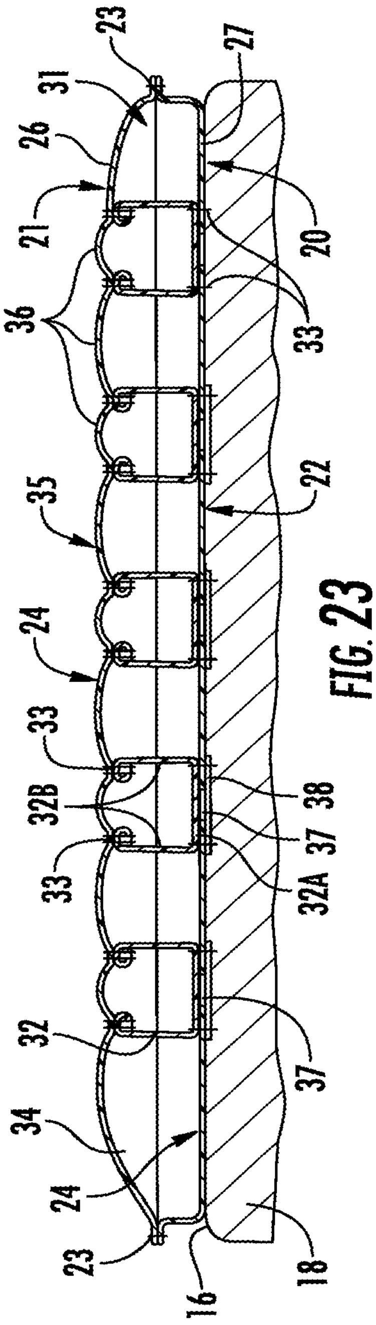
FIG. 23 is a cross-section view of the device of FIG. 20.

The top and bottom sheets 26, 27 of the device 20 in the embodiment of FIGS. 20-24 have rectangular shapes, giving the device 20 a rectangular outer shape, such that the head edge 23 is straight, rather than angular in shape. The device 20 of FIGS. 20-24 has the gusset 32 most proximate to the head edge 23 of the device 20 spaced more closely to the head edge 23, as compared the similarly-positioned gusset 32 in the embodiment of FIGS. 1-13. As a result, the device 20 in FIGS. 20-24 undergoes a comparatively smaller degree of inflation near the head edge 23, as shown in FIG. 23, creating a sloping shape between the head edge 23 and the closest gusset 32 when the device is inflated. This configuration permits the patient's head to rest more comfortably and naturally on the device 20.

The device 20 in the embodiment of FIGS. 20-24 is smaller than the device 20 in FIGS. 1-13, allowing greater freedom of movement of the device 20 and the patient when placed on a bed 12. Fewer gussets 32 are included in this embodiment relative to the device of FIGS. 1-13, due at least partially to the smaller size. As illustrated in FIGS. 20-23, the device has five gussets 32 and ten total gusset arms 32B, as opposed to the seven gussets 32 and fourteen total gusset arms 32B in the embodiment of FIGS. 1-13. The heights of the gusset arms 32B are also smaller in the embodiment of FIGS. 20-24, relative to the embodiment of FIGS. 1-13, creating a shorter inflation height and a relatively larger peripheral cushion 34, which may improve stability. The spacing between the gussets 32 in the embodiment of FIGS. 20-24 is equal or substantially equal to the spacing between the gusset arms 32B (i.e., the width of the gusset bases 32A). Additionally, the lateral ends of the gussets 32 in the embodiment of FIGS. 20-24 are spaced inwardly from the side edges 23 of the device 20 to create the peripheral cushion 34, as in the embodiment of FIGS. 1-13. The device 20 in the embodiment of FIGS. 20-24 includes four covers 38, with one cover 38 positioned over each of four passages 37. The covers 38 in this embodiment are made of an air-permeable material with directional friction properties (e.g., a directional glide material 45), and the covers 38 may have any or all of the capabilities identified herein with respect to the covers 38 in FIGS. 1-13, including the ability to function as engagement members 61 for a selective gliding assembly 60.

The passages 37 in the device 20 of FIGS. 20-24 are diamond-shaped or otherwise tapered in width from the center of each passage 37 to the ends of the passage 37, similar to the configuration shown in FIG. 17. In another embodiment, the passages 37 may have a different shape (i.e., other than a diamond) that has a width that is greater proximate the center of the device 20 and smaller proximate the side edges 23 of the device 20. Such a tapered-width configuration assists in airflow control, to prevent excess air loss when lifting of the side edges 23 of the device 20. Normally, the passages 37 are pressed against the supporting surface 16 of the bed 12, which limits airflow through the passages 37 to maintain inflation of the device 20. When a portion of the device 20 is lifted, part of the passage 37 will not be covered by any surface, allowing increased airflow through the passage 37. When the passages 37 have a tapered width as shown in FIGS. 20-24, lifting a portion of the device 20 near one of the side edges 23 (which is frequently done during use, such as to insert the wedges 50A-B) will only uncover a small area of the passage 37, thus limiting air escape. At the same time, the overall size of the passage 37 provides the desired overall level of airflow through the passage 37 to ensure proper inflation and a suitable air cushion for moving the device 20. Additionally, the device 20 in FIGS. 20-24 has larger passages 37 in the area configured to be positioned under the upper body and torso of the patient and smaller passages 37 in the areas configured to be positioned under the head and the lower body of the patient. As described above, this creates a passage 37 configuration with a greater aggregate surface area of passages 37 in the areas designed to be positioned beneath the upper body and torso of the patient 70, as these areas will typically support greater weight and can benefit from an increased volume of air forming the air cushion in those areas.

The structure and function of the device 20 in FIGS. 20-24 is, in other aspects, generally similar to the structure and function of the other embodiments in FIGS. 1-19 described herein. In particular, the device 20 in FIGS. 20-24 is configured for use with the wedges 50A-B and the pump 90 in the same manners described elsewhere herein.

Figure 26:
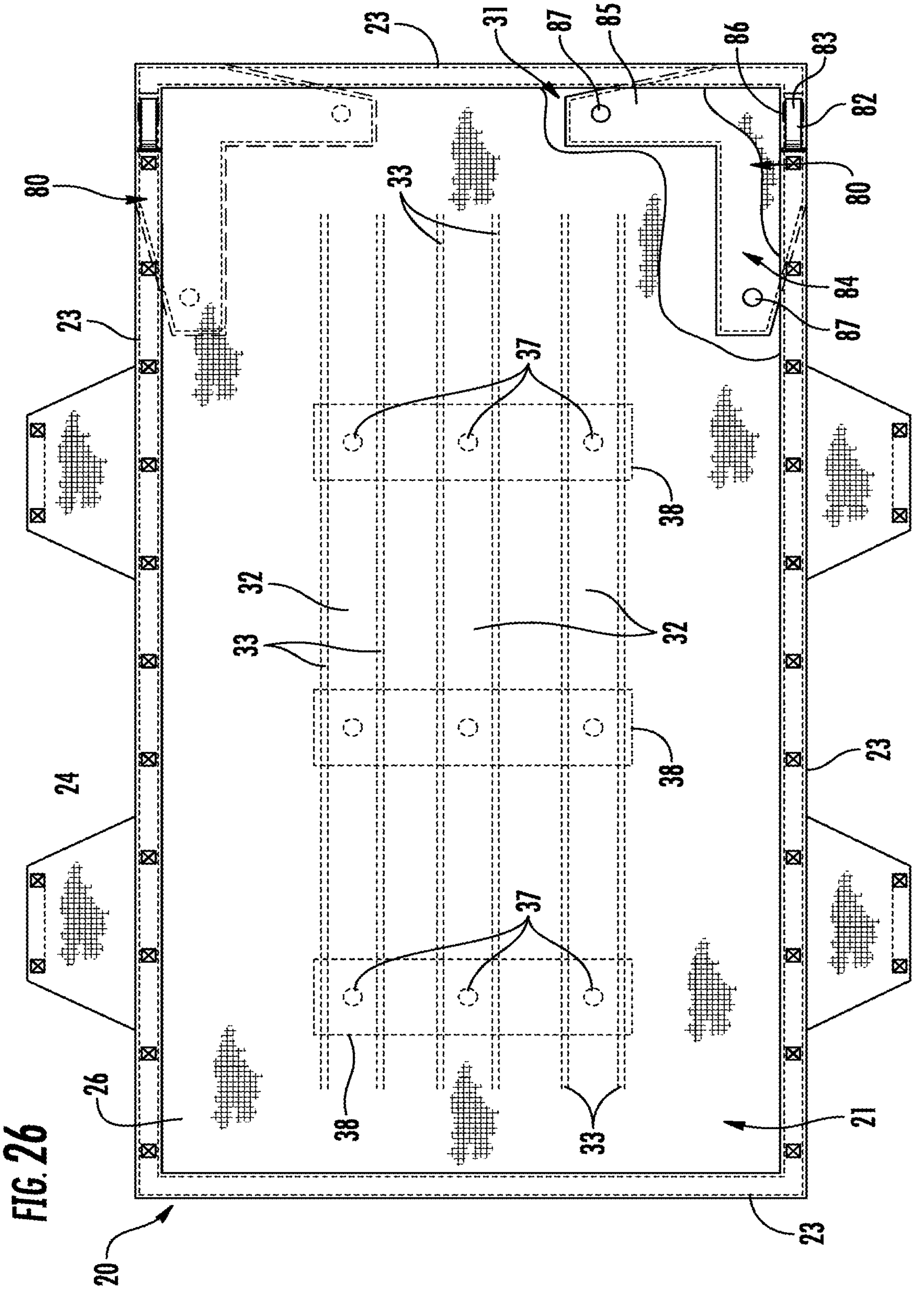
FIG. 26 is a top view of another embodiment of a device for use with a system for turning and positioning a patient, according to aspects of the disclosure.

FIG. 26 illustrates another embodiment of an inflatable patient support device 20 for use in connection with a system 10 as described above. It is understood that the device 20 in FIG. 26 may be used in connection with the wedges 50A-B, the absorbent body pad 40, and other components of the system 10 as described elsewhere herein, and the use of the device 20 of FIG. 26 in connection with these other components is not illustrated or described in detail herein for the sake of brevity. Additionally, the device 20 of FIG. 26 includes many components and features that are similar or identical to the components and features of the device 20 described herein with respect to other embodiments, e.g., the embodiments in FIGS. 1-13 and FIGS. 20-24. Such similar or identical components are referred to using similar reference numbers and may not be described again in detail with respect to FIG. 26, for the sake of brevity. Thus, it is understood that the device 20 in FIG. 26 may include any of the components, features, or variations thereof described elsewhere herein with respect to other embodiments.

The device 20 in FIG. 26 has gussets 32 that extend lengthwise in the head-to-foot direction (i.e., substantially parallel to the side edges 23), rather than in the lateral (side-to-side) direction as in the embodiments of FIGS. 1-17 and 20-24. The device 20 in this embodiment has three gussets 32 with a total of six gusset arms 32B extending between the top and bottom sheets 26, 27. The total area covered by the gussets 32 and the spacing between the gussets 32 and the edges 23 of the device 20 in the embodiment of FIG. 26 are similar to that of the embodiment in FIGS. 20-24, such that a peripheral cushion 34 of similar size is formed around the central area 35. Additionally, the gussets 32 are closer to the head edge 23 than the foot edge 23 in the embodiment of FIG. 26, in order to form a sloping shape between the head edge 23 and the ends of the gussets 32 when the device 20 is inflated.

The device 20 in the embodiment of FIG. 26 has passages 37 that are positioned beneath the bases 32A of the gussets 32, so that the gussets 32 cover the passages 37 as in the embodiments of FIGS. 1-13 and 20-24 described above. The passages 37 in this embodiment are illustrated as round passages 37 arranged in lateral rows, similar to the passages 37 in the embodiment of FIGS. 1-13. In other embodiments, the passages 37 may be shaped and/or placed in a different configuration, and additional pieces 47 of air permeable material may be used to cover the passages 37 or portions of the passages 37 as necessary, such as shown in FIG. 25. For example, the gussets 32 may not include bases 32A in one embodiment, and any or all of the passages 37 may be covered with additional pieces 47 of air permeable material. The device 20 in the embodiment of FIG. 26 also has air permeable covers 38 on the bottom surface 22 covering all of the passages 37, with each cover 38 extending laterally to cover a row of three passages 37. The covers 38 in the embodiment of FIG. 26 may have any or all of the capabilities identified herein with respect to the covers 38 in FIGS. 1-13 and 20-24, including the ability to function as engagement members 61 for a selective gliding assembly 60.

The structure and function of the device 20 in FIG. 26 is, in other aspects, generally similar to the structure and function of the other embodiments in FIGS. 1-25 described herein. In particular, the device 20 in FIG. 26 is configured for use with the wedges 50A-B and the pump 90 in the same manners described elsewhere herein.

FIGS. 30-35 illustrate another embodiment of an inflatable patient support device 20 for use in connection with a system 10 as described herein. It is understood that the device 20 in FIGS. 30-35 may be used in connection with the wedges 50A-B, the absorbent body pad 40, and other components of the system 10 as described elsewhere herein, and the use of the device 20 of FIGS. 30-35 in connection with these other components is not illustrated or described in detail herein for the sake of brevity. Additionally, the device 20 of FIGS. 30-35 includes many components and features that are similar or identical to the components and features of the device 20 described herein with respect to other embodiments, e.g., the embodiments in FIGS. 1-13 and FIGS. 20-26. Such similar or identical components are referred to using similar reference numbers and may not be described again in detail with respect to FIGS. 30-35, for the sake of brevity. Thus, it is understood that the device 20 in FIGS. 30-35 may include any of the components, features, or variations thereof described elsewhere herein with respect to other embodiments. For example, it is understood that the embodiment of FIGS. 30-35 is similar or identical to the embodiment of FIGS. 20-24 in structure and function except as otherwise described herein.

Figure 33:
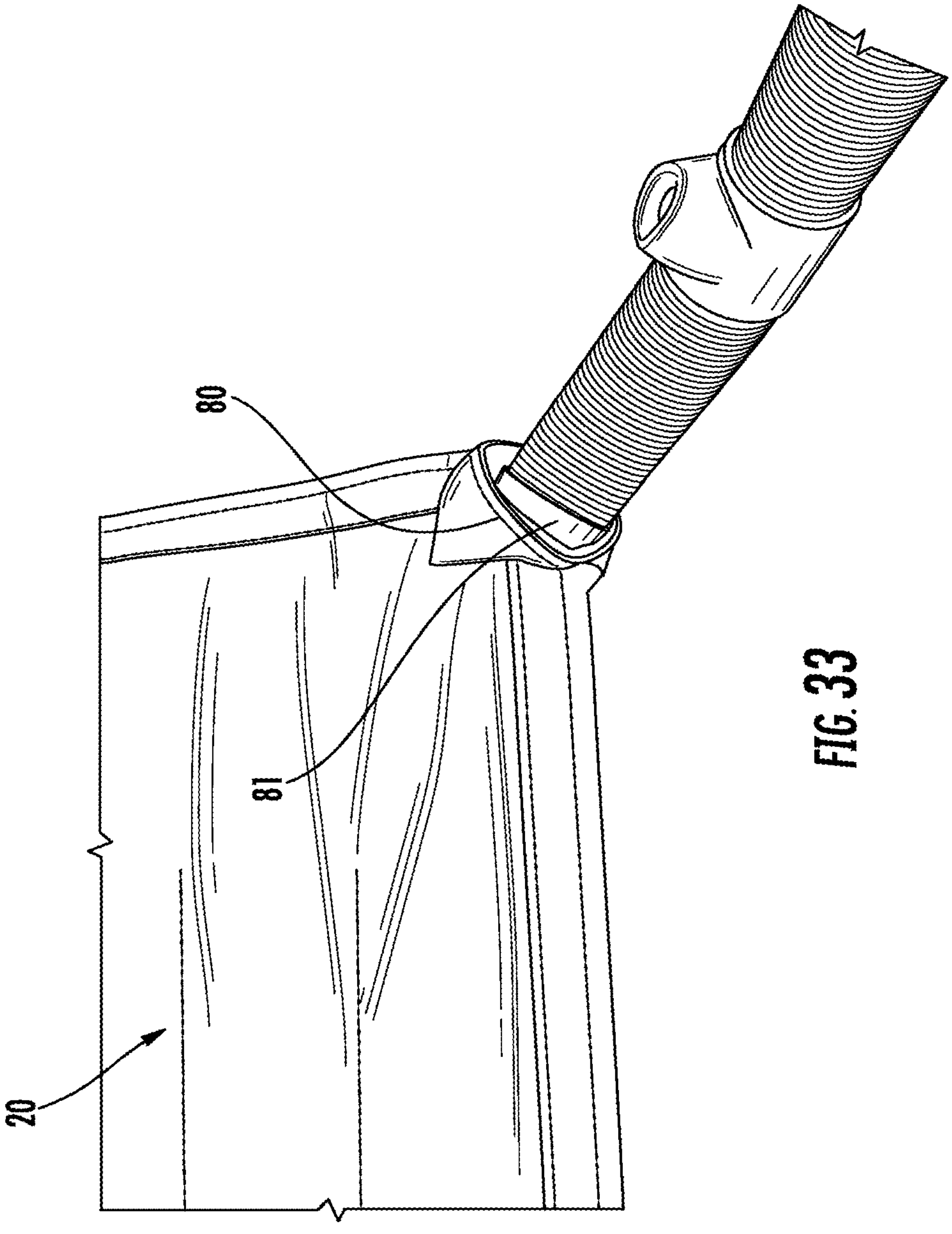
FIG. 33 is a top plan view of an air output connected to the port of FIG. 32.
Figure 34:
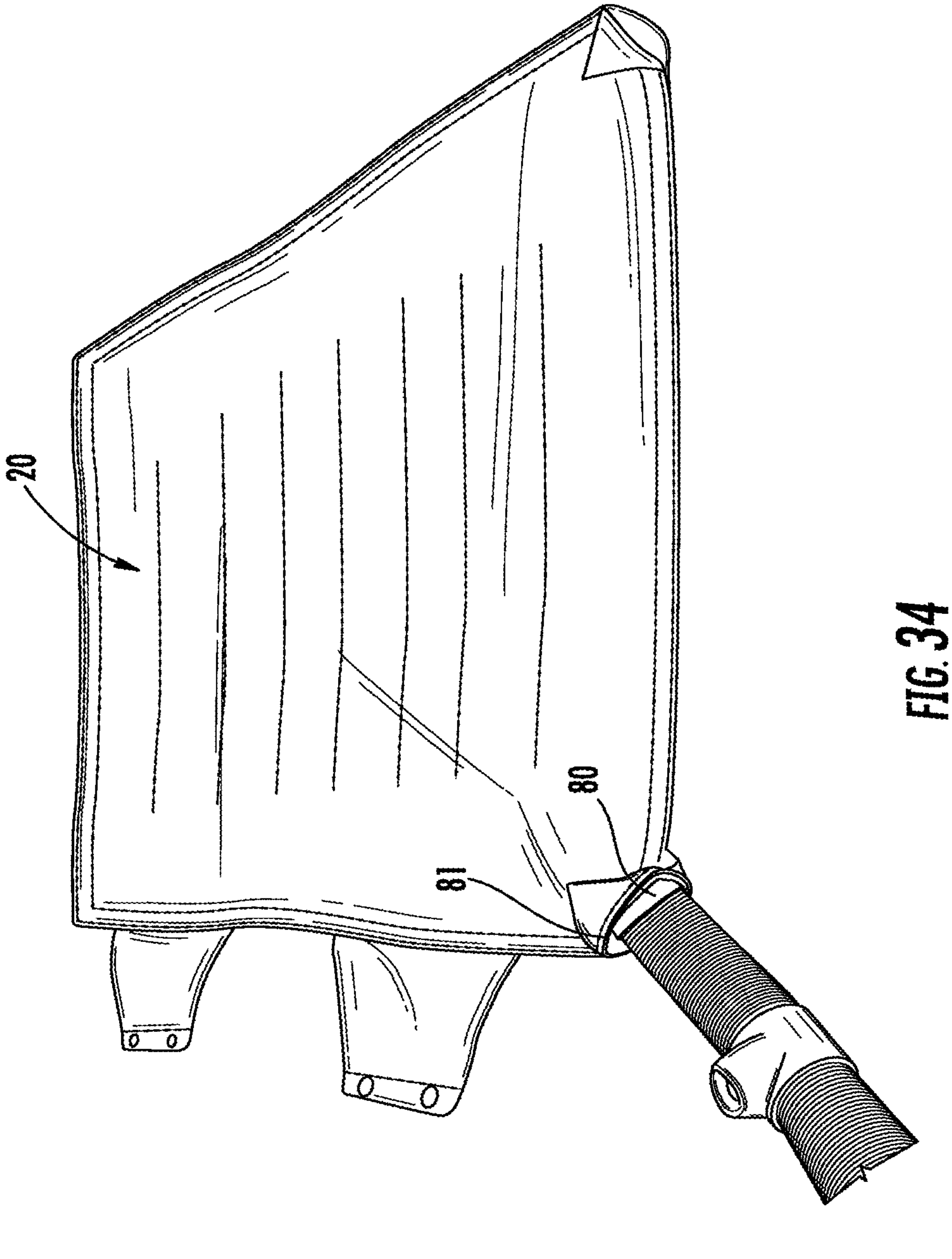
FIG. 34 is a top plan view of the air output of FIG. 33 connected to a second port of the device of FIG. 30.

The device 20 in FIGS. 30-35 has inflation ports 80 that are located and configured differently in some aspects from the ports 80 described with respect to other embodiments herein. The ports 80 in FIGS. 30-35 are located at the corners where the left and right side edges 23 and the foot edge 23 of the device 20 meet, and the opening 82 of each port is formed across said corners at an angle. In the embodiment shown, the openings 82 are formed at 45° angles and extend inwardly at 45° angles, and the corners of the top sheet 26 and the bottom sheet 27 are folded inwardly onto the top and bottom surfaces 21, 22 of the device 20, respectively, to create this configuration. The retaining mechanism 83 in the embodiment of FIGS. 30-35 is a stretchable or elastic member that is located around at least a portion of each opening 82. The elastic member of the retaining mechanism 83 is schematically illustrated in broken lines in FIG. 32, and is provided in the form of an elastic ring, a compressible O-ring, or other such structure. Such an elastic member may be included in an annular pocket or cavity formed around the opening 82 by a separate piece 65 of sheet material being stitched or otherwise connected around the opening 82. FIGS. 33-34 illustrate an air output 81 being inserted in the two openings 82 at the left and right corners of the device 20.

Figure 35:
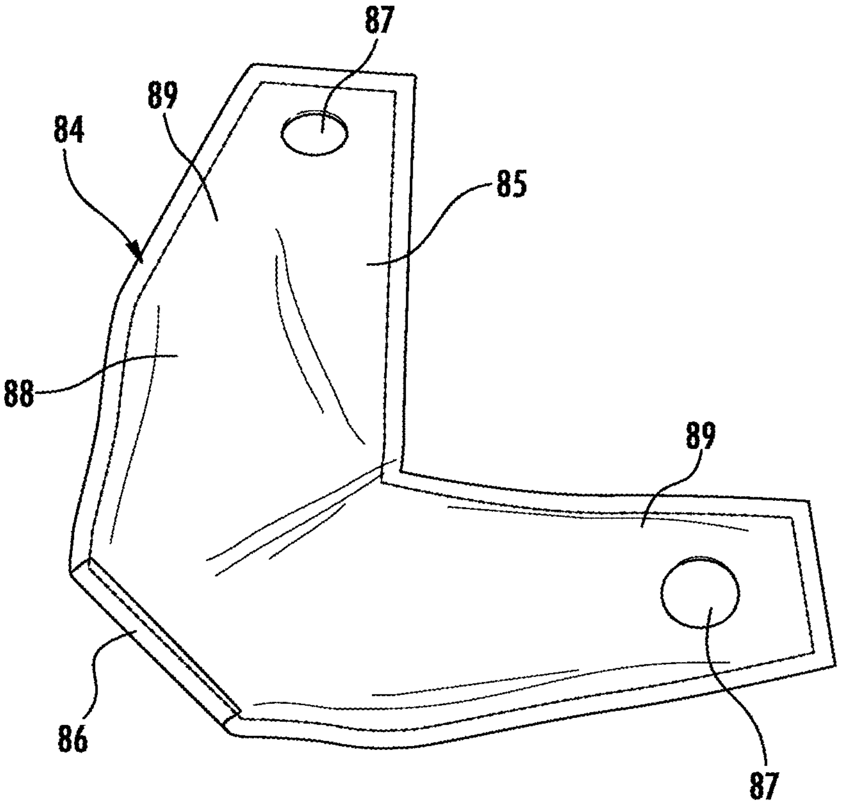
FIG. 35 is a top plan view of a pocket connected to the port of the device of FIG. 30.

The device 20 in FIGS. 30-35 also includes a valve 84 that is constructed similarly to the valve 84 of the embodiment of FIGS. 3-5 and 9 and the embodiment of FIGS. 20-24 discussed above, and this valve 84 may include any of the features (including alternate features) described above with respect to those embodiments. The valve 84 in this embodiment is illustrated in FIG. 35 and is formed by a pocket 85 that is positioned within the cavity 31 of the device 20 and has an entrance opening 86 in communication with the opening 82 of the port 80 and at least one exit opening 87 in communication with the cavity 31, as similarly described herein with respect to other embodiments. The entrance opening 86 in this embodiment is located at the corner of the pocket 85 in order to correspond to the location of the opening 82 on the device 20. The pocket 85 in the embodiment of FIG. 35 has two branches 89 extending away from each other, e.g., to form an L-shape, and the exit openings 87 are located near the ends of the branches 89 to space them from the entrance opening 86 and from each other. The pocket 85 in this embodiment is formed by one or more sheets 88 of flexible material that are folded and/or connected together to define the pocket 85 in the desired shape. In the embodiment of FIG. 35, the pocket 85 is stitched to the inside of the device 20 only around the port 80, and the rest of the pocket 85 is free within the cavity 31. The retaining mechanism 83 (elastic member) and the separate piece 65 of material positioned around each opening 82 are connected to the pockets 85 at the entrance openings 86 in this embodiment, although these structures may be connected directly to the top and/or bottom sheets 26, 27 in another embodiment. The valve 84 in the embodiment of FIG. 35 functions in substantially the same manner as the valve 84 described herein with respect to other embodiments.

All or some of the components of the system 10 can be provided in a kit, which may be in a pre-packaged arrangement, as described in U.S. Patent Application Publication No. 2012/0186012, published Jul. 26, 2012, which is incorporated by reference herein in its entirety and made part hereof. For example, the device 20 (deflated) and the pad 40 may be provided in a pre-folded arrangement or assembly, with the pad 40 positioned in confronting relation with the top surface 21 of the device 20, in approximately the same position that they would be positioned in use, and the device 20 and pad 40 can be pre-folded to form a pre-folded assembly. This pre-folded assembly can be unfolded when placed beneath a patient. It is understood that different folding patterns can be used. The pre-folded device 20 and pad 40 can then be unfolded together on the bed 12, as described below, in order to facilitate use of the system 10. Additionally, the device 20 and the pad 40 can be packaged together, by wrapping with a packaging material to form a package, and may be placed in the pre-folded assembly before packaging. The one or more wedges 50 and/or the pump 90 may also be included in the package, in one embodiment. Other packaging arrangements may be used in other embodiments.

Figure 36:
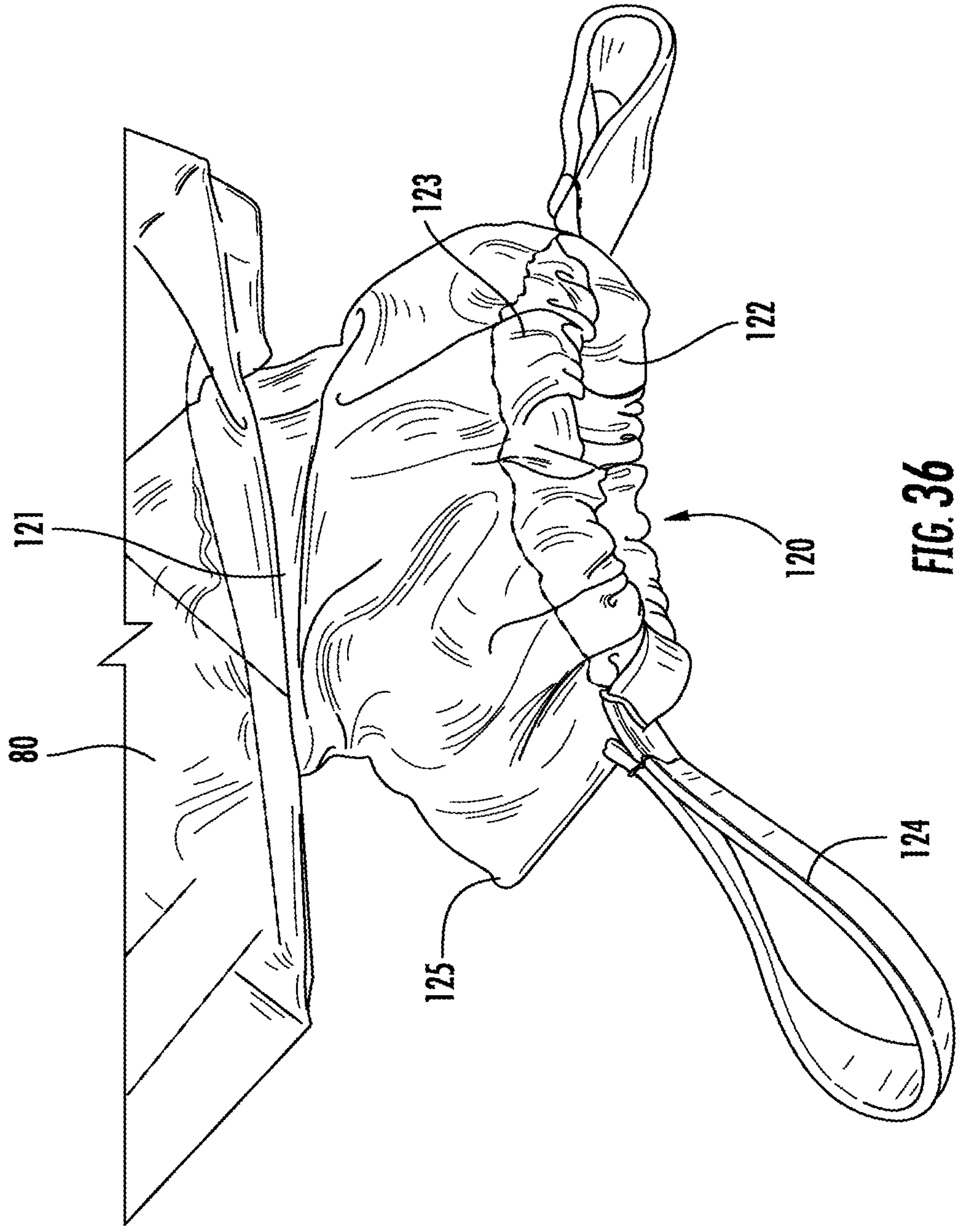
FIG. 36 is a top view of a port sock connected to the inflatable body of the device of FIG. 30
Figure 37:
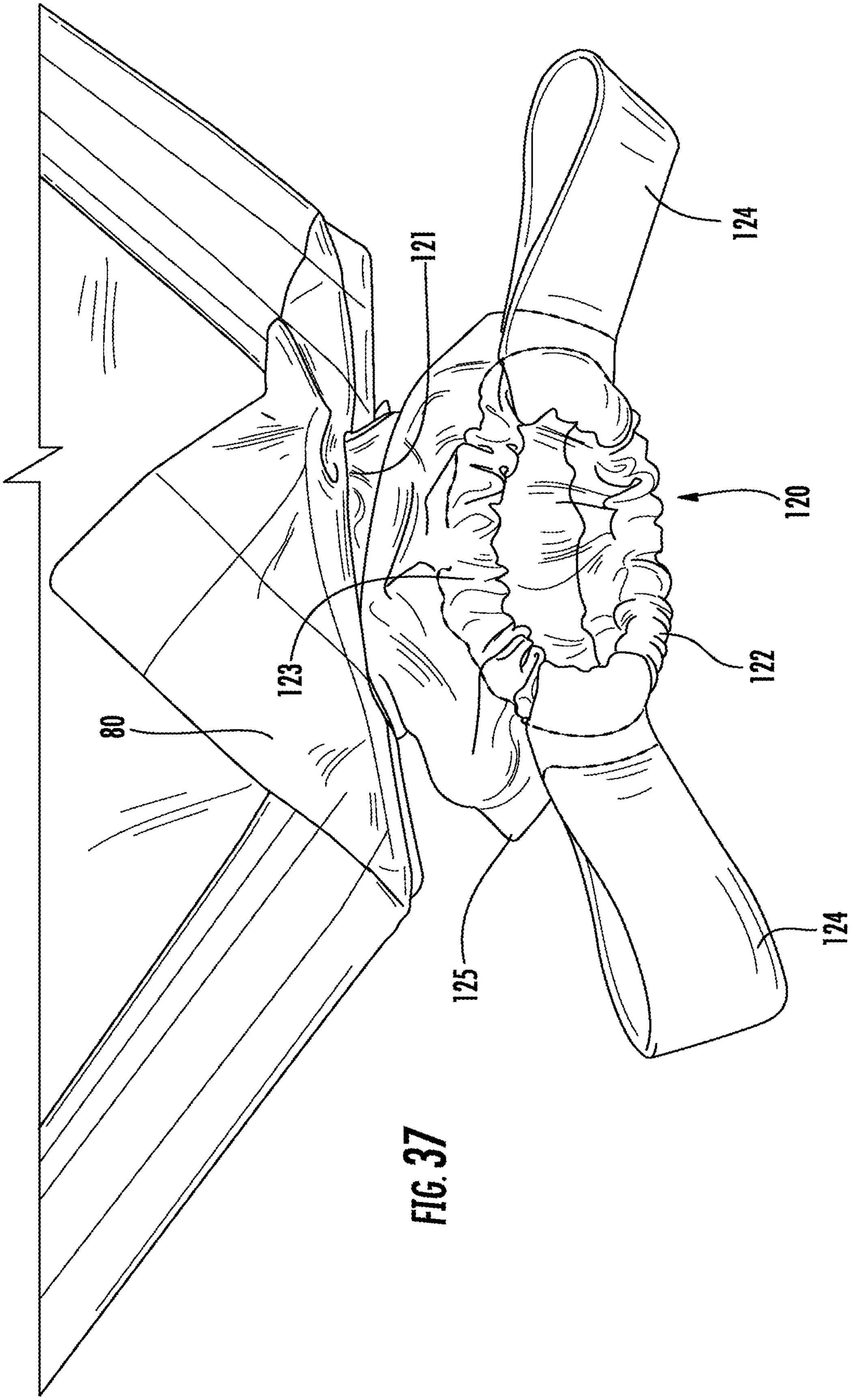
FIG. 37 is a front view of an opening of a port sock of FIG. 36 connected to the inflatable body of the device of FIG. 30.

As shown in FIGS. 36-37, the device 20 may also include a port sock 120 having a first opening 121 and a second port opening 122. The first opening 121 is configured to attach or connect to the inflatable body of the device 20 or to valves 84 (e.g., by sewing first opening 121 to ports 80 or to valves 84). The port sock 120 is connected to the device 20 in such a way that the port at second port opening 122 may not be flush with side and foot edges 23 of device 20. In other words, when port sock 120 is attached to device 20, port sock 120 may extend out from the device 20. Extending port sock 120 out from the device 20 prevents port sock 120 or port 80 from bunching up and ensures that device 20 remains flat. Port opening 122 of port sock 120 may have a retaining mechanism 123, which is provided in the form of an elastic ring. Side handles 124 (e.g., straps or tabs) are disposed at or along an edge of port opening 122 of port sock 120. Side handles 124 are configured to allow for pulling retaining mechanism 123 to stretch open port opening 122 so that a nozzle 81 can be inserted into port opening 122. Side handles 124 allow for easier insertion of a nozzle into port opening 122 without stretching port opening 122 to a completely unstretched state. Side handles 124 are also configured to allow for pulling retaining mechanism 123 to open port opening 122 such that the nozzle can be easily removed. Port sock 120 also includes side pouches 125 configured to engage with a nozzle 81 or an attachment to the nozzle 81, as described below. The side pouches 125 are a portion of the port sock 120 having an increased diameter relative to the port opening 121 and/or 122. In the embodiment shown, the side pouches 125 are two oppositely disposed peak-shaped portions, formed by an increase in diameter from the port opening 122 to a maximum pouch diameter, and then decreasing back down to the diameter of the port opening 121.

Figure 38:
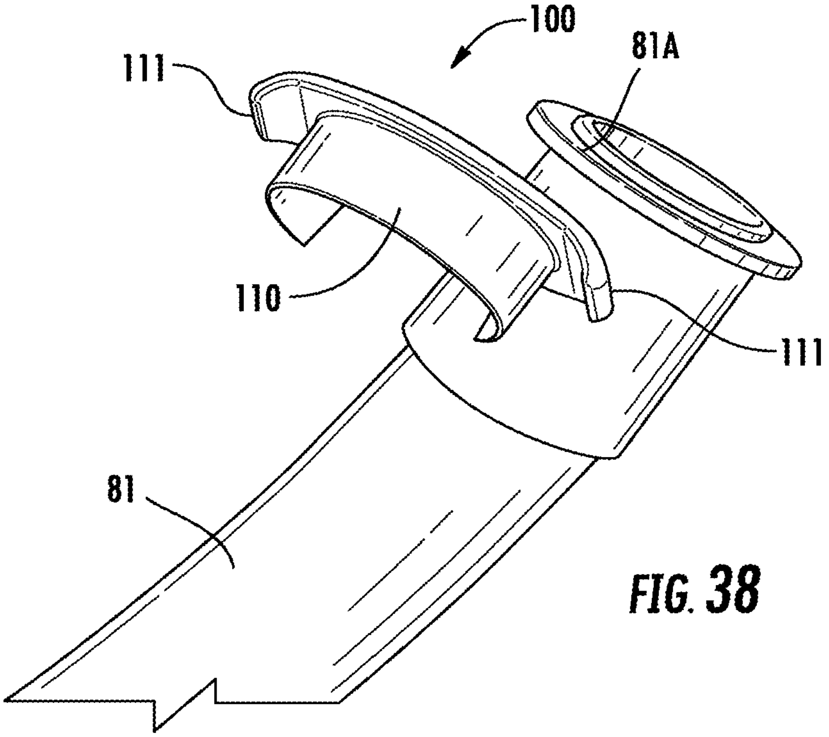
FIG. 38 is a perspective view of an exploded assembly of a nozzle and a C-shaped clip.
Figure 39:
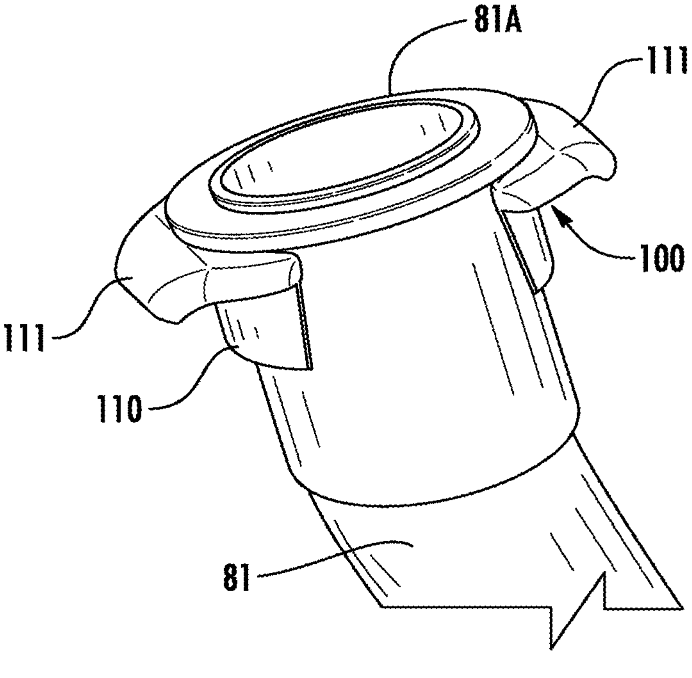
FIG. 39 is a perspective view of an assembly having a nozzle and a C-shaped clip installed on the nozzle.
Figure 40:
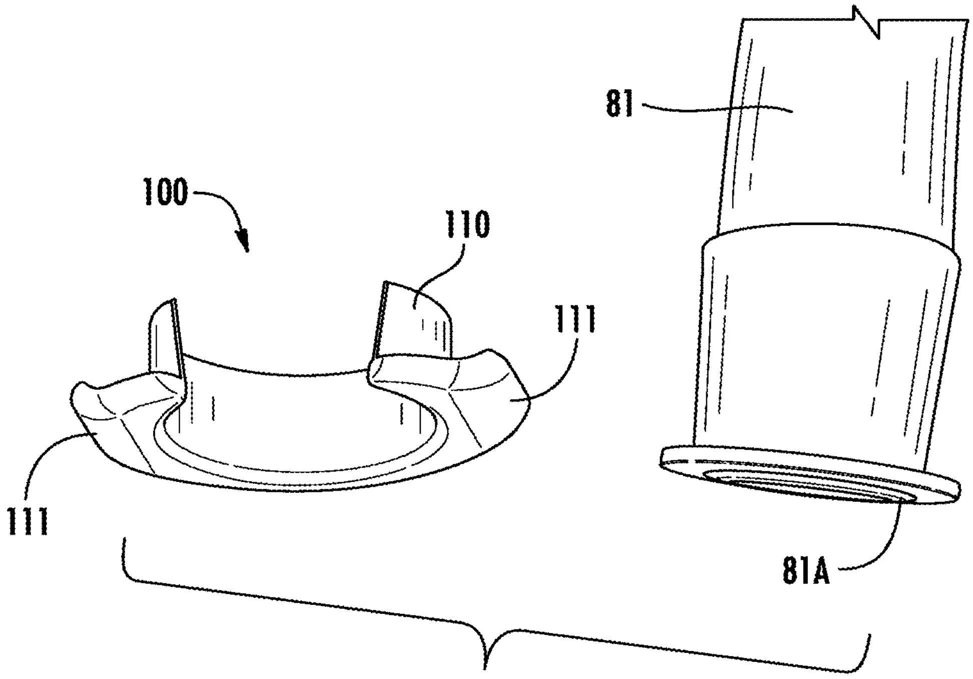
FIG. 40 is a top view of a nozzle, and a C-shaped clip.
Figure 41:
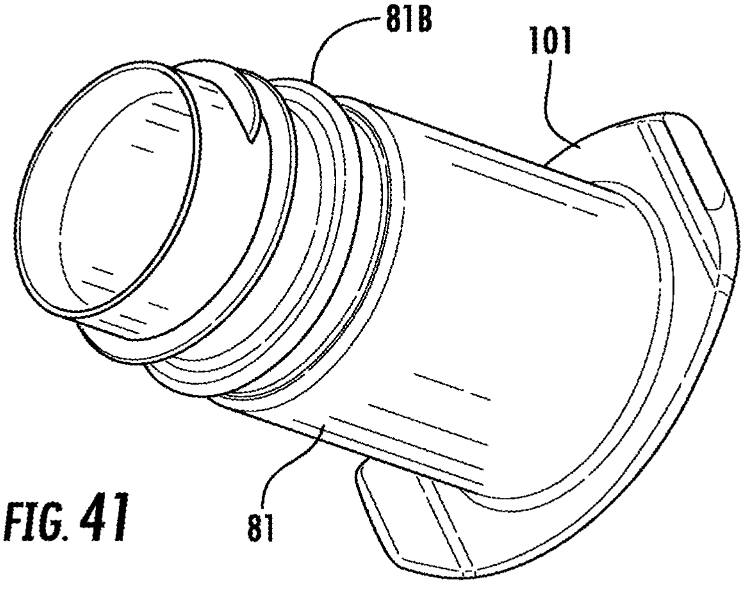
FIG. 41 is a perspective view of nozzle with an oblong lip formed integrally with the nozzle.

A nozzle 81 which is configured to be disposed within port opening 122 is show in FIGS. 38-40. Nozzle 81 is similar or identical to nozzle 81 shown in FIGS. 33-34. A clip 100 is configured to be disposed on a lip 81*a* of nozzle 81 or otherwise around a distal portion of the nozzle 81 to form an oblong lip on the nozzle 81. Clip 100 may have a C-shape such that it can be easily put on and taken off of the nozzle 81. Clip 100 has any suitable configuration or design. For example, clip 100 includes extended side portions (e.g., flanges) 111 disposed along a front surface of clip 100 and which may be configured to bend away from the front surface of clip 100 and a protrusion 110 which may extend out and away from the top surface of clip 100. Clip 100 is configured such that when clip 100 is installed on nozzle 81 and nozzle 81 is placed in port sock 122, the extended side portions (e.g., flanges) 111 of clip 100 are disposed within side pouches 125 of port sock 120. Clip 100 is configured such that when it is installed on nozzle 81, protrusion 110 of clip 100 wraps around an outer surface of nozzle 81 in a secure fit. Alternatively, protrusion 110 of clip 100 is configured to snap into an inner surface of nozzle 81. Clip 100 is configured to prevent unintentional disengagement of nozzle 81 from opening 82 or valves 84 due to an increased dimension relative to the port opening 122. Additionally, the downward bend of extended side portions 111 are configured to prevent unintentional disengagement of nozzle 81 from opening 82. Also, clip 100 is configured to prevent nozzle 81 from rotating relative to port opening 122 when nozzle 81 is disposed within port opening 122 because of the corresponding shape of the clip 100 with the side pouches 125 which allow positioning of the clip 100 in the port sock 120 in substantially only that orientation. In some aspects, clip 100 may be removable. In some aspects, clip 100 is manufactured as a single, unitary component with nozzle 81, giving the nozzle an oblong lip 101, as shown in FIG. 41. Further, as shown in FIG. 41, nozzle 81 includes, for example, a threaded portion 81*b*, configured to make nozzle 81 securably attachable to an air input or output (e.g., pump 90).

An example embodiment of a method for utilizing the system 10 is illustrated in part in FIG. 6 with respect to the embodiment in FIGS. 1-13. It is understood that the other embodiments shown and described herein, e.g., as in FIGS. 14-26 and FIGS. 30-37, may be utilized in the same or a similar method, with the same or similar functionality. As described above, the device 20 and the pad 40 may be provided as a pre-folded assembly, and the device 20 and pad 40 together may be placed beneath the patient in a pre-folded state. Examples of methods for placing the device 20 and the pad 40 beneath the patient and for removing and replacing the pad 40 are shown and described in U.S. Pat. No. 8,789,533, which is incorporated by reference herein. Once the device 20 and the pad 40 are placed beneath the patient 70, the device 20 can be inflated, by connecting the air output 81 to one of the inflation ports 80 and then fastening the retaining mechanism 83 to secure the connection. Air can then be pumped into the device 20 through the air output 81. Deflation can be accomplished by simply shutting off and/or removing the air output 81.

FIG. 6 illustrates an example embodiment of a method for placing the patient in an angled resting position by placing two wedges 50A-B under the patient 70 resting on an inflated device 20. The method is used with a patient 70 lying on a bed 12 as described above, having a bed sheet (e.g., a fitted sheet) on the supporting surface 16, with the device 20 and pad 40 of the system 10 lying on top of the bed sheet and the patient 70 lying on the pad 40. In this embodiment, the wedges 50A-B are positioned on top of the bed sheet, such that the bed sheet contacts the base wall 51 of the wedge 50A-B, and the ramp surfaces 52 of the wedges 50A-B contact the device 20. It is understood that no bed sheet or other cover for the mattress 18 may be present in some embodiments, in which case the wedges 50 can be placed directly on the mattress 18. As shown in FIG. 6, the edge of the device 20 is lifted, and the wedges 50A-B are inserted from the side of the bed 12 under the device 20 toward the patient 70. The patient 70 may be rolled all the way onto his/her side for insertion of the wedges 50A-B in one embodiment. At this point, at least the apex 55 of each wedge 50A-B may be pushed toward, next to, or at least partially under the patient 70. The selective gliding assemblies 60 between the wedges 50A-B and the bottom surface 22 of the device 20 do not resist such insertion and allow free gliding of the wedge toward the patient and away from the side edge of the bed. This insertion technique may position the patient to the desired angle with no further movement of the patient 70 necessary. In one embodiment, the wedges 50A-B should be aligned so that the wedges are spaced apart with one wedge 50A positioned at the upper body of the patient 70 and the other wedge 50B positioned at the lower body of the patient 70, with the patient's sacral area positioned in the space between the wedges 50A-B. It has been shown that positioning the wedges 50A-B in this arrangement can result in lower pressure in the sacral area, which can reduce the occurrence of pressure ulcers in the patient 70. The wedges 50A-B may be positioned approximately 10 cm apart in one embodiment, or another suitable distance to provide space to float the sacrum, or in other words, to have minimal force on the sacrum.

Once the wedges 50A-B and the support 80 have been inserted, the patient 70 may be in the proper angled position. If the patient 70 requires further turning to reach the desired angled position, the user 74 (such as a caregiver) can pull the patient 70 toward the wedges 50A-B and toward the user 74, such as by gripping the handles 28, 48 on the device 20, as shown in FIGS. 1-2. This moves the proximate edge of the device 20 toward the back walls 53 of the wedges 50A-B and toward the user 74, and slides the patient 70 and at least a portion of the device 20 up the ramp surface 52, such that the ramp surface 52 partially supports the patient 70 to cause the patient 70 to lie in an angled position. During this pulling motion, the selective gliding assemblies 60 between the ramp surfaces 52 of the wedges 50A-B and the device 20 do not resist movement of the device 20, the engagement member 64 on the base wall 51 of the wedge 50A resists movement of the wedge 50A toward the user 74 (i.e., away from the patient 70 and toward the side edge of the bed 12), and the high friction surface 24 of the device 20 resists movement of the pad 40 and/or the patient 70 with respect to the device 20.

When the patient 70 is to be returned to lying on his/her back, the wedges 50A-B can be removed from under the patient 70. The device 20 may be pulled in the opposite direction in order to facilitate removal of the wedges 50A-B and/or to position the patient 70 closer to the center of the bed 12. The patient 70 can be turned in the opposite direction by inserting the wedges 50A-B under the opposite side of the device 20, from the opposite side of the bed 12, and optionally pulling the device 20 in the opposite direction to move the patient 70 up the ramp surfaces 52 of the wedges 50A-B, in the same manner described above.

Once the wedges 50A-B are positioned beneath the patient 70 and the device 20, the various selective gliding assemblies 60 resist undesirable movement of the patient 70 and the device 20. For example, the selective gliding assemblies 60 between the ramp surfaces 52 of the wedges 50A-B and the bottom surface 22 of the device 20 resist slipping of the device 20 down the ramp surfaces 52, and also resist slipping of the device 20 downward toward the foot 17 of the bed 12, and further resist slipping of the wedges 50A-B rearward away from the patient 70 and toward the side edge of the bed 12. As another example, the selective gliding assemblies 60 on the base walls 51 of the wedge 50A-B resist slipping of the wedge 50A rearward away from the patient 70 and toward the side edge of the bed 12. These features in combination provide increased positional stability to the patient 70 as compared to existing turning and/or positioning systems, thereby reducing the frequency and degree of necessary repositioning. The patient 70, the pad 40, the device 20, and the wedges 50A-B tend to move "together" on the bed 12 in this configuration, so that these components are not unacceptably shifted in position relative to each other. This, in turn, assists in maintaining the patient 70 in optimal position for greater periods of time and reduces strain and workload for caregivers. To the extent that repositioning is necessary, the handles 28, 48 on the device 20 are configured to assist with such repositioning in a manner that reduces strain on caregivers. It is understood that the wedges 50A-B may be used in connection with the device 20 when the device 20 is in the inflated or non-inflated state. The selective glide assemblies 60 between the device 20 and the wedges 50A-B will function similarly in either state.

As described above, in some embodiments, the wedges 50A-B may have an angle of up to approximately 45°, or from approximately 15-35°, or approximately 30°. Thus, when these embodiments of wedges 50A-B are used in connection with the method as shown and described herein, the patient 70 need not be rotated or angled more than 45°, 35°, or 30°, depending on the wedge 50A-B configuration. The degree of rotation can be determined by the rotation or angle from the horizontal (supine) position of a line extending through the shoulders of the patient 70. Existing methods of turning and positioning patients to relieve sacral pressure often require rolling a patient to 90° or more to insert pillows or other supporting devices underneath. Rolling patients to these great angles can cause stress and destabilize some patients, particularly in patients with critical illnesses or injuries, and some critical patients cannot be rolled to such great angles, making turning of the patient difficult. Accordingly, the system 10 and method described above can have a positive effect on patient health and comfort. Additionally, the angled nature of the wedges 50A-B can allow for more accurate positioning of the patient 70 to a given resting angle, as compared to existing, imprecise techniques such as using pillows for support. Further, the selective gliding assemblies 60 resist undesired slipping with respect to the wedges 50A-B, which aids in maintaining the same turning angle.

The use of the system 10 and methods described above can decrease the number of pressure ulcers in patients significantly. The system 10 reduces pressure ulcers in a variety of manners, including reducing pressure on sensitive areas, reducing shearing and friction on the patient's skin, and managing heat and moisture at the patient's skin. The system 10 can reduce pressure on the patient's skin by facilitating frequent turning of the patient and providing consistent support for accurate resting angles for the patient upon turning. The system 10 can reduce friction and shearing on the patient's skin by resisting sliding of the patient along the bed 12, including resisting sliding of the patient downward after the head 13 of the bed 12 is inclined, as well as by permitting the patient to be moved by sliding the device 20 against the bed 12 instead of sliding the patient. Additionally, as described above, the use of the selective gliding assemblies and high/low friction surfaces creates a configuration where the device 20, the pad 40, the patient 70, and the wedges 50A-B all move "as one" on the bed, so that the patient 70 stays in the proper turned position and less repositioning of the patient is necessary. The system 10 can provide effective heat and moisture management for the patient by the use of the absorbent body pad. The breathable properties of the device 20 and pad 40 are particularly beneficial when used in conjunction with an LAL bed system. Increased breathability also permits the system 10 to be placed underneath the patient 70 for extended periods of time. When used properly, pressure ulcers can be further reduced or eliminated.

The use of the system 10 and methods described above can also have beneficial effects for nurses or other caregivers who turn and position patients. Such caregivers frequently report injuries to the hands, wrists, shoulders, back, and other areas that are incurred due to the weight of patients they are moving. Use of the system 10, including the device 20 and the wedges 50A-B, can reduce the strain on caregivers when turning, positioning, boosting, and/or transferring patients. For example, existing methods for turning and positioning a patient 70, such as methods including the use of a folded-up bed sheet for moving the patient 70, typically utilize lifting and rolling to move the patient 70, rather than sliding. Protocols for these existing techniques encourage lifting to move the patient and actively discourage sliding the patient, as sliding the patient using existing systems and apparatuses can cause friction and shearing on the patient's skin. The case of motion and reduction in shearing and friction forces on the patient 70 provided by the system 10 allows sliding of the patient 70, which greatly reduces stress and fatigue on caregivers while moving and/or turning the patient 70. The combination of the low friction material 25 and the airflow through the passages 37 greatly reduces friction in moving the patient 70. In particular, these features provide decreased force necessary for "boosting" a patient 70 toward the head 13 of the bed 12. It has been found that the use of an inflated device 20 as described herein and shown in FIGS. 1-6 can reduce the peak force necessary to boost a supine patient a distance of 12 inches toward the head 13 of a standard hospital bed 12 by 60-70%, in comparison to a typical boosting procedure using a folded-over bed sheet to move the patient. It has also been found that the use of an inflated device 20 as described herein and shown in FIGS. 1-6 can reduce the peak force necessary to boost a supine patient a distance of 12 inches toward the head 13 of a standard hospital bed 12 by 55-65%, in comparison to a boosting procedure using a sheet with a low-friction bottom surface to move the patient. Still other benefits and advantages over existing technology are provided by the system 10 and methods described herein, and those skilled in the art will recognize such benefits and advantages.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. The terms "first," "second," "top," "bottom," etc., as used herein, are intended for illustrative purposes only and do not limit the embodiments in any way. In particular, these terms do not imply any order or position of the components modified by such terms. Additionally, the term "plurality," as used herein, indicates any number greater than one, either disjunctively or conjunctively, as necessary, up to an infinite number. Further, "providing" an article or apparatus, as used herein, refers broadly to making the article available or accessible for future actions to be performed on the article, and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention.

What is claimed is:

1. A first wedge for use in positioning a patient on a support surface, the first wedge comprising:
- a first wedge body comprising:
  - a first base wall comprising:
    - a plurality of first base wall edges,
    - a first base wall first portion contiguous with each of the first base wall edges, the first base wall first portion having a first base first coefficient of friction, and
    - a first base wall second portion surrounded by the first base wall first portion, the first base wall second portion having a first base second coefficient of friction, the first base second coefficient of friction greater than the first base first coefficient of friction,
  - a first ramp surface, the first ramp surface contiguous with the first base wall,
  - a first back wall contiguous with the first base wall and the first ramp surface; and
  - a beveled surface extending between the first ramp surface and the first base wall, the beveled surface located opposite and offset from the first back wall, the beveled surface perpendicular to the first base wall.

2. The first wedge of claim 1, wherein:
- the first ramp surface includes:
  - a plurality of first ramp edges,
  - a first ramp surface first portion contiguous with each of the first ramp edges, the first ramp surface first portion having a first ramp first coefficient of friction, and
  - a first ramp surface second portion surrounded by the first ramp surface first portion, the first ramp surface second portion having a first ramp second coefficient of friction, the first ramp second coefficient of friction greater than the first ramp first coefficient of friction.

3. The first wedge of claim 2, wherein the first ramp first coefficient of friction is equal to the first base first coefficient of friction.

4. The first wedge of claim 2 wherein the first ramp second coefficient of friction is equal to the first base second coefficient of friction.

5. The first wedge of claim 2, wherein the first ramp surface second portion is centered between a first ramp edge contiguous with the first back wall and a first ramp edge contiguous with the first base wall.

6. The first wedge of claim 2, wherein:
- the first wedge further comprises:
  - a first side wall extending between the first base wall, the first ramp surface, and the first back wall, and
  - a second side wall opposite the first side wall, the second side wall extending between the first base wall, the first ramp surface, and the first back wall, and
- the first ramp surface second portion is centered between a first ramp edge contiguous with the first side wall and a first ramp edge contiguous with the second side wall.

7. The first wedge of claim 2, wherein the first ramp surface second portion is a rectangular patch.

8. The first wedge of claim 1, wherein the first base wall second portion is a rectangular patch.

9. The first wedge of claim 1, wherein:

the first base wall second portion is located closer to the beveled surface than the first back wall.

10. The first wedge of claim 1, wherein:

the first wedge further comprises:

a first side wall extending between the first base wall, the first ramp surface, and the first back wall, and a second side wall opposite the first side wall, the second side wall extending between the first base wall, the first ramp surface, and the first back wall, and the first base wall second portion is centered between a first base wall edge contiguous with the first side wall and a first base wall edge contiguous with the second side wall.

11. The first wedge of claim 1, wherein:

the first ramp surface is separated from the first back wall by a ramp angle;

the first back wall is separated from the first base wall by a back angle; and the first base wall is separated from the first ramp surface by an apex angle, the apex angle being less than the ramp angle and the back angle.

12. The first wedge of claim 11, wherein the apex angle is between 15 degrees and 35 degrees.

13. The first wedge of claim 1, wherein the first wedge body includes:

a non-compressible core; and a compressible shell around the non-compressible core.

14. The first wedge of claim 1, wherein the first ramp surface is concave.

15. A system for use in positioning a patient on the support surface, the system including:

the first wedge of claim 1; and a second wedge comprising:

a second wedge body comprising:

a second base wall, a second ramp surface, the second ramp surface contiguous with the second base wall, and a second back wall contiguous with the second base wall and the second ramp surface;

wherein the second wedge is configured to be positioned on the support surface independent of the first wedge.

16. The system of claim 15, wherein:

the second base wall comprises:

a plurality of second base wall edges, a second base wall first portion contiguous with each of the second base wall edges, the second base wall first portion having a second base first coefficient of friction, and a second base wall second portion surrounded by the second base wall first portion, the second base wall second portion having a second base second coefficient of friction, the second base second coefficient of friction greater than the second base first coefficient of friction.

17. The system of claim 15, wherein:

the second ramp surface comprises:

a plurality of second ramp surface edges, a second ramp surface first portion contiguous with each of the second ramp surface edges, the second ramp surface first portion having a second ramp first coefficient of friction, and a second ramp surface second portion surrounded by second ramp surface first portion, the second ramp surface second portion having a second ramp second coefficient of friction, the second ramp second coefficient of friction greater than the second ramp first coefficient of friction.

18. A first wedge for use in positioning a patient on a support surface, the first wedge comprising:

a first wedge body comprising:

a first base wall, a first back wall, a first ramp surface, the first ramp surface contiguous with the first base wall, the first ramp surface comprising:

a plurality of first ramp surface edges, a first ramp surface first portion contiguous with each of the first ramp surface edges, the first ramp surface first portion having a first ramp first coefficient of friction, and a first ramp surface second portion surrounded by the first ramp surface first portion, the first ramp surface second portion having a first ramp second coefficient of friction, the first ramp second coefficient of friction greater than the first ramp first coefficient of friction; and a beveled surface extending between the first ramp surface and the first base wall, the beveled surface located opposite and offset from the first back wall, the beveled surface perpendicular to the first base wall.

19. A first wedge for use in positioning a patient on a support surface, the first wedge comprising:

a first wedge body comprising:

a first base wall comprising:

a first base wall first portion, the first base wall first portion having a first base first coefficient of friction, and a first base wall second portion surrounded by the first base wall first portion, the first base wall second portion having a first base second coefficient of friction, the first base second coefficient of friction greater than the first base first coefficient of friction, a first ramp surface, the first ramp surface contiguous with the first base wall, the first ramp surface comprising:

a first ramp surface first portion having a first ramp first coefficient of friction, and a first ramp surface second portion surrounded by the first ramp surface first portion, the first base wall second portion having a first ramp second coefficient of friction, the first ramp second coefficient of friction greater than the first ramp first coefficient of friction;

a first back wall; and a beveled surface extending between the first ramp surface and the first base wall, the beveled surface located opposite and offset from the first back wall, the beveled surface perpendicular to the first base wall.

* * * * *